US006846917B2

(12) United States Patent
Seeberger et al.

(10) Patent No.: US 6,846,917 B2
(45) Date of Patent: Jan. 25, 2005

(54) SOLID- AND SOLUTION-PHASE SYNTHESIS OF HEPARIN AND OTHER GLYCOSAMINOGLYCANS

(75) Inventors: Peter H. Seeberger, Cambridge, MA (US); Hernan Orgueira, Cambridge, MA (US); Peter Schell, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/054,724

(22) Filed: Jan. 22, 2002

(65) Prior Publication Data

US 2003/0013862 A1 Jan. 16, 2003

Related U.S. Application Data

(60) Provisional application No. 60/263,621, filed on Jan. 23, 2001.

(51) Int. Cl.$^7$ ............................. C07H 13/02; C07H 5/04
(52) U.S. Cl. ...................... 536/18.7; 536/116; 536/119; 536/120; 536/55.1; 536/123.1; 536/123.12; 536/124; 536/126
(58) Field of Search ................................. 536/18.7, 116, 536/119, 120, 55.1, 123.1, 124, 126, 55.2, 21, 1.11; 514/54, 56, 61

(56) References Cited

U.S. PATENT DOCUMENTS

| | | | |
|---|---|---|---|
| 4,916,219 A | 4/1990 | Linhardt et al. | 536/21 |
| 5,314,876 A | 5/1994 | Lormeau et al. | 514/56 |
| 5,382,570 A | 1/1995 | Petitou et al. | 514/53 |
| 5,529,985 A | 6/1996 | Petitou et al. | 514/53 |
| 5,543,403 A | 8/1996 | Petitou et al. | 514/54 |
| 5,614,506 A | 3/1997 | Falk et al. | 514/54 |
| 5,618,798 A | 4/1997 | Bar-Shalom et al. | 514/53 |
| 5,639,738 A | 6/1997 | Falk et al. | 514/54 |
| 5,700,916 A * | 12/1997 | Kahne et al. | 536/1.11 |
| 5,739,115 A | 4/1998 | Fugedi et al. | 514/23 |
| 5,767,104 A | 6/1998 | Bar-Shalom et al. | 514/53 |
| 5,773,605 A | 6/1998 | Petitou et al. | 536/118 |
| 5,834,444 A | 11/1998 | Falk et al. | 514/54 |
| 5,861,382 A | 1/1999 | Cohen et al. | 514/53 |
| 5,869,273 A | 2/1999 | Klock | 435/7.92 |
| 5,908,867 A | 6/1999 | Henry et al. | 514/693 |
| 5,922,690 A | 7/1999 | Van Gorp et al. | 514/54 |
| 5,955,325 A | 9/1999 | Habuchi | 435/100 |
| 5,968,822 A | 10/1999 | Pecker et al. | 435/325 |
| 5,990,095 A | 11/1999 | Falk et al. | 514/54 |
| 6,017,513 A | 1/2000 | Betheder et al. | 424/1.73 |
| 6,020,323 A | 2/2000 | Cohen et al. | 514/53 |
| 6,022,866 A | 2/2000 | Falk et al. | 514/54 |
| 6,025,444 A | 2/2000 | Waki et al. | 525/293 |
| 6,107,410 A | 8/2000 | Waki et al. | 525/293 |
| 6,143,730 A | 11/2000 | Parish et al. | 514/54 |
| 6,174,863 B1 | 1/2001 | Van Boeckel et al. | 514/25 |
| 6,190,875 B1 | 2/2001 | Ben-Artzi et al. | 435/18 |
| 6,197,568 B1 | 3/2001 | Marks et al. | 435/239 |
| 6,287,789 B1 | 9/2001 | Klock | 435/7.21 |
| 6,310,073 B1 | 10/2001 | Kisilevsky et al. | 514/292 |

FOREIGN PATENT DOCUMENTS

| | | |
|---|---|---|
| EP | 0 529 715 A1 | 3/1993 |
| EP | 0 529 715 B1 | 3/1993 |
| EP | 0 618 234 A1 | 10/1994 |
| EP | 0 618 235 A1 | 10/1994 |
| WO | WO 94/11006 | 5/1994 |
| WO | WO 98/17284 | 4/1998 |
| WO | WO 98/48816 | 11/1998 |

OTHER PUBLICATIONS

Tamura, J. "Recent Advances in the Synthetic Studies of Glycosaminoglycans", Trend in Glycoscience and Glycotechnology, 2001, 13(69), 65–88.*

Westman, J. et al "Synthesis and fibroblast growth factor binding of oligosaccharides related to heparin and heparin sulfate", Journal of Carbohydrate Chemistry, 1995, 14(1), 95–113.*

Nilsoon, M. "Synthesis of methyl glycosides of a tri– and a tetrasacchardie related to heparin and heparan sulfate", Carbohydrate R search, 1993, 246, 161–172.*

Ichikawa, Y. et al "Synthetic studies on mucopolysaccharides. Part III. Synthesis, from cellobiose of a trisaccharide closely related to the GlcNAc–>GlcA–>GlcN segment of the antithrombin–binding sequence of heparin", Carbohydrate Research, 1985, 141(2).*

Jaurand, G. et al "Biologically active heparin–like fragments with a "non–glycosamino" glycan structure, Part I. A pentasaccharide containing a 3–O–methyl iduronic acid unit", Bioorganic and Medicinal Chemistry Letters, 1992, 2(9), 897–900.*

(List continued on next page.)

Primary Examiner—James O. Wilson
Assistant Examiner—Ganapathy Krishnan
(74) Attorney, Agent, or Firm—Dana M. Gordon; Foley Hoag LLP

(57) ABSTRACT

Described is a modular, general synthetic strategy for the preparation in solution and on a solid support of heparin, heparin-like glycosaminoglycans, glycosaminoglycans and non-natural analogs of each of them. Additionally, the modular strategy provides the basis for the preparation of combinatorial libraries and parallel libraries of defined glycosaminoglycan oligosaccharides. The defined glycosaminoglycan structures may be used in high-throughput screening experiments to identify carbohydrate sequences that regulate a host of recognition and signal-transduction processes. The determination of specific sequences involved in receptor binding holds great promise for the development of molecular tools which will allow modulation of processes underlying viral entry, angiogenesis, kidney diseases and diseases of the central nervous system. Notably, the present invention enables the automated synthesis of glycosaminoglycans in much the same fashion that peptides and oligonucleotides are currently assembled.

25 Claims, 17 Drawing Sheets

OTHER PUBLICATIONS

Kovensky, S. et al "A synthetic Heparan sulfate pentasaccharide, exclusively containing L–iduronic acid, displays higher affinity for FGF–2 than its D–glucuronic acid–containing isomers", Biorganic and Medicinal Chemistry, 1999, 7(8), 1567–1580.*

Lei, P–S. et al "Synthesis of 3–deoxy–L–iduronic acid containing heparin pentasaccharide to probe the conformation of antithrombin III binding sequence", Bioorganic and Medicinal Chemistry, 1998 6(8), 1337–1346.*

Tamura et al "Synthetic Studies of Glycosyl Serines in the Carbohydrate–Protein Region of Protoglycans", Liebigs Ann., 1996, 1239–1257.*

Stephen P. Douglas et al "Polymer–Supported Solution Synthesis or Oligosaccharides", J. Am. Chem. Soc. 1991, 113(13), 509 5097.*

Westman, J., et al., "Synthesis and Fibroblast Growth Factor Binding Of Oligo–Saccharides Related To Heparin and Heparan Sulphate", J. Carbohydrate Chemistry, 14(1), 95–113 (1995).

Nilsson, M., et al., "Synthesis of the methyl glycosides of a tri– and a tetra–saccharide related to heparin and heparan sulphate", Carbohydrate Research, 246 (1993) 161–172.

Ichikawa, Y., et al., "Synthesis, From Cellobiose, Of A Trisaccharide Closely Related To The GlcNAc–GlcA–GlcN Segment Of The Anti–Thrombin–Binding Sequence of Heparin", Carbohydrate Research, 141 (1985) 273–282.

Jauranda, G., et al., "Biologically Active Heparin–Like Fragments With A "Non–Glycosamino" Glycan Structure. Part 1: A Pentasacchardie Containing A 3–0–Methyl Iduronic Acid Unit", Bioorganic & Medicinal Chemistry Letters, vol. 2, No. 9, pp. 897–900, 1992.

Kovensky, J., et al., "A Synthetic Heparan Sulfate Pentasacchardie, Exclusively Containing L–Iduronic Acid, Displays Higher Affinity for FGF–2 than its D–Glucuronic Acid–Containing Isomers", Biorganic & Medicinal Chemistry 7 (1999) 1567–1580.

Lei, P.S., et al., "Synthesis of 3–Deoxy–L–iduronic Acid Containing Heparin Pentasaccharide to Probe the Conoformation of the Antithrombin III Binding Sequence", Bioorganic & Medicinal Chemistry 6 (1998) 1337–1346.

Koshida et al.; "Synthesis of Oligomeric Assemblies of a Platelet–Binding Key Disaccharide in Heparin and Their Biological Activities", Tetrahedron Letters 42: 1289–1292, (2001).

Jun–ichi Tamura, "Recent Advances in the Synthetic Studies of Glycosaminoglycans", Trends in Glycoscience and Glycotechnology, 13(69): 65–88, (Jan. 2001).

Koshida et al.; "Synthesis and Biological Activity of Oligomer–Model Compounds Containing Units of a Key Platelet–binding Disaccharde of Heparin", Tetrahedron Letters 40: 5725–5728, (1999).

Kovensky et al.; "Binding of Heparan Sulfate to Fibroblast Growth Factor–2 Total Synthesis of a Putative Pentasaccharide Binding Site", Tetrahedron Asymmetry 7(11): 3119–3128 (1996).

Suda et al.; "Synthesis and Biological Activity of a Model Disacchardie Containing a Key Unit in Heparin for Binding to Platelets", Tetrahedron Letters 37(7): 1053–1056, (1996).

International Search Report Completed on Jun. 5, 2002 and Mailed on Aug. 20, 2002.

* cited by examiner

SOLID- AND SOLUTION-PHASE SYNTHESIS OF HEPARIN AND OTHER GLYCOSAMINOGLYCANS

RELATED APPLICATIONS

This application claims the benefit of priority to the filing date of U.S. Provisional Patent Application Ser. No. 60/263,621, filed Jan. 23, 2001.

GOVERNMENT SUPPORT

This invention was made with government support under Grant Number NIH-1R01-HL64799 awarded by the National Institues of Health. The government has certain rights in the invention.

BACKGROUND OF THE INVENTION

Nucleic acids, proteins and polysaccharides constitute the three major classes of biopolymers. While the first two systems are principally linear assemblies, polysaccharides are structurally more complex. This structural and stereochemical diversity results in a rich content of "information" in relatively small molecules. Nature further "leverages" the structural biomolecules such as isoprenoids, fatty acids, neutral lipids, peptides or proteins. Oligosaccharides in the form of glycoconjugates mediate a variety of events including inflammation, immunological response, metastasis and fertilization. Cell surface carbohydrates act as biological markers for various tumors and as binding sites for other substances including pathogens.

Proteoglycans are complex protein-carbohydrate assemblies that consist of a core protein and one or more covalently attached glycosaminoglycan chains. For reviews, see: R. V. Iozzo, *Annu. Rev. Biochem.* 1998, 67, 609–652; and M. Bemfield, M. Gotte, P. W. Park, O. Reizes, M. L. Fitzgerald, J. Lincecum, M. Zako, *Annu. Rev. Biochem.* 1999, 68, 729–777. These linear polysaccharides range in length from ~20 to 200 disaccharide repeat units, each composed of an amino sugar and an uronic acid moiety (FIG. 1).

Heparin-like glycosaminoglycans (HLGAGs) are the most acidic naturally occurring biopolymers. These complex polysaccharides, found in the extracellular matrix, play a key role in regulating the biological activity of several proteins in the coagulation cascade along with many other processes of biomedical importance including growth factor interactions, virus entry, and angiogenesis. H. E. Conrad, *Heparin Binding Proteins*; Academic Press 1998. Heparin, isolated from the mast cells of pigs, is currently produced in multi-ton quantities and used in a variety of medical applications. H. Engelberg, *Pharmacol. Rev.* 1984, 36, 91–110. Most prominent is the use of heparin as an anticoagulant in heart disease where it has served as a therapeutic agent since the late 1930s. The heterogeneity of heparin results in many severe side effects, making this inexpensive drug dangerous and necessitates close monitoring. B. H. Chong, *Aust. N.Z. J Med.* 1992, 22, 145–152.

The heparin-antithrombin III (AT-III) interaction is responsible for heparin's anticoagulant activity and is the only system where the exact sequence of heparin that associates with the protein has been identified. Extensive structure-activity studies using synthetic oligosaccharides (M. Petitou, P. Duchaussoy, G. Jaurand, F. Gourvenec, I. Lederman, J.-M. Strassel, T. Barzu, B. Crepon, J.-P. Herault, J.-C. Lormeau, A. Bernat, J.-M. Herbert, *J. Med. Chem.* 1997, 40, 1600–1607; and S. Koshida, Y. Suda, M. Sobel, J. Ormsby, S. Kusumoto, *Bioorg. Med. Chem. Lett.* 1999, 9, 3127–3132.) as well as NMR (M. Iacomini, B. Casu, M. Guerrini, A. Naggi, A. Pirola, G. Torri, *Anal. Biochem.* 1999, 274, 50–58.) and X-ray crystallography (S. Faram, R. E. Hileman, J. R. Fromm, R. J. Linhardt, D. C. Rees, *Science* 1996, 271, 1116–1120.) have been performed. Based on these studies, a concerted drug development effort has been undertaken, resulting in the development of a synthetic pentasaccharide heparin analog for use in humans. M. Petitou, P. Duchaussoy, P. A. Driguez, G. Jaurand, J. P. Herault, J. C. Lormeau, C. A. A. van Boeckel, J. M. Herbert, *Angew. Chem. Int. Ed.* 1998, 37, 3009–3014, *Angew. Chem.* 1998, 110, 3186–3191; and B. Mulloy, M. J. Forster, *Glycobiology* 2000, 10, 1147–1156. With the exception of the AT-III-heparin interaction, the relationship between structure and function of HLGAGs is still poorly understood due to the complexity and heterogeneity of these polymers. Defined HLGAG oligosaccharides constitute valuable molecular tools to gain a detailed understanding of the sequences of HLGAGs responsible for binding to a particular protein and modulating its biological activity. For reviews, see: R. V. Iozzo, *Annu. Rev. Biochem.* 1998, 67, 609–652; and M. Bernfield, M. Gotte, P. W. Park, O. Reizes, M. L. Fitzgerald, J. Lincecum, M. Zako, *Annu. Rev. Biochem.* 1999, 68, 729–777. Determination of the structure-activity relationships of HLGAGs will create an opportunity for the discovery of novel therapeutic interventions for many disease states.

Over the past two decades, a variety of synthetic methods directed at the preparation of HLGAG oligosaccharides have been disclosed and heroic total syntheses (P. Sinay, J.-C. Jacquinet, *Carbohydr. Res.* 1984, 132, C5–C9; M. Petitou, P. Duchaussoy, I. Lederman, J. Choay, P. Sinay, J.-C. Jacquinet, D. Iorri, *Carbohydr. Res.* 1986, 147, 221–236.) have resulted in the assembly of AT-III-binding HLGAG oligosaccharides. C. A. A. van Boeckel, M. Petitou, *Angew. Chem. Int. Ed. Engl.* 1993, 32, 1671–1690, *Angew. Chem.* 1993, 105, 1741–1761; P. Westerduin, J. E. M. Basten, M. A. Broekhoven, V. de Kimpe, W. H. A. Kuijpers, C. A. A. van Boeckel, *Angew. Chem. Int. Ed. Engl.* 1996, 35, 331–333, *Angew. Chem.* 1996, 108, 339–342. More recently, longer oligosaccharide HLGAG analogs exhibiting impressive biological activity have been prepared using simplified syntheses. M. Petitou, J.-P. Herault, A. Bernat, P.-A. Driguez, P. Duchaussoy, J.-C. Lormeau, J.-M. Herbert, *Nature*, 1999, 398, 417–422. Still, the procurement of specific HLGAG sequences required the development of a new total synthesis stratgey for each oligosaccharide target.

Moreover, many additional physiologically-important recognition phenomena involving carbohydrates have been discovered in recent years. Lectins, proteins which contain carbohydrate recognition domains, have been identified. Prominent members of the calcium dependent (C-type) lectin family (Drickamer, K. *Curr. Opin. Struct. Biol.* 1993, 3, 393) are the selectins which play a crucial role in leukocyte recruitment in inflammation. Bevilacqua, M. P.; Nelson, R. M. *J. Clin. Invest.* 1993, 91, 379. Members of the C-type lectin superfamily have been described on NK cells and Ly-49, NKR-P1 and NKG2 constitute group V of C-type lectins. While many lectins have been purified and cloned, their ligands have not been identified due to the heterogeneous nature of carbohydrates.

The recognition that interactions between proteins and carbohydrates are involved in a wide array of biological recognition events, including fertilization, molecular targeting, intercellular recognition, and viral, bacterial and fungal pathogenesis, underscores the importance of carbohyrates in biological systems. It is now widely appreciated that the oligosaccharide portions of glycoproteins and glycolipids mediate certain recognition events between cells, between cells and ligands, between cells and the extracellular matrix, and between cells and pathogens. See, e.g., U.S. Pat. No. 4,916,219 (describing oligosaccharides with heparin-like anticomplement activity).

These recognition phenomena may be inhibited by oligosaccharides having the same sugar sequence and stereochemistry found on the active portion of a glycoprotein or glycolipid involved in the recognition phenomena. The oligosaccharides are believed to compete with the glycoproteins and glycolipids for binding sites on the relevant receptor(s). For example, the disaccharide galactosyl-β-1-4-N-acetylglucosamine is believed to be one component of the glycoproteins which interact with receptors in the plasma membrane of liver cells. Thus, to the extent that they compete with moieties for cellular binding sites, oligosaccharides and other saccharide compositions have the potential to open new horizons in pharmacology, diagnosis, and therapeutics.

The growing appreciation of the key roles of oligosaccharides and glycoconjugates in fundamental life sustaining processes has stimulated a need for access to usable quantities of these materials. Glycoconjugates are difficult to isolate in homogeneous form from living cells since they exist as microheterogeneous mixtures. The purification of these compounds, when possible, is at best tedious and generally provides only very small amounts of the compounds. The travails associated with isolation of oligo- and poly-saccharides and glycoconjugates from natural sources present a major motivation for the development and exploitation of chemical synthesis. See, e.g., U.S. Pat. Nos. 4,656,133; 5,308,460; 5,514,784; and 5,854,391 (describing various means of glycosylating saccharides and peptides).

Intense work on the further development of the use of biologically-active oligosaccharides is ongoing within a number of fields, including: novel diagnostics and blood typing reagents; highly specific materials for affinity chromatography; cell specific agglutination reagents; targeting of drugs; monoclonal antibodies, e.g., against cancer-associated reagents; antibiotic alternatives, based on the inhibition with specific oligosaccharides of the attachment of bacteria and viruses to cell surfaces; and stimulation of the growth of plants and protection of them against pathogens.

The invention of solid phase peptide synthesis by Merrifield 35 years ago dramatically influenced the strategy for the synthesis of biopolymers. The preparation of structurally defined oligopeptides (Atherton, E.; Sheppard, R. C. *Solid phase peptide synthesis: A practical approach*; IRL Press at Oxford University Press: Oxford, England, 1989, pp 203) and oligonucleotides (Caruthers, M. H. *Science* 1985, 230, 281) has benefited greatly from the feasibility of conducting their assembly on various polymer supports. The advantages of solid matrix-based synthesis, in terms of allowing for an excess of reagents to be used and in the facilitation of purification are now well appreciated. However, the level of complexity associated with the synthesis of an oligosaccharide on a polymer support dwarfs that associated with the other two classes of repeating biooligomers. First, the need to differentiate similar functional groups (hydroxyl and amino) in oligosaccharide construction is much greater than the corresponding needs in the synthesis of oligopeptides or oligonucleotides. Furthermore, in these latter two cases, there is no stereoselection associated with construction of the repeating amide or phosphate bonds. In contrast, each glycosidic bond fashioned in a growing oligosaccharide ensemble constitutes a new locus of stereogenicity.

Combinatorial chemistry has been used in the synthesis of large numbers of structurally distinct molecules in a time and resource-efficient manner. Peptide, oligonucleotide, and small molecule libraries have been prepared and screened against receptors or enzymes to identify high-affinity ligands or potent inhibitors. These combinatorial libraries have provided large numbers of compounds to be screened against many targets for biological activity. Every pharmaceutical company now devotes a major effort to the area of combinatorial chemistry in order to develop new lead compounds in a rapid fashion.

The development of protocols for the solid support synthesis of oligosaccharides and glycopeptides requires solutions to several problems. Of course, considerable thought must be addressed to the nature of the support material. The availability of methods for attachment of the carbohydrate from either its "reducing" or "non-reducing" end would be advantageous. Also, selection of a linker which is stable during the synthesis, but can be cleaved easily when appropriate, is critical. A protecting group strategy that allows for high flexibility is desirable. Most important is the matter of stereospecific and high yielding coupling reactions.

Combinatorial carbohydrate libraries also hold a tremendous potential with regard to therapeutic applications. The key role complex oligosaccharides play in biological processes, such as inflammation, immune response, cancer and fertilization makes them highly attractive therapeutic targets. The ability to create true oligosaccharide libraries has the potential to trigger a revolution in the area of biopharmaceuticals. For example, the generation of combinatorial carbohydrate libraries will facilitate the rapid identification of ligands to many carbohydrate binding proteins which are involved in a variety of important biological events including inflammation (Giannis, A. *Angew. Chem. Int. Ed. Eigl.* 1994, 33, 178), immune response (Ryan, C. A. *Proc. Natl. Acad. Sci. U.S.A.* 1994, 91, 1) and metastasis (Feizi, T. *Curr. Opin. Struct. Biol.* 1993, 3, 701). Analogs of ligands can help to define important lectin-ligand interactions. Non-natural ligands can be powerful inhibitors of carbohydrate-protein binding and will facilitate the study of cascade-like events involving such interactions. Furthermore, inhibitors of carbohydrate-lectin binding are potential candidates for a variety of therapeutic applications.

As stated above, due to the difficulties associated with purification of glycoconjugates and oligosaccharides from natural sources, chemical synthesis may be the only way to procure sufficient amounts of these structures for detailed biochemical and biophysical studies. Additionally, combinatorial carbohydrate libraries hold great potential for the identification of carbohydrate-based ligands to cellular receptors. Identification of these molecules will open many new avenues for the development of diagnostic tools and therapeutic agents.

SUMMARY OF THE INVENTION

Described is a modular, general synthetic strategy for the preparation in solution and on a solid support of heparin, heparin-like glycosaminoglycans, glycosaminoglycans and non-natural analogs of each of them. Additionally, the modular strategy provides the basis for the preparation of combinatorial libraries and parallel libraries of defined glycosaminoglycan oligosaccharides. The defined glycosaminoglycan structures may be used in high-throughput screening experiments to identify carbohydrate sequences that regulate a host of recognition and signal-transduction processes. The determination of specific sequences involved in receptor binding holds great promise for the development of molecular tools which will allow modulation of processes underlying viral entry, angiogenesis, kidney diseases and diseases of the central nervous system. Notably, the present invention enables the automated synthesis of glycosaminoglycans in much the same fashion that peptides and oligonucleotides are currently assembled.

DETAILED DESCRIPTION OF THE INVENTION

Overview of the Present Invention

Described is a modular, general synthetic strategy for the preparation in solution and on a solid support of heparin, heparin-like glycosaminoglycans, glycosaminoglycans and non-natural analogs of each of them. Additionally, the modular strategy provides the basis for the preparation of combinatorial libraries and parallel libraries of defined glycosaminoglycan oligosaccharides. The defined glycosaminoglycan structures may be used in high-throughput screening experiments to identify carbohydrate sequences that regulate a host of recognition and signal-transduction processes. The determination of specific sequences involved in receptor binding holds great promise for the development of molecular tools which will allow modulation of processes underlying viral entry, angiogenesis, kidney diseases and diseases of the central nervous system. Notably, the present invention enables the automated synthesis of glycosaminoglycans in much the same fashion that peptides and oligonucleotides are currently assembled.

Figure 1:
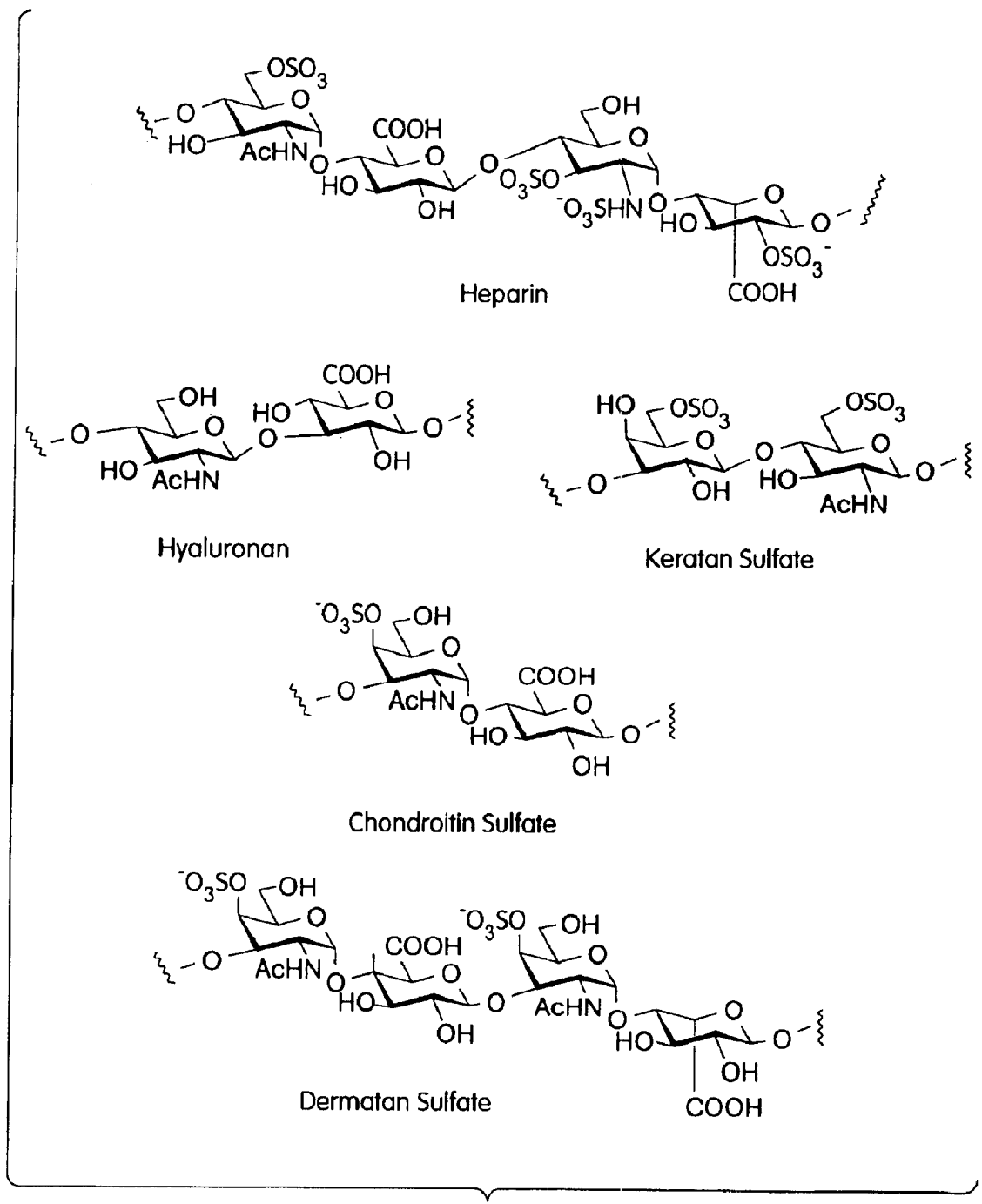
FIG. 1 depicts various classes of glycosaminoglycans.

Glycosaminoglycans are hetereogeneous polysaccharides that are anchored in the cellular membrane and constitute a major portion of the extracellular matrix. Heparin, dermatan, hyaluronic acid, and keratan all differ in the type of sugars that are part of the polysaccharide and/or the type of linkage that connects these sugars. See FIG. 1. Although syntheses of short oligosaccharide segments of each type of glycosaminoglycans have been described previously, most of these syntheses were extremely laborious and required a distinct total synthesis strategy for each structure targeted. In contrast, the approach of the present invention is based on the assembly of any glycosaminoglycan from a limited set of disaccharide building blocks, in a modular fashion that may be carried out on solid support. The method described here lends itself particularly well to synthesis automation and the preparation of combinatorial libraries and parallel libraries of defined oligosaccharides.

Modular Synthesis Strategy of the Present Invention

The structural complexity of HLGAG oligosaccharides necessitates a flexible synthetic approach. Such an approach allows for the preparation of a wide variety of defined structures without requiring the redesign of the synthesis. Therefore, a highly convergent, fully modular synthetic plan was devised to maximize flexibility and to minimize the number of transformations required to fashion an oligosaccharide product. A modular, highly convergent synthetic approach for the rapid assembly of defined HLGAG oligosaccharide sequences and libraries of defined glycosaminoglycans and non-natural analogs is described. Such an approach required careful consideration of the many synthetic challenges presented by the great diversity of native structures. The sulfation patterns mandated the placement of specific protecting groups in all positions to carry sulfates and different protection on hydroxyls that remain unaltered. The amine portion of the glucosamine component has been found to be acetylated, sulfated and to exist as the free amine (D. Shukla, J. Liu, P. Blaiklock, N. W. Shworak, X. M. Bai, J. D. Esko, G. H. Cohen, R. J. Eisenberg, R. D. Rosenberg, P. G. Spear, *Cell* 1999, 99, 13–22), thus requiring a protecting group scheme that allows for the differentiation of this position.

In addition to the installation of a host of protective groups, the creation of the glycosidic linkages making up the backbone of HLGAGs posed several challenges. The use of uronic acid derivatives as glycosidating agents had received little attention (C. Tabeur, F. Machetto, J.-M. Mallet, P. Duchaussoy, M. Petitou, P. Sinay, *Carbohydr. Res.* 1996, 281, 253–276; C. Krog-Jensen, S. Oscarson, *Carbohydr. Res.* 1998, 308, 287–296) and was often circumvented (C. Tabeur, J.-M. Mallet, F. Bono, J.-M. Herbert, M. Petitou, P. Sinay, *Bioorg. Med. Chem. Lett.* 1999, 7, 2003–2012; M. Haller, G.-J. Boons, *J. Chem. Soc., Perkin Trans* 1 2001, 814–822) due to the inherent low reactivity imposed by the C5 ester. Stereocontrol during the fashioning of the α-glucosamine linkage was difficult as anchimeric assistance cannot be exploited thus resulting in the formation of mixtures of glycosides. M. Haller, G.-J. Boons, *J. Chem. Soc., Perkin Trans* 1 2001, 814–822. Separation of such anomeric mixtures often necessitated very difficult chromatographic steps. Finally, the preparation of iduronic acid monosaccharides required lengthy synthetic procedures.

Figure 2:
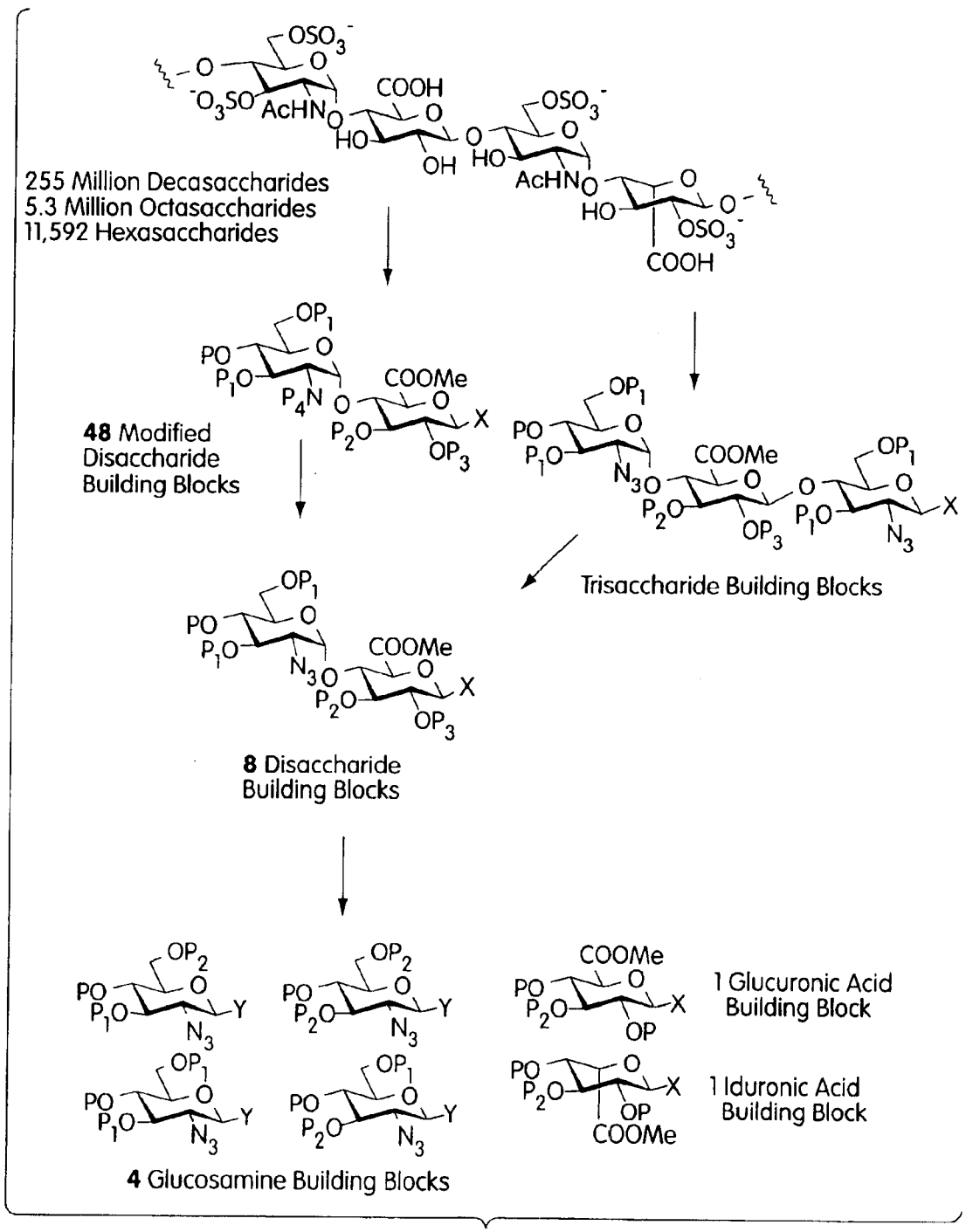
FIG. 2 depicts a modular synthesis of heparin according to the present invention.

The cornerstone of the modular approach described here is its high convergency that allows for the preparation of large numbers of oligosaccharides from a very limited number of fully functionalized monosaccharide building blocks. See FIG. 2. Using heparin as an example, four differentially protected glucosamine building blocks can be combined with one glucuronic acid building block and one iduronic acid building block to form eight different disaccharide modules. Modification on the C2 position to allow for introduction of either the C2 hydroxyl or a C2 sulfate and modification of the C2' amine as N-acetate, N-sulfate or free amine results in a total of 48 different building blocks that can be combined in a two-step coupling, deprotection cycle to fashion defined oligosaccharides in a highly convergent fashion. Further elaboration has been achieved to include trisaccharide building blocks.

Disclosed is a novel, convergent synthesis of the glucosamine derivatives from glucosamine as common precursor. New synthetic protocols for the preparation of uronic acid glycosyl donors are also dislcosed. The generation of the disaccharide modules relies on a new design feature for the control of stereochemistry during glycoside formation. By constraining the conformation of the glycosyl acceptor exclusively the desired disaccharides are obtained as a single anomer.

The fully protected HLGAG oligosaccharides are assembled by coupling a disaccharide donor to an acceptor that may be a disaccharide or a longer oligosaccharide. The synthesis of the growing oligosaccharide chain relies on the formation of β-(1→4) uronic acid linkages and makes use of a C2 participating group to install this linkage with complete stereoselectivity.

Synthesis of Glucosamine Building Blocks of the Present Invention via a Common Precursor The first challenge to be tackled in trying to reduce to practice the general approach to HLGAG synthesis was the procurement of large amounts of differentially protected monosaccharide building blocks. In order to access large quantities of all monosaccharides, a convergent synthesis from inexpensive starting materials was needed that might be performed on large scale with a minimal number of chromatographic purification steps. While a host of synthetic methods for the preparation of glucosamine donors has been explored previously (J. Debenham, R. Rodebaugh, B. Fraser-Reid, *Liebigs Ann./Recueil* 1997, 791–802.), we focused on an approach that allowed access to all glucosamine monomers from a limited number of advanced intermediates. To identify the building blocks most suitable for installation of the desired α-glucosamine linkage, different anomeric leaving groups replaced an anomeric silyl ether during the late stages of the synthesis.

Figure 3:
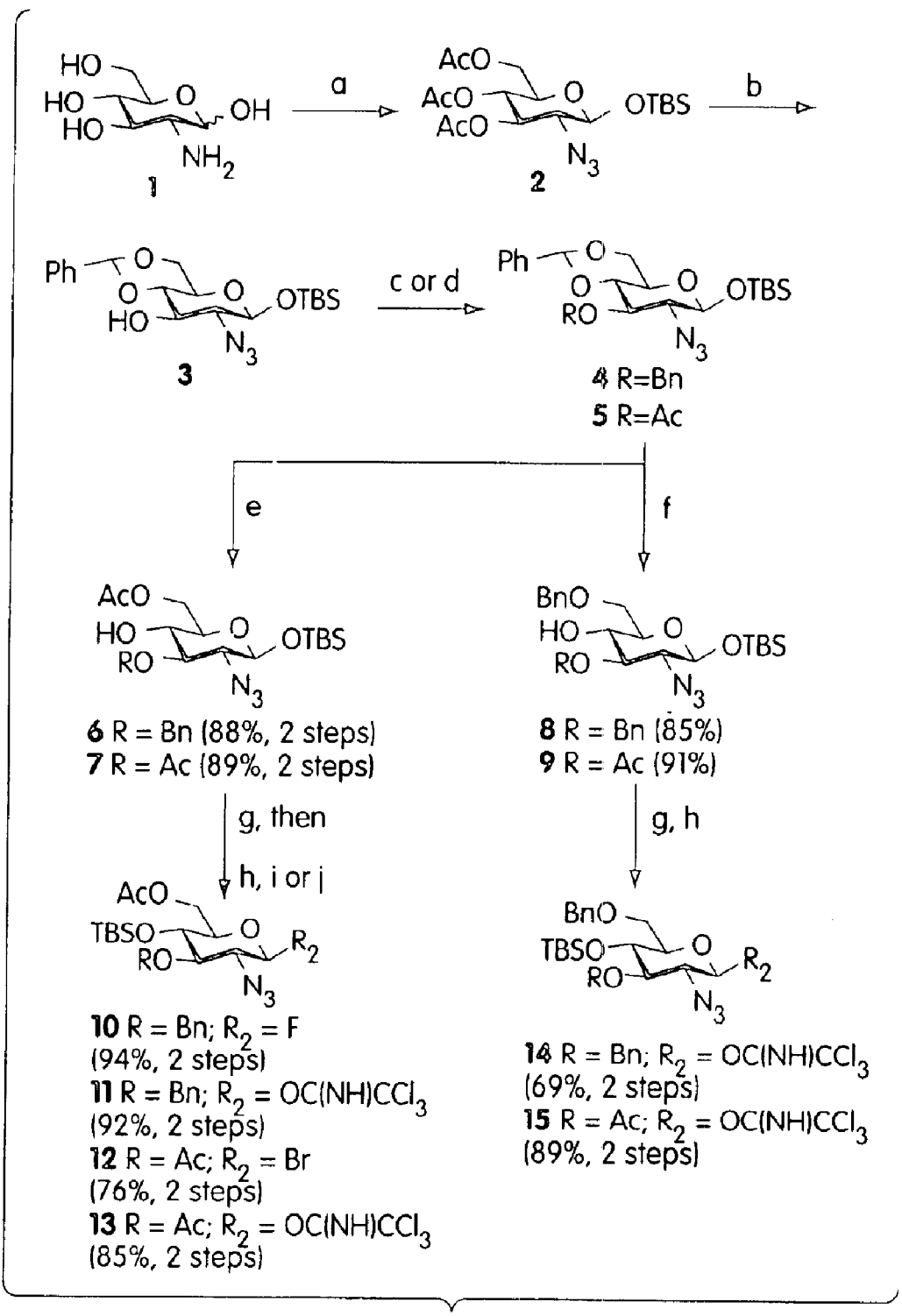
FIG. 3 depicts the syntheses of various monosaccharide building blocks of the present invention.

A set of glucosamine building blocks was prepared from glucosamine 1. See FIG. 3. Conversion of the 2-amino group into the corresponding azide, necessary for α-selective glycosylations, was followed by acetylation and anomeric silylation to afford crystalline 2 in 72% yield over four steps. P. B. Alper, S.-C. Hung, C.-H. Wong, *Tetrahedron Lett.* 1996, 37, 6029–6032; A. Vasella, C. Witzig, J.-L. Chiara, M. Martin-Lomas *Helv. Chim. Acta*, 1991, 74, 2073–2077; and B. La Ferla, L. Lay, M. Guerrini, L. Poletti, L. Panza, G. Russo, *Tetrahedron* 1999, 55, 9867–9880. Deacetylation and installation of the 4,6-benzylidene acetal furnished common precursor 3. Benzylation of the 3-hydroxyl to fashion 4 or acetylation to afford 5 was followed by either removal of the 4,6-benzylidene protecting group and installation of 6-acetates, or selective opening of the benzylidene acetal to furnish 6-benzyl groups. These maneuvers provided access to the skeleton of four glucosamine building blocks containing 4-O-silyl ethers as temporary protecting groups. These TBS groups would later be removed during the preparation of oligosaccharides utilizing the disaccharide modules.

With the desired protecting group patterns in place, we turned our attention to the installation of different anomeric leaving groups. Less reactive glycosyl fluoride 10, glycosyl bromide 12, exhibiting intermediate reactivity, and highly reactive glycosyl trichloroacetimidates 11 and 13–15 were prepared for couplings with uronic acid acceptors.

Figure 4:
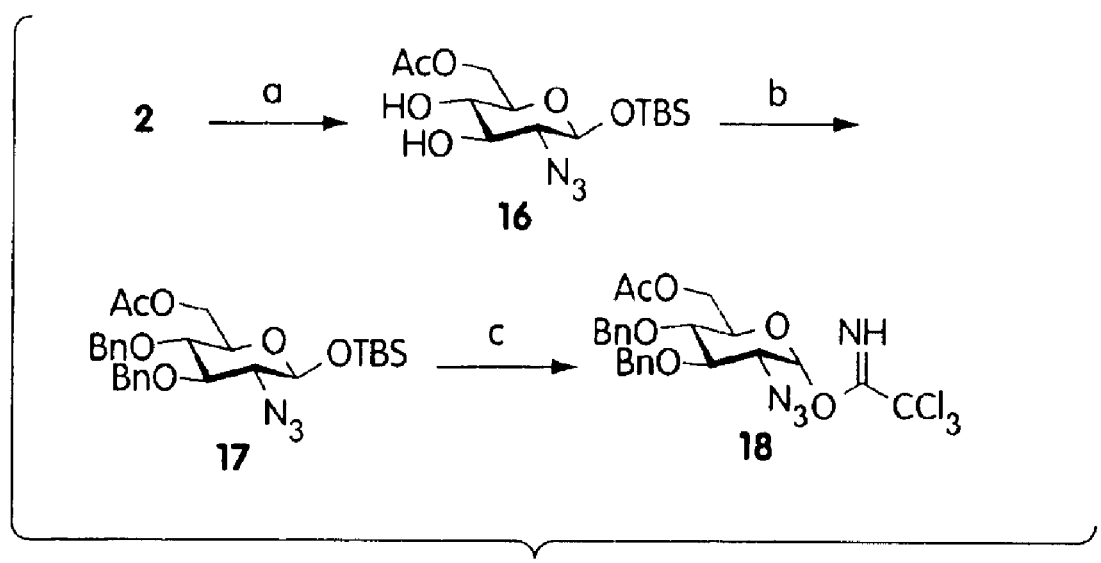
FIG. 4 depicts the syntheses of various monosaccharide building blocks of the present invention.

In addition to glucosamine units that act as acceptors during oligosaccharide formation, glucosamine 'cap' monosaccharides were required to mark the non-reducing end of the target oligosaccharide. A 4-O-benzyl ether was readily introduced by dibenzylation of diol 16 followed by transformation into glycosyl trichloroacetimidate 18. See FIG. 4. Using this approach, three other cap building blocks with different permutations of acetates and benzyl groups were prepared.

Figure 5:
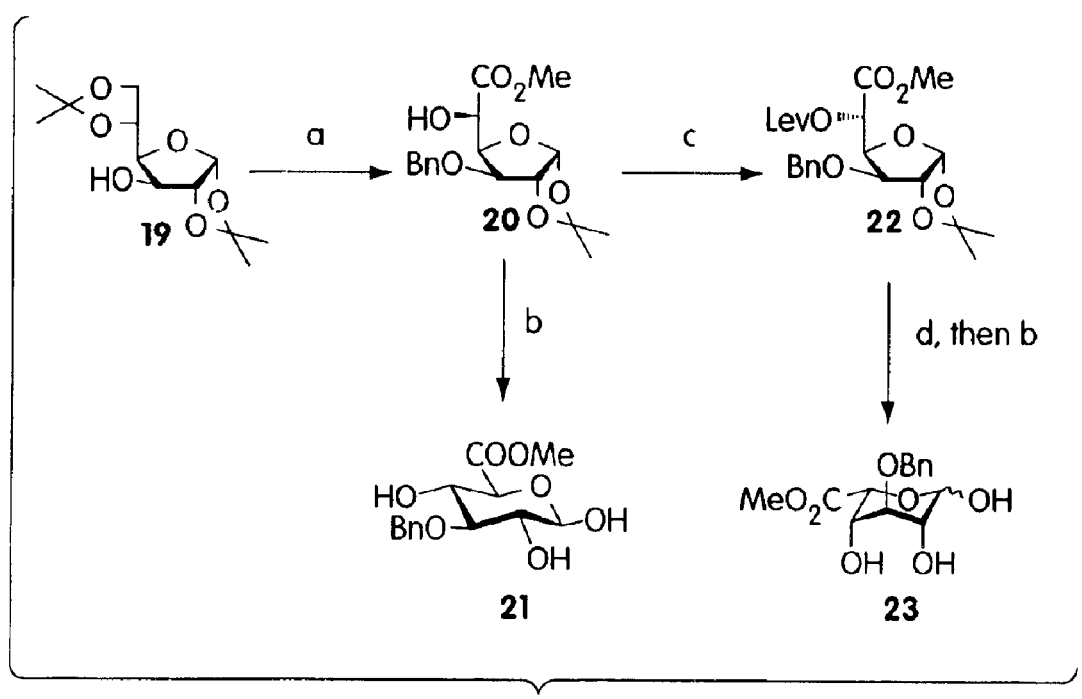
FIG. 5 depicts the syntheses of various monosaccharide building blocks of the present invention.

Preparation of Glucuronic Acid and Iduronic Acid Building Blocks of the Present Invention After reducing to practice our routes for the preparation of glucosamine building blocks, a reliable route for the synthesis of glucuronic and iduronic acid units was developed. Traditionally, the preparation of iduronic acid building blocks has been particularly difficult because no direct precursor may be obtained from natural sources. J. M. J. Tronchet, G. Zosimo-Landolfo, F. Villedon-Denaide, M. Balkadjian, D. Cabrini, F. Barbalat-Rey *J. Carbohydr. Chem.* 1990, 9, 823–835; and A. B. Smith, R. A. Rivero, K. J. Hale, H. A. Vaccaro *J. Am. Chem. Soc.* 1991, 113, 2092–2112. Efficiency, scalability and the avoidance of excessive chromatography was mandatory for the procurement of large amounts of these starting materials. Under this premise, we developed a route to differentially protected glucuronic acid and iduronic acid monosaccharides via a common intermediate. See FIG. 5. Commercially available diacetone glucose 19 was converted to crystalline glucuronic acid furanoside 20 via an eight step procedure that was easily scalable to 100 g starting material and did not require any purification. N. M. Spijker, P. Westerduin, C. A. A. van Boeckel *Tetrahedron*, 1992, 48, 6297–6316; and W. M. Macindoe, H. Ijima, Y. Nakahara, T. Ogawa *Carbohydr. Res.* 1995, 269, 227–257. Access to iduronic acid furanoside 22 was readily achieved by inversion of the C5 stereocenter of the triflate derived from 20. Treatment of 20 and 22 with trifluoroacetic acid resulted in deprotection and formation of the uronic acid pyranosides 21 and 23.

Synthesis of Disaccharide Building Blocks of the Present Invention—The Concept of "Locked" Acceptors The installation of α-glucosamine linkages, which are ubiquitous in nature (see A. Varki *Glycobiology* 1993, 3, 97–130.), is a central feature of the modular approach to glycosaminoglycans described here. Specifically, we have discovered that 1,2-cyclic acetal protecting groups may be used to constrain the conformation of glucuronic acid acceptors and to lock the C4 hydroxyl group in an axial position. This conformational locking of the glycosyl acceptor results in completely selective reactions with glycosidating agents, affording disaccharide modules that previously were only available as anomeric mixtures.

Figure 6:
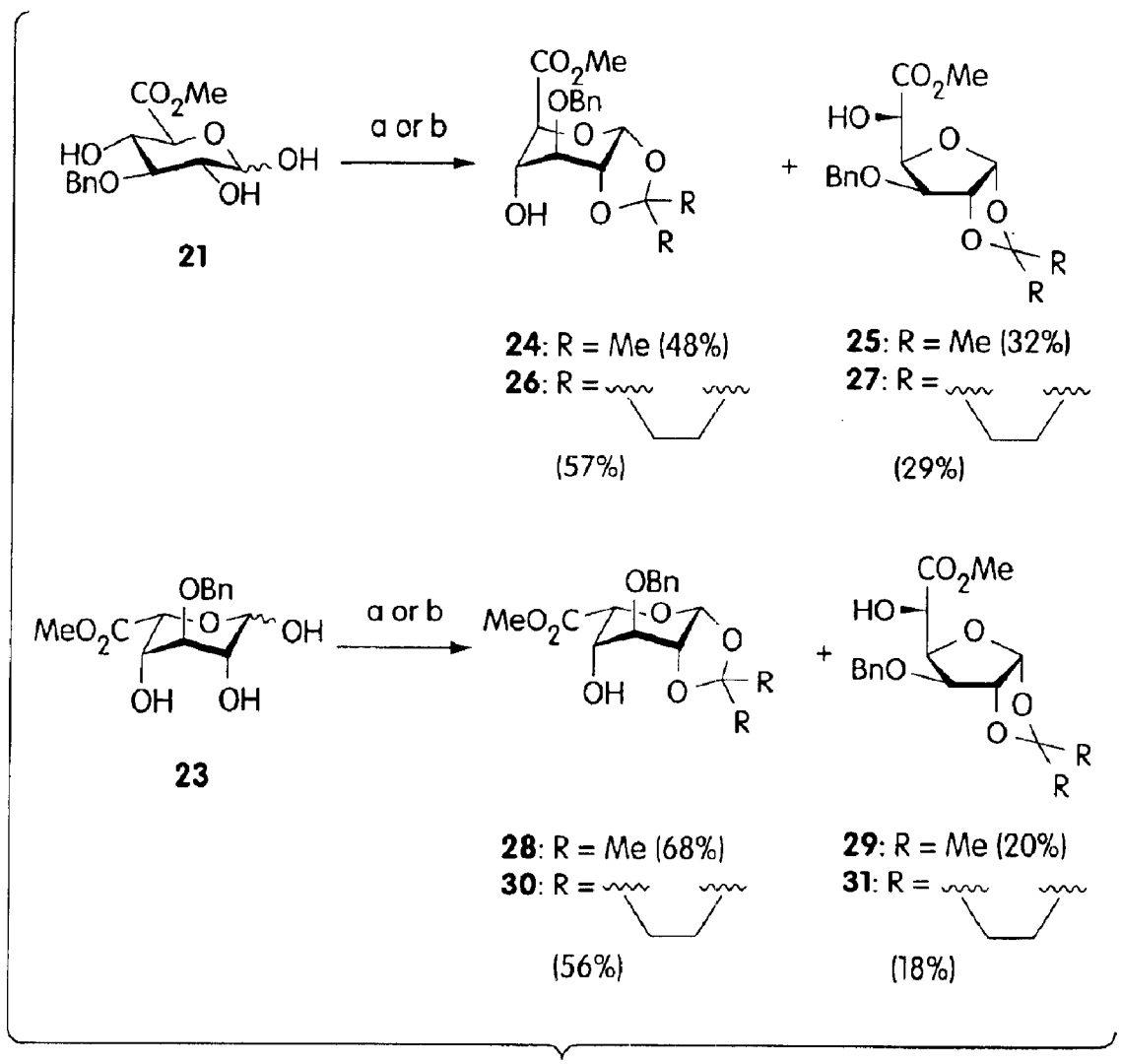
FIG. 6 depicts the syntheses of various monosaccharide building blocks of the present invention.

Differentially protected uronic acid monomers (24, 26, 28, 30) were prepared from triols 21 and 23 by formation of isoproylidene acetals (J. Celas, D. Horton *Heterocycles*, 1981, 16, 1587–1601; and M. L. Wolfrom, A. B. Diwadkar, J. Gelas, D. Horton *Carbohydr. Res.* 1974, 35, 87–96) or cyclopentylidene acetals (J. M. J. Tronchet, G. Zosimo-Landolfo, F. Villedon-Denaide, M. Balkadjian, D. Cabrini, F. Barbalat-Rey *J. Carbohydr. Chem.* 1990, 9, 823–835; and A. B. Smith, R. A. Rivero, K. J. Hale, H. A. Vaccaro *J. Am. Chem. Soc.* 1991, 113, 2092–2112) via reaction with 2-methoxypropene or methoxycyclopentene under kinetic control. See FIG. 6. In addition to the desired compounds, the corresponding furanosides (25, 27, 29, 31) were obtained and were resubmitted to 1,2 acetal formation after cleavage of the acetal protective group.

Figure 7:
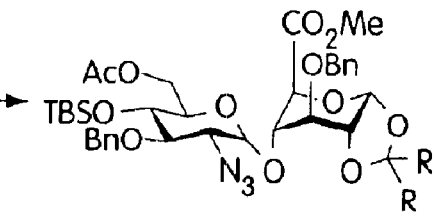
FIG. 7 depicts the synthesis of certain glucuronic acid disaccharides of the present invention using "locked" uronic acid acceptors.
Figure 7:
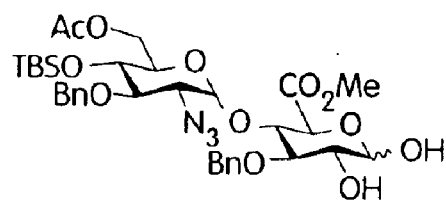
Figure 7:
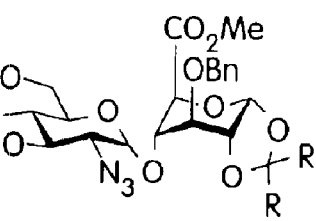
Figure 7:
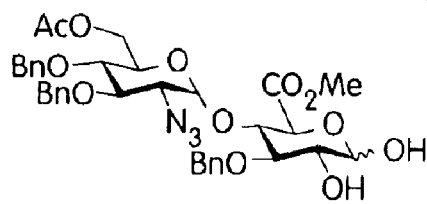
Figure 8:
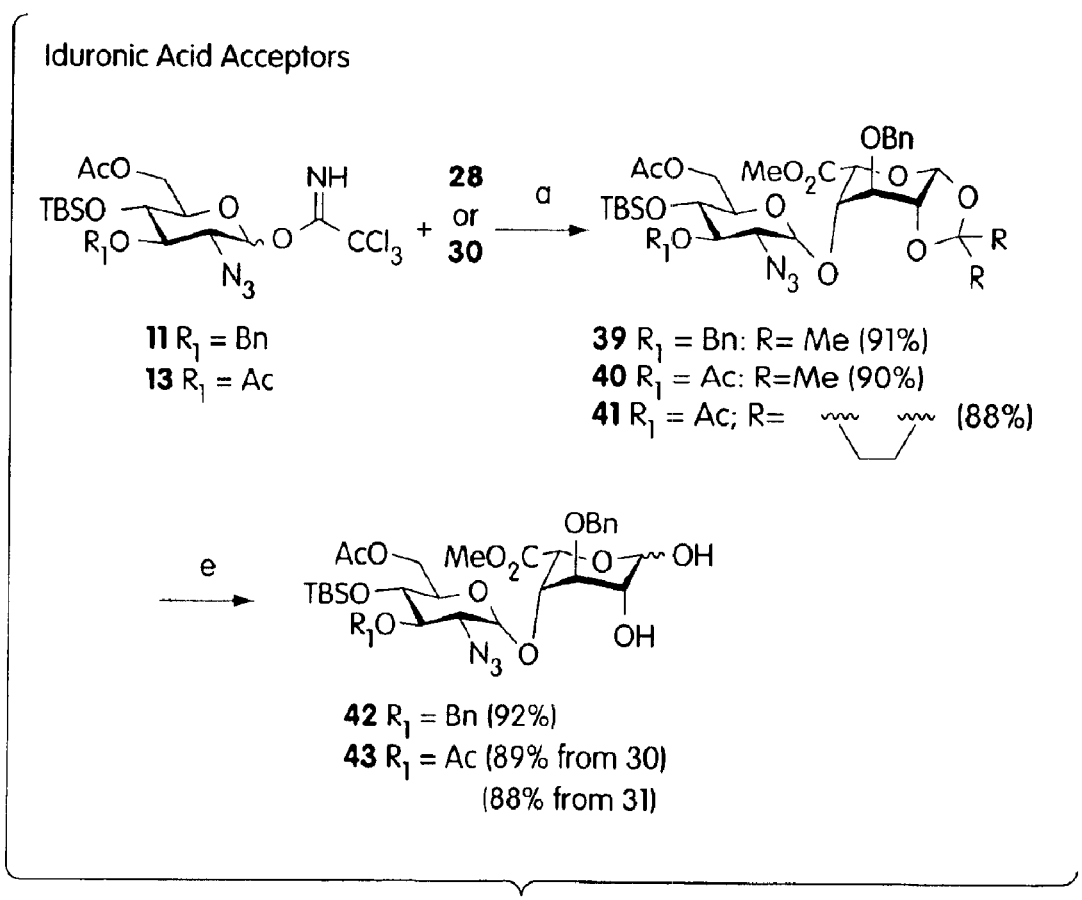
FIG. 8 depicts the synthesis of certain iduronic acid disaccharides of the present invention using "locked" uronic acid acceptors.

Union of glycosyl trichloroacetimidate and glycosyl fluoride glucosamine building blocks with glucuronic and iduronic acid glycosyl acceptors resulted exclusively in the formation of α-linked disaccharides in good yield. See FIG. 7. Notably, the identities of the cyclic protecting group (isopropylidene or cyclopentylidene) and anomeric leaving group did not influence the selectivity of the coupling reaction. The complete α-selectivity of the coupling reactions greatly simplified access to disaccharide modules for heparin assembly and purification of the reaction products. In addition to their use as molecular locks, 1,2-acetals are convenient for differential protection of monosaccharides and were applied to iduronic acid acceptors. Coupling of glycosyl donors 18 and 38 with iduronic acid acceptors 28 and 30 furnished disaccharides 39–41. After the cyclic acetal protecting groups served their purpose they were readily removed to yield disaccharide diols 34, 37, 42, and 43. See FIG. 8.

Figure 9:
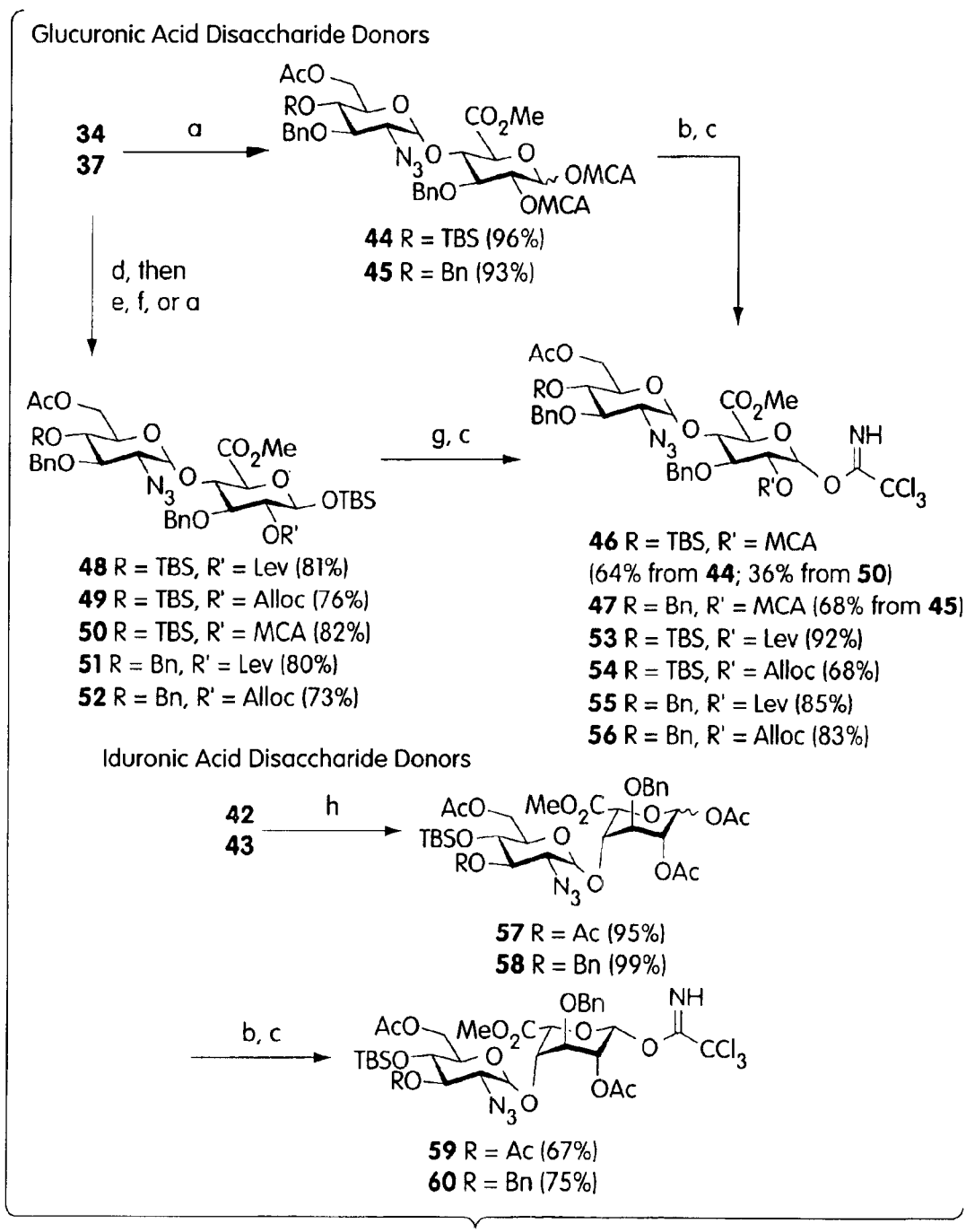
FIG. 9 depicts the synthesis of certain glucuronic acid disaccharide donors of the present invention.

Subsequent Modification at the Disaccharide Level. After the α-glucosamine linkages had been stereoselectively formed, the resulting disaccharides had to be converted into competent glycosyl donors and C2 participating groups had to be introduced in the uronic acid portion. In light of uronic acid C2 hydroxyl or sulfate groups, participating protective groups orthogonal to acetates were needed. Levulinoyl groups (Lev) (N. M. Spijker, P. Westerduin, C. A. A. van Boeckel *Tetrahedron*, 1992, 48, 6297–6316; and W. M. Macindoe, H. Ijima, Y. Nakahara, T. Ogawa *Carbohydr. Res.* 1995, 269, 227–257), allyloxycarbonate groups (Alloc) (E. Gentil, M. Potier, P. Boullanger, G. Descotes *Carbohydr. Res.* 1990, 197, 75–91; and T. M. Slaghek, Y. Nakahara, T. Ogawa, J. P. Kamerling, J. F. G. Vliegenthart *Carbohydr. Res.* 1994, 255, 61–85), and monochloroacetate groups (MCA) (C.-H. Wong, X.-S. Ye, Z. Zhang *J. Am. Chem. Soc.* 1998, 120, 7137–7138; and S. Canevari, D. Colombo, F. Compostella, L. Panza, F. Ronchetti, G. Russo, L. Toma *Tetrahedron* 1999, 55, 1469–1478) were installed in a variety of disaccharides to be replaced by permanent benzyl ether protection when desired. The selective introduction of 2-hydroxyl protective groups was accomplished via two different routes. See FIG. 9. Diacetylation of disaccharide diols 34 and 37 and selective cleavage of the anomeric MCA group was followed by conversion to the corresponding glycosyl trichloroacetimidates 46 and 47. D. Tailler. J.-C. Jacquinet, J.-M. Beau *J. Chem. Soc., Chem. Commun.* 1994, 1827–1828; and B. Ernst, G. W. Hart, P. Sinaÿ, *Carbohydrates in Chemistry and Biology*, Vol. 1, ch. 2, Wiley-VCH, Weinheim, 2000. Iduronic acid containing disaccharide modules 59 and 60 were prepared from 42 and 43. For protecting groups that did not allow for selective anomeric cleavage, anomeric silylation (Z.-H. Jiang, R. R. Schmidt *Liebigs Ann. Chem.* 1994, 645–651), protection of the 2-hydroxyl group, desilylation and preparation of the glycosyl trichloroacetimidates furnished disaccharide modules 53–56.

Figure 10:
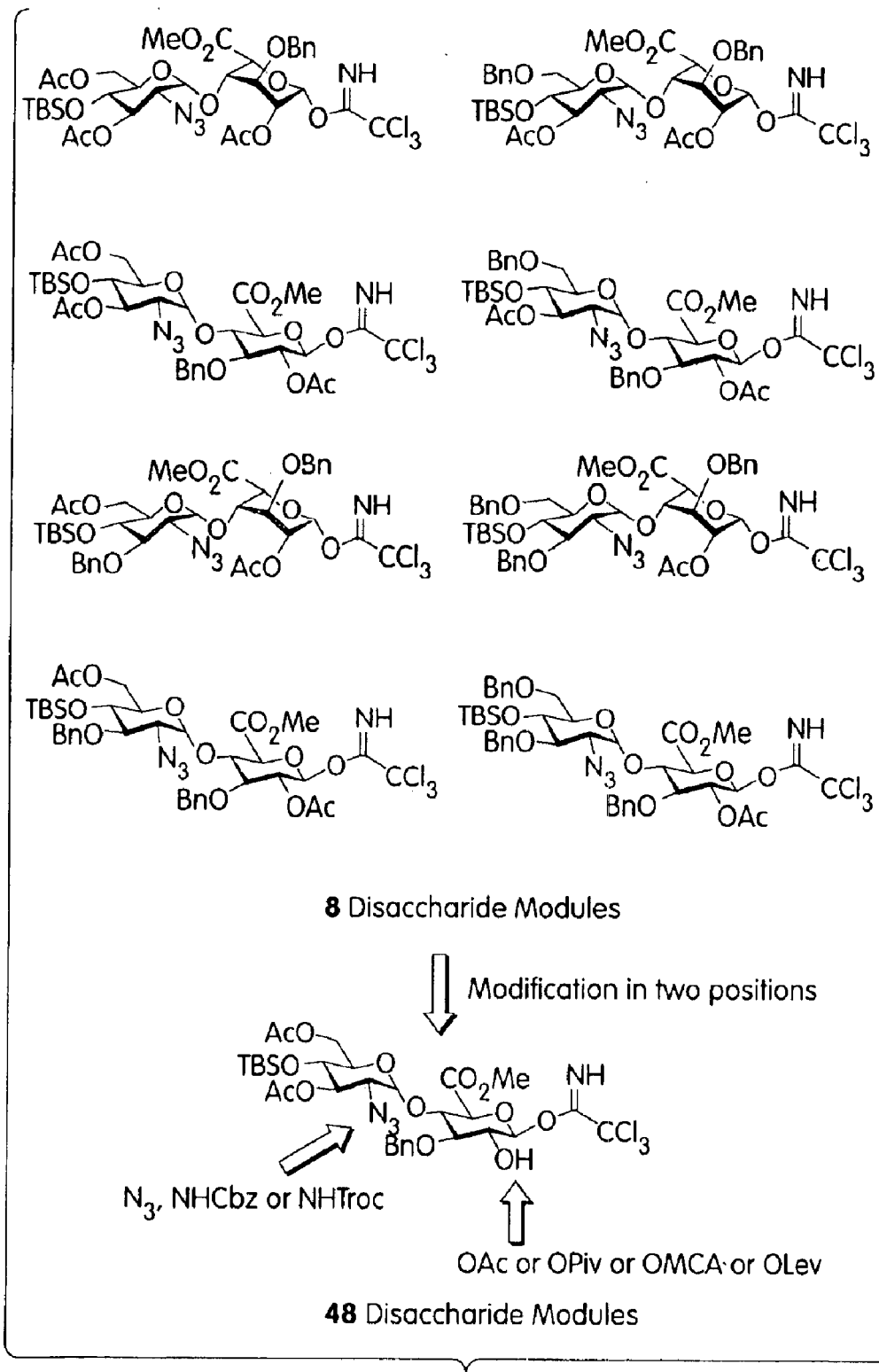
FIG. 10 depicts various disaccharide modules of the present invention that may be exploited to prepare heparin sequences according to methods of the present invention.

The second site for modification of the glucosamine residues, as mandated by the naturally occurring glycosaminoglycans structures, is the C2 amine moiety. Free amines, acetylated amines and sulfated amines are found in heparin glycosaminoglycans. Therefore, different protecting groups such as azides, Cbz or Troc groups were introduced to differentiate this site. The modification of the eight disaccharide building blocks gives rise to a total of 48 differentially protected disaccharide modules. See FIG. 10.

Figure 11:
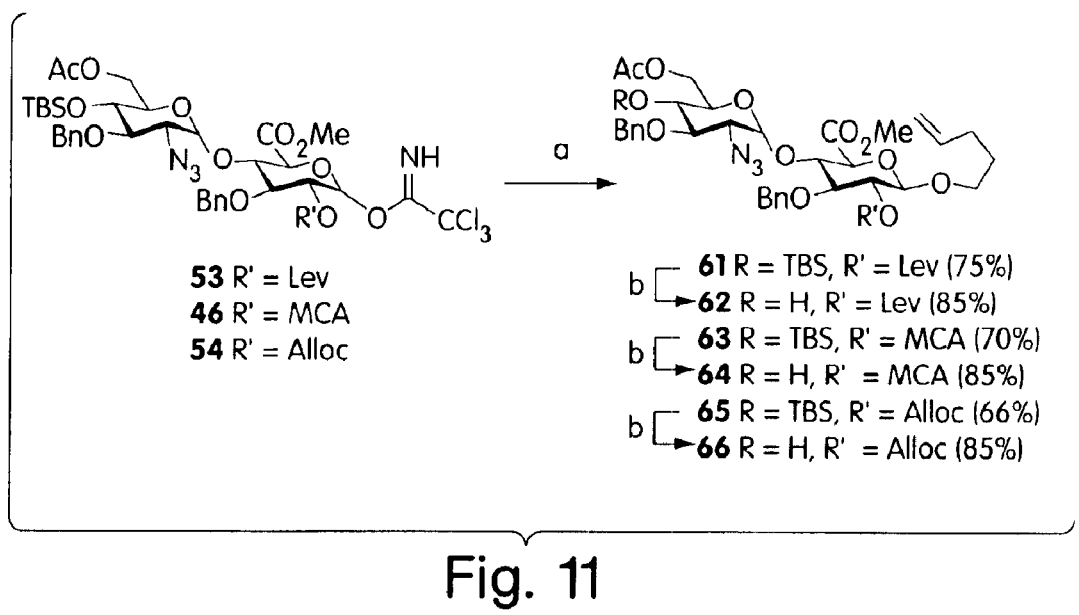
FIG. 11 depicts the synthesis of various reducing-end disaccharides of the present invention.
Figure 12:
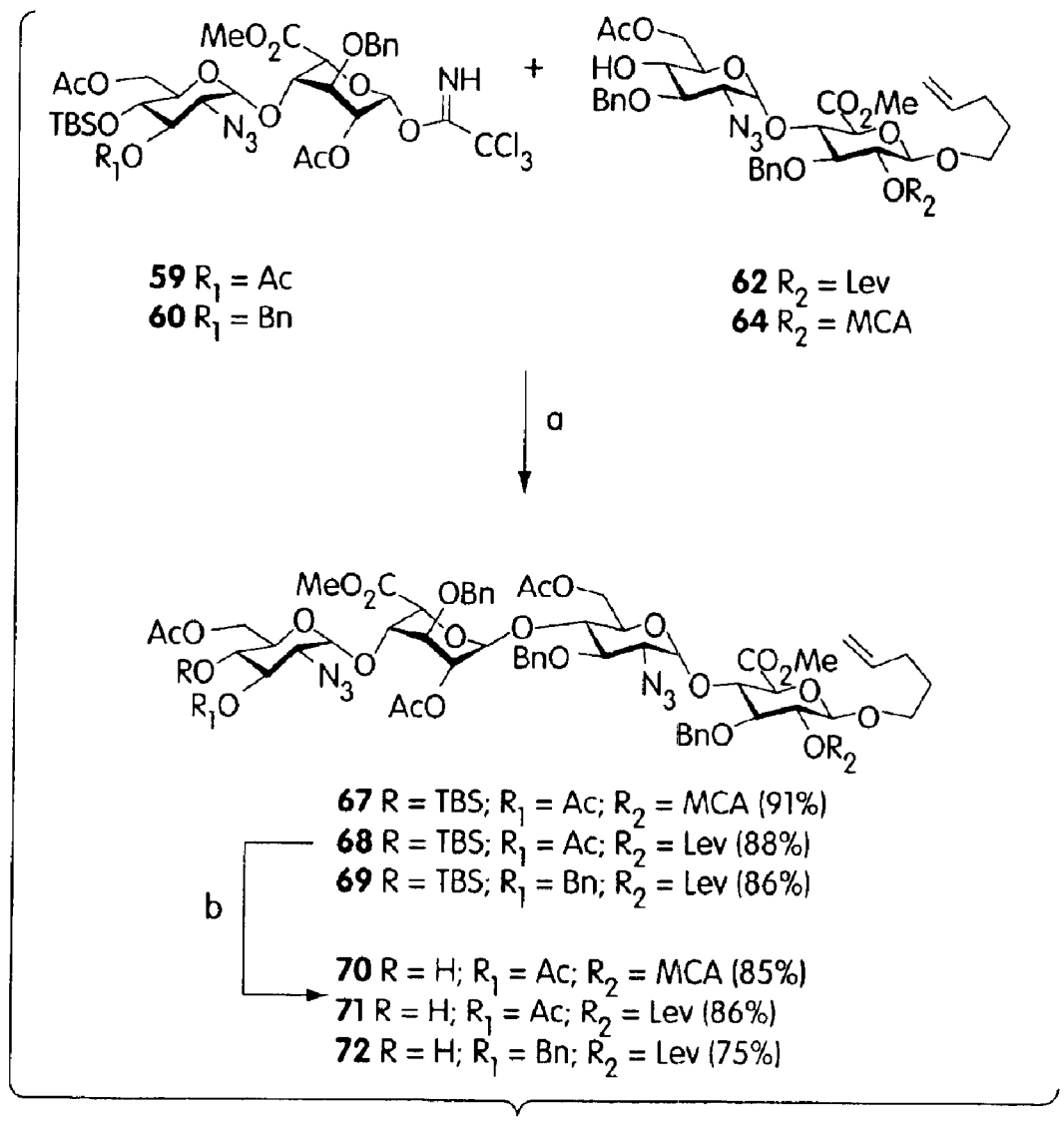
FIG. 12 depicts the synthesis of various tetrasaccharides according to the methods of the present invention.

Synthesis of Defined Heparin Oligosaccharide Sequences According to the Methods of the Present Invention Oligosaccharide Assembly Using Disaccharide Modules. Access to the aforementioned set of 48 different disaccharide building blocks provided the foundation for the preparation of defined heparin structures via a relatively simple two-step coupling-deprotection sequence. In general, a disaccharide glycosyl donor may be coupled with a designated hydroxyl group of a disaccharide acceptor to form a new glycosidic linkage therebetween. Different reducing end modules were created by reaction of any disaccharide with 1-pentenol. See FIG. 11. For example, coupling of disaccharide donors 59 and 60 with reducing end modules 62 and 64 furnished tetrasaccharides 67–69 in excellent yield. Removal of the 4-silyl ether protecting group in the tetrasaccharides rendered them acceptors for further elongation (70–72). See FIG. 12.

Figure 13:
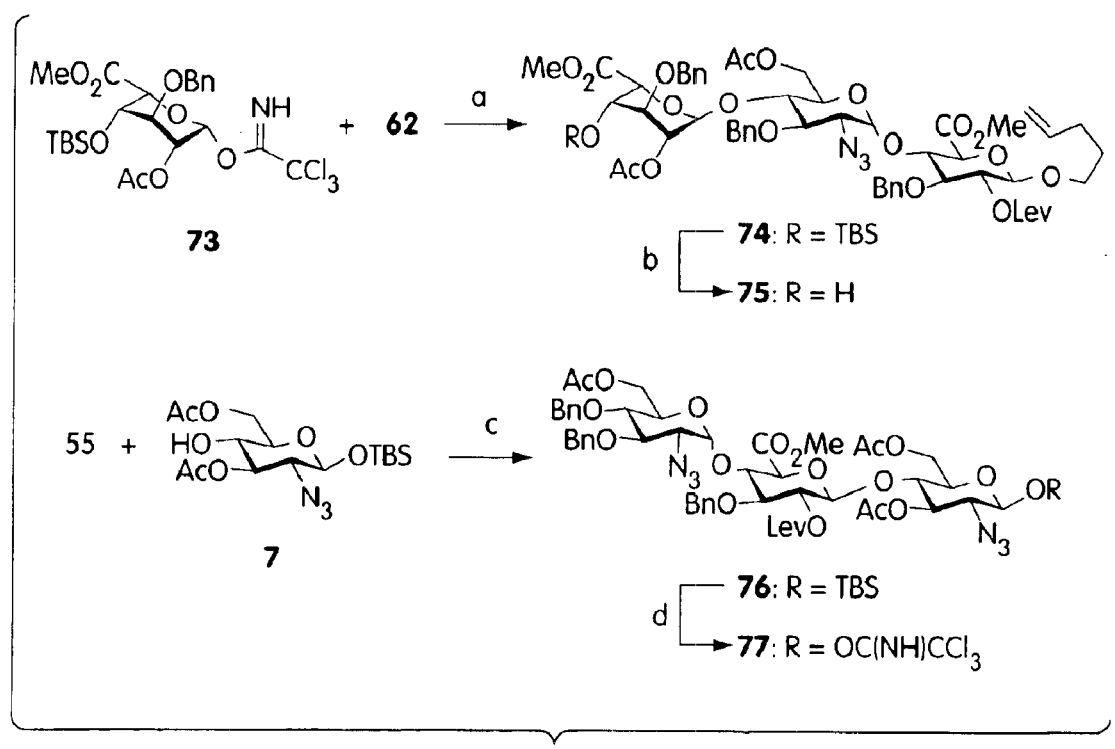
FIG. 13 depicts the synthesis of various trisaccharides according to the methods of the present invention.
Figure 14:
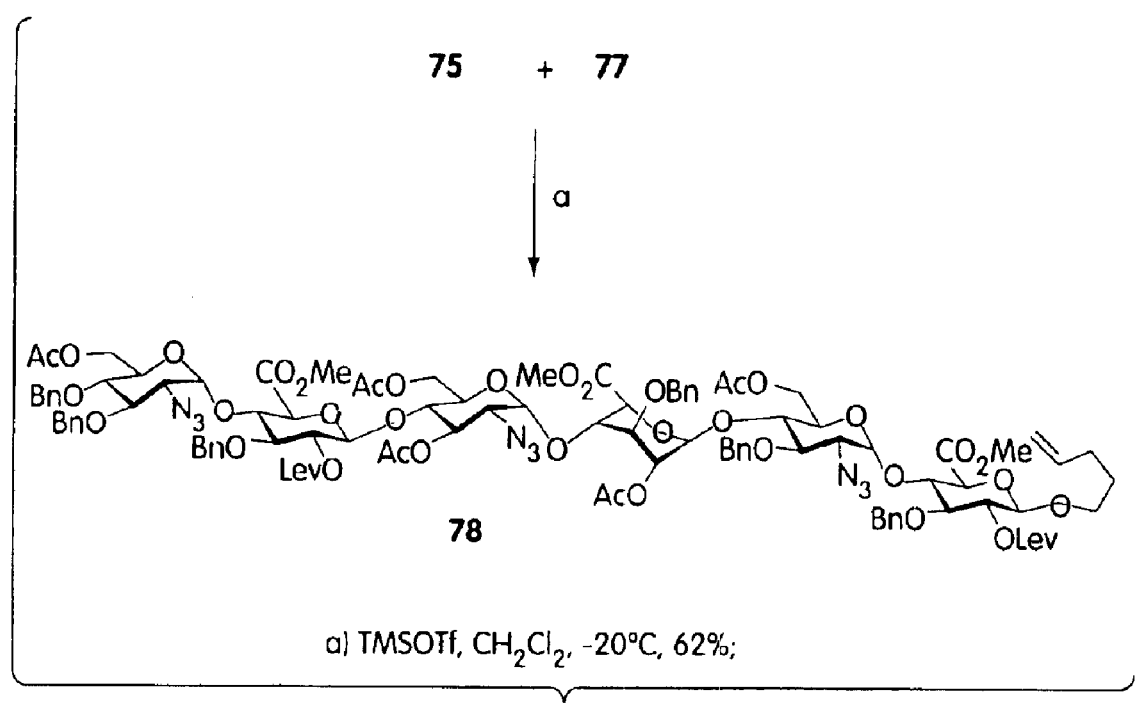
FIG. 14 depicts the synthesis of a hexasaccharide according to the methods of the present invention.

Oligosaccharide Assembly Using Trisaccharide Modules. The modular synthesis of heparin oligosaccharides was further expanded to use trisaccharide modules, allowing access to all possible structures. The overall strategy remained efficient as the linkage between glucosamine and iduronic acid can be established selectively and in high yield. See FIG. 2. Trisaccharide modules were readily prepared from the set of disaccharides as exemplified by the synthesis of 74 and 76. See FIG. 13. The resulting trisaccharides could be readily converted into acceptors (e.g. 75) or donors (e.g. 76) for the modular assembly of oligosaccharides. For example, this approach was successfully applied to the synthesis of hexasaccharide 78 by coupling trisaccharide modules 75 and 77 in 62% yield. See FIG. 14.

Figure 15:
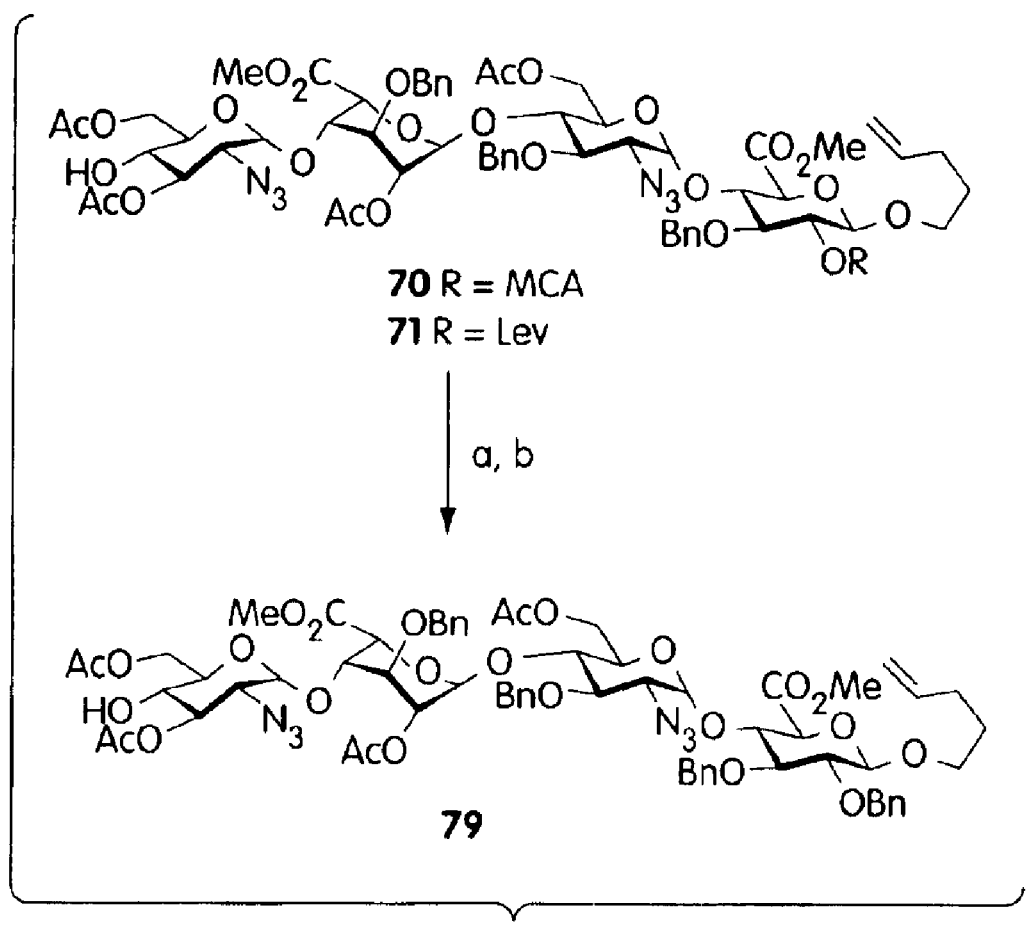
FIG. 15 depicts protecting group modification of a tetrasaccharide according to the methods of the present invention.
Figure 16:
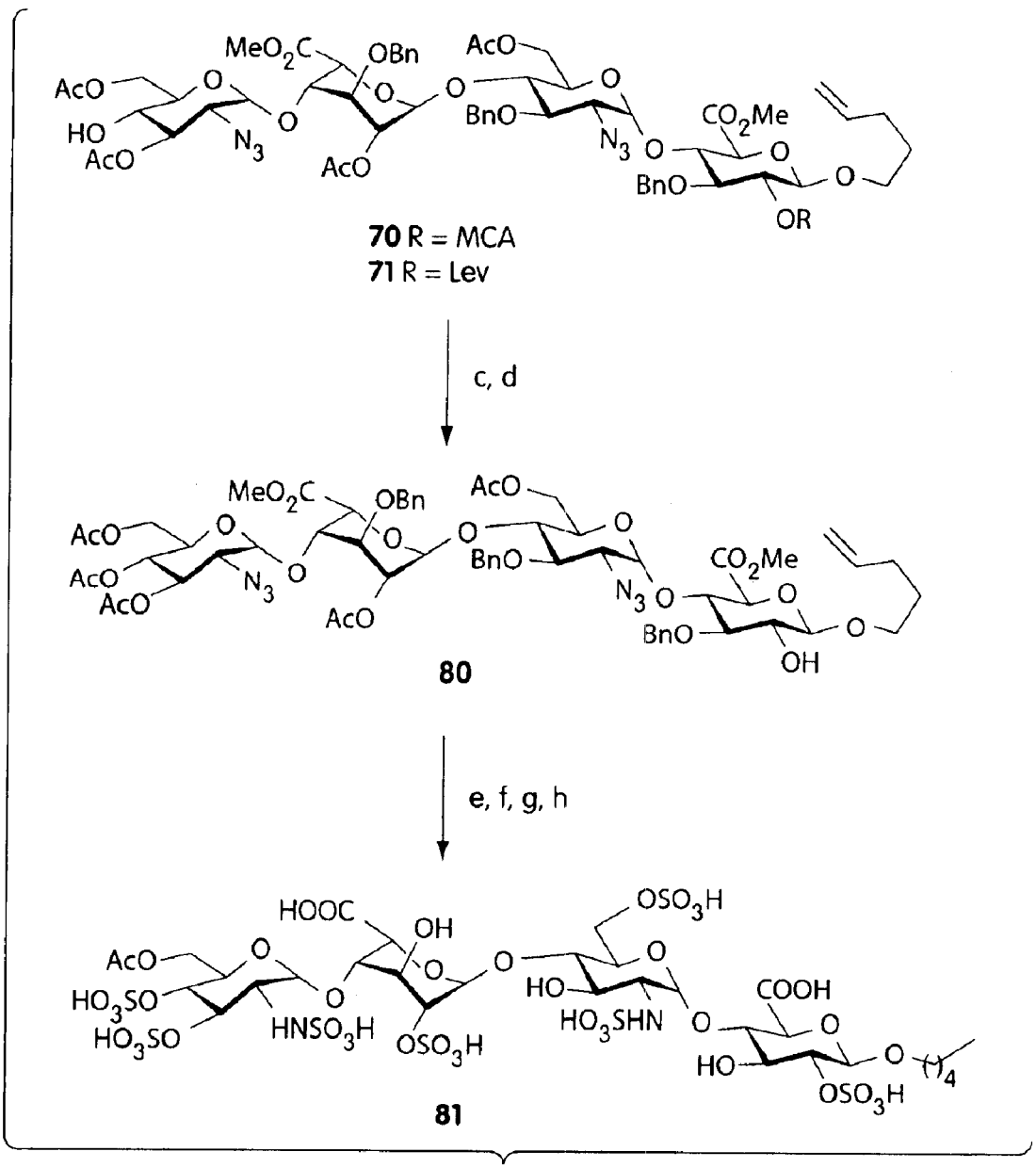
FIG. 16 depicts protecting group modification, sulfation, and the final deprotection of a tetrasaccharide according to the methods of the present invention.

Sulfation and Final Deprotection. Following the elongation steps, a series of deprotection and sulfation steps were carried out to create the desired fully functionalized glycsoaminoglycan by installation of the desired sulfation patterns. From the outset of the synthesis, acetates marked positions to be sulfated, whereas benzyl ethers designated free hydroxyl groups. C. Tabeur, J.-M. Mallet, F. Bono, J.-M. Herbert, M. Petitou, P. Sinaÿ *Bioorg. Med. Chem.* 1999, 7, 2003–2012. The placement of different C2 protection groups on uronic acid donors was illustrated. Tetrasaccharides 70 and 71 served to demonstrate the final deprotection and sulfation steps. See FIGS. 15 and 16. Selective removal of the monochloroacetate group in 70 (V. Pozsgay *J. Org. Chem* 1998, 63, 5983–5999) and levulinoyl group in 71 (N. Spijker, P. Westerduin, C. A. A. van Boeckel *Tetrahedron* 1992, 30, 6297–6316; and W. M. Macindoe, H. Ijima, Y. Nakahara, T. Ogawa *Carbohydr. Res.* 1995, 269, 227–257.) was achieved in high yield. Permanent protection of the free hydroxyl group was readily accomplished by benzylation to furnish 72. Alternatively, after saponification of 73, the unprotected hydroxyl groups could be sulfated by reaction with $Et_3NSO_3$. C. Tabeur, J.-M. Mallet, F. Bono, J.-M. Herbert, M. Petitou, P. Sinaÿ *Bioorg. Med. Chem.* 1999, 7, 2003–2012. Cleavage of all benzyl ether protective groups and selective N-sulfation furnished fully functionalized heparin tetrasaccharide 74. C. Tabeur, J.-M. Mallet, F. Bono, J.-M. Herbert, M. Petitou, P. Sinaÿ *Bioorg. Med. Chem.* 1999, 7, 2003–2012.

Solid-Phase Synthesis of Defined Heparin Oligosaccharide Sequences According to the Methods of the Present Invention The preparation of structurally defined oligopeptides and oligonucleotides has benefited greatly from the feasibility of conducting their assembly on solid supports. The advantages of solid matrix based synthesis, in terms of allowing for an excess of reagents to be used and in their facilitation of purification, are now well appreciated. However, the level of complexity associated with the synthesis of oligosaccharides on a polymer support dwarfs that associated with the other two classes of repeating biooligomers. Over the past five years, various strategies and glycosylating agents have been employed in the solid-phase synthesis of oligosaccharides. While the number of couplings that may be carried on the solid support is limited, solid-phase synthesis holds particular potential with regard to the parallel or combinatorial synthesis of diverse sets of oligosaccharides.

Figure 17:
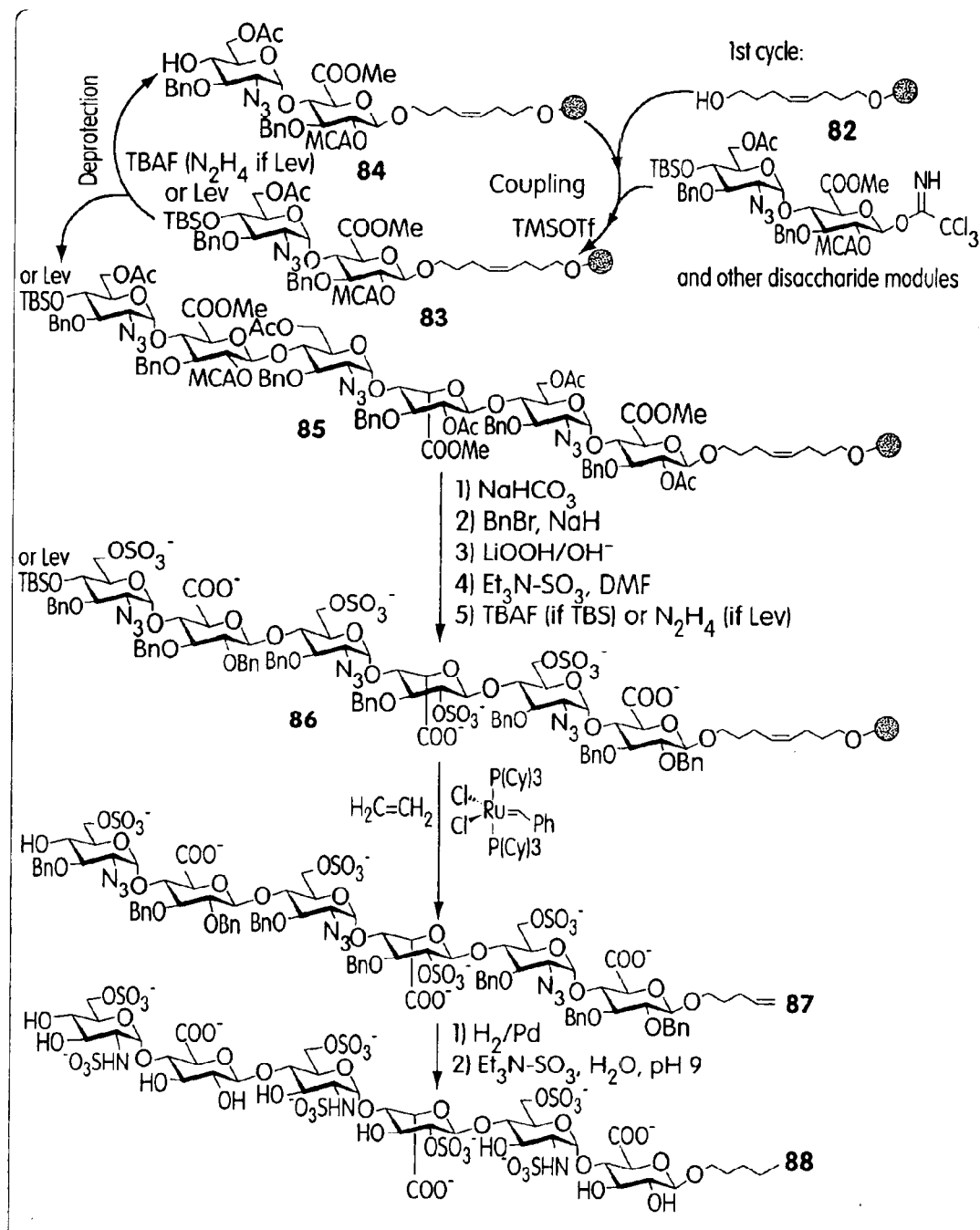
FIG. 17 depicts a solid-phase synthesis of various glycosaminoglycans according to the modular approach of the present invention.

The modular synthesis of heparin and other glycosaminoglycans was readily adapted to the solid phase assembly. Following the scheme developed by our own laboratory (Plante, O. J.; Palmacci, E. R.; Seeberger, P. H.; Automated Solid-Phase Synthesis of Oligosaccharides; *Science* 2001, 291, 1523–1527) a polystyrene-bound octenediol linker 82 connects the first disaccharide to the solid support to form 83. See FIG. 17. Upon removal of the C4 protective group, the sugar may function again as a glycosyl acceptor in further couplings until a hexasaccharide of the type 85 is formed. Deprotection and partial sulfation follow solution phase protocols to fashion 86. Cleavage from the solid support was accomplished by cross-methathesis, yielding hexasaccharide 87 that is then fully deprotected and sulfated to furnish hexasaccharide 88. Accordingly, the solid phase method allows for the rapid assembly of defined heparin oligosaccharides, as well as the parallel synthesis of heparin libraries on solid support.

Methods of Administration of Compounds of the Present Invention

Certain of the glycosaminoglycans of the instant invention will be useful in therapeutic applications, e.g., for treating or preventing a variety of diseases, including cancer, inflammation, and diseases caused or exacerbated by platelet aggregation or angiogenic activity.

Administration of the glycosaminoglycans synthesized via the methods of the invention will typically be by routes appropriate for glycosaminoglycan or other carbohydrate compositions, and generally includes systemic administration, such as by injection. For example, intravenous injection, such as continuous injection over long time periods, can be carried out. Also contemplated are introduction into the vascular system through intraluminal administration or by adventitial administration using osmotic pumps or implants. Typical implants contain biodegradable materials, such as collagen, polylactate, polylactate/polyglycoside mixtures and the like. These may be formulated as patches or beads. Typical dosage ranges may be in the range of 0.1–10 mg/kg/hr on a constant basis over a period of 5–30 days, preferably 7–14, days.

Other acceptable modes of administration include subcutaneous injection, e.g., transmembrane or transdermal or other topical administration for localized injury. Localized administration through a continuous release device, such as a supporting matrix, perhaps included in a vascular graft material, can be useful where the location of the trauma is accessible.

Formulations suitable for the foregoing modes of administration are known in the art, and a suitable compendium of formulations is found in Remington's Pharmaceutical Sciences, Mack Publishing Company, Easton, Pa., latest edition.

The glycosaminoglycans may also be labeled using typical methods, such as radiolabeling, fluorescent labeling, chromophores or enzymes, enabling assays of the amount of such compounds in a biological sample following its administration.

Definitions

For convenience, before further description of the present invention, certain terms employed in the specification, examples, and appended claims are collected here.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above, or from a Lewis base. Electrophilic moieties useful in the method of the present invention include halides and sulfonates.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "catalytic amount" is recognized in the art and means a substoichiometric amount of a reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The terms "arylalkyl" and "aralkyl", as used herein, refer to an alkyl group substituted with an aryl group. Likewise, the terms "heteroarylalkyl" and "heteroaralkyl", as used herein, refer to an alkyl group substituted with a heteroaryl group.

The terms "alkenyl" and "alkynyl" refer to unsaturated aliphatic groups analogous in length and possible substitution to the alkyls described above, but that comprise a double or triple bond, respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

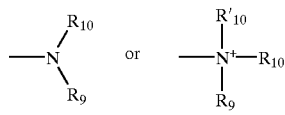

wherein $R_9$, $R_{10}$ and $R'_{10}$ each independently represent a group permitted by the rules of valence.

The term "acylamino" is art-recognized and refers to a moiety that can be represented by the general formula:

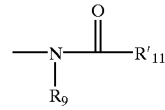

wherein $R_9$ is as defined above, and $R'_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

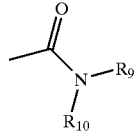

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

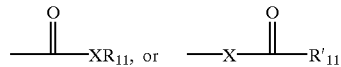

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'_{11}$ represents a hydrogen, an alkyl, an alkenyl or —(CH$_2$)$_m$—R$_8$, where m and R$_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group.

Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

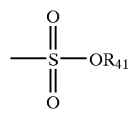

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

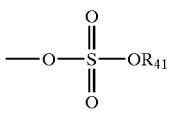

in which $R_{41}$ is as defined above.

The term "sulfonylamino" is art recognized and includes a moiety that can be represented by the general formula:

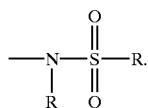

The term "sulfamoyl" is art-recognized and includes a moiety that can be represented by the general formula:

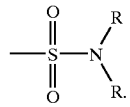

The term "sulfonyl", as used herein, refers to a moiety that can be represented by the general formula:

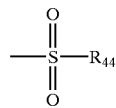

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

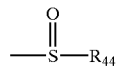

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dielectric constant ($\epsilon$) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred solvents are DMF, DME, NMP, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover.

Certain Compounds of the Present Invention

In certain embodiments, the present invention relates to a disaccharide selected from the group consisting of:

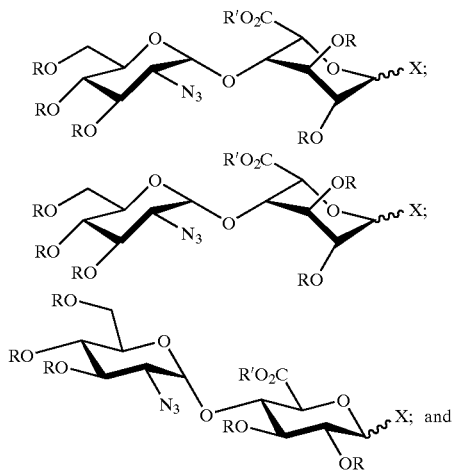

-continued

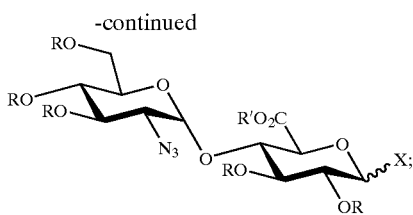

wherein

X represents independently for each occurrence hydroxyl, acyloxy, silyloxy, halide, alkylthio, arylthio, alkoxy, aryloxy, or —OC(NH)CCl$_3$;

R represents independently for each occurrence H, alkyl, aryl, arylalkyl, heteroarylalkyl, silyl, acyl, alkenyloxycarbonyl, or aralkyloxycarbonyl; and R' represents independently for each occurrence H, alkyl, aryl, arylalkyl, or heteroarylalkyl.

In certain embodiments, the present invention relates to a disaccharide as defined above, wherein X represents fluoro, bromo, 4-pentenyloxy or —OC(NH)CCl$_3$.

In certain embodiments, the present invention relates to a disaccharide as defined above, wherein R' represents independently for each occurrence alkyl.

In certain embodiments, the present invention relates to a disaccharide as defined above, wherein X represents fluoro, bromo, 4-pentenyloxy or —OC(NH)CCl$_3$; and R' represents independently for each occurrence alkyl.

In certain embodiments, the present invention relates to a disaccharide selected from the group consisting of:

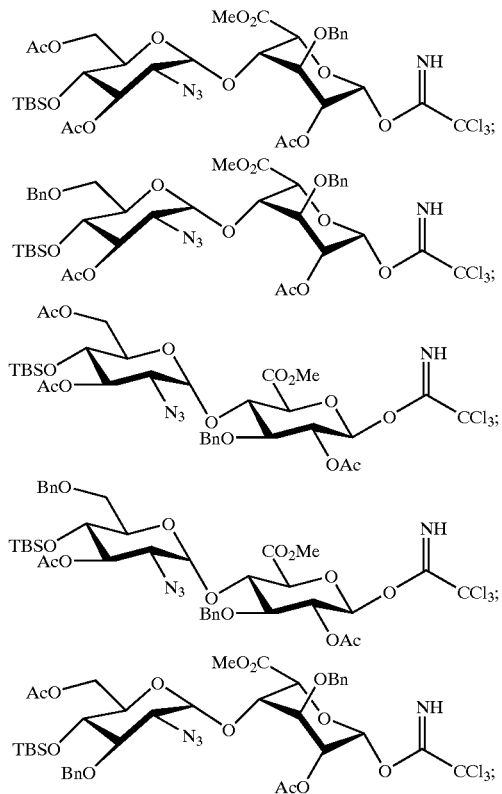

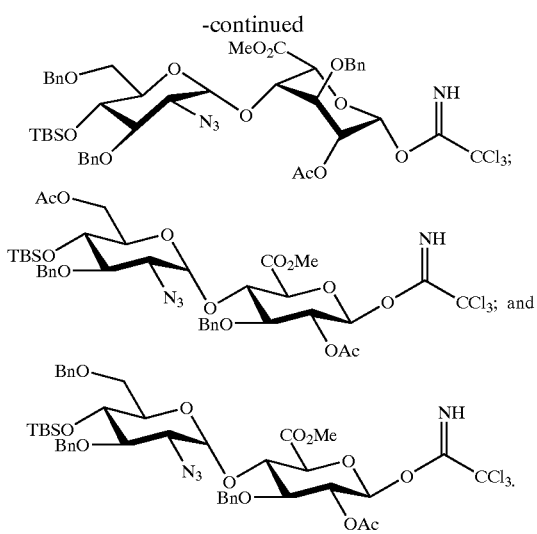

In certain embodiments, the present invention relates to a trisaccharide selected from the group consisting of:

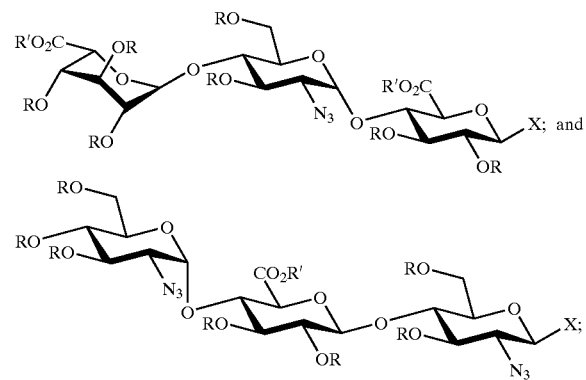

wherein

X represents independently for each occurrence hydroxyl, acyloxy, silyloxy, halide, alkylthio, arylthio, alkoxy, aryloxy, or —OC(NH)CCl₃;

R represents independently for each occurrence H, alkyl, aryl, arylalkyl, heteroarylalkyl, silyl, acyl, alkenyloxycarbonyl, or aralkyloxycarbonyl; and R' represents independently for each occurrence H, alkyl, aryl, arylalkyl, or heteroarylalkyl.

In certain embodiments, the present invention relates to a trisaccharide as defined above, wherein X represents fluoro, bromo, 4-pentenyloxy or —OC(NH)CCl₃.

In certain embodiments, the present invention relates to a trisaccharide as defined above, wherein R' represents independently for each occurrence alkyl.

In certain embodiments, the present invention relates to a trisaccharide as defined above, wherein X represents fluoro, bromo, 4-pentenyloxy or —OC(NH)CCl₃; and R' represents independently for each occurrence alkyl.

In certain embodiments, the present invention relates to a trisaccharide selected from the group consisting of:

wherein
X is silyloxy or —OC(NH)CCl₃; and
R is H or silyloxy.

Certain Methods of the Present Invention

In certain embodiments, the present invention relates to a method of preparing a glycosaminoglycan, comprising the step of reacting a first mono-, di- or tri-saccharide, comprising an activated anomeric carbon, with a second mono-, di- or tri-saccharide, comprising a hydroxyl or amino group, to form an oligosaccharide, comprising a glycosidic linkage between said anomeric carbon of said first mono-, di- or tri-saccharide and said hydroxyl or amino group of said second mono-, di- or tri-saccharide.

In certain embodiments, the present invention relates to the aforementioned method of preparing a glycosaminoglycan, wherein the first mono-, di- or tri-saccharide is not identical to the second mono-, di- or tri-saccharide.

In certain embodiments, the present invention relates to the aforementioned method of preparing a glycosaminoglycan, wherein neither the first mono-, di- or tri-saccharide nor the second mono-, di- or tri-saccharide is covalently linked to a solid support.

In certain embodiments, the present invention relates to the aforementioned method of preparing a glycosaminoglycan, wherein the first first mono-, di- or tri-saccharide or the second mono-, di- or tri-saccharide is covalently linked to a solid support.

In certain embodiments, the present invention relates to the aforementioned method of preparing a glycosaminoglycan, further comprising the step of cleaving said covalent linkage between said oligosaccharide and said solid support with an alkene metathesis catalyst and an alkene.

In certain embodiments, the present invention relates to the aforementioned method of preparing a glycosaminoglycan, further comprising the step of sulfating a hydroxyl or amino moiety of said oligosaccharide.

In certain embodiments, the present invention relates to the aforementioned method of preparing a glycosaminoglycan, further comprising the step of removing a hydroxyl or amino protecting group from said oligosaccharide by hydrogenolysis.

In certain embodiments, the present invention relates to a method of preparing an oligosaccharide comprising an α-glucosamine glycosidic linkage, comprising the step of reacting a uronic acid glycopyranosyl acceptor, comprising a hydroxyl group at C4 and a cyclic acetal comprising C1 and C2, with a glycosyl donor, comprising an activated anomeric carbon and an azide functional group at C2, to form an oligosaccharide comprising an α-glycosidic linkage between said hydroxyl group of said uronic acid glycopyranosyl acceptor and said anomeric carbon of said glycosyl donor.

In certain embodiments, the present invention relates to the aforementioned method of preparing an oligosaccharide comprising an α-glucosamine glycosidic linkage, wherein said uronic acid glycopyranosyl acceptor is an iduronic acid glycopyranosyl acceptor.

In certain embodiments, the present invention relates to the aforementioned method of preparing an oligosaccharide comprising an α-glucosamine glycosidic linkage, wherein said uronic acid glycopyranosyl acceptor is a glucuronic acid glycopyranosyl acceptor.

In certain embodiments, the present invention relates to the aforementioned method of preparing an oligosaccharide comprising an α-glucosamine glycosidic linkage, wherein said glycosyl donor is a glycosyl fluoride or glycosyl trichloroacetimidate.

In certain embodiments, the present invention relates to the aforementioned method of preparing an oligosaccharide comprising an α-glucosamine glycosidic linkage, wherein said glycosyl donor is a glycosyl fluoride or glycosyl trichloroacetimidate.

In certain embodiments, the present invention relates to the aforementioned method of preparing an oligosaccharide comprising an α-glucosamine glycosidic linkage, wherein said cyclic acetal comprising C1 and C2 of said uronic acid glycopyranosyl acceptor is an isopropylidene acetal or a cyclopentylidene acetal.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infuslion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Overview of Strategies and Methods of Combinatorial Chemistry

In the current era of drug development, high throughput screening of thousands to millions of compounds plays a key role. High throughput screening generally incorporates automation and robotics to enable testing these thousands to millions of compounds in one or more bioassays in a relatively short period of time. This high capacity screening technique requires enormous amounts of "raw materials" having immense molecular diversity to fill available capacity. Accordingly, combinatorial chemistry will play a significant role in meeting this demand for new molecules for screening. Once "leads" are identified using high throughput screening techniques, combinatorial chemistry will be advantageously used to optimize these initial leads (which analogs/variants will be tested in the same high throughput screening assay(s) that identified the initial lead).

A combinatorial library for the purposes of the present invention is a mixture of chemically-related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Several challenges have to be met to prepare combinatorial carbohydrate libraries. Synthetic strategies in which either the glycosyl donor or the glycosyl acceptor is attached to the solid support will be employed. A wide variety of differentially protected monosaccharide building blocks have to be prepared. Efficient glycosylation reactions have to be employed. The resulting libraries can be screened for lectin binding while still on the solid support or after already being cleaved.

The problem of efficiently generating molecular diversity has been tremendously simplified by the advent of combinatorial chemistry. See, e.g., Thompson, L. A.; Ellman, J. A. *Chem. Rev.* 1996, 96, 555–600. This concept when combined with solid-phase synthesis presents a powerful technique for the rapid construction of structurally diverse libraries of compounds which may be screened against therapeutic targets. A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288, 514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize subfemtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging With Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In certain embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529–2531), orthogonality in synthesis is achieved by employing acid-labile protection for the coding strand and base-labile protection for the compound strand.

In an alternative approach (Nikolaiev et al. (1993) Pept Res 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995)

PNAS 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention may be further understood with reference to the following examples, which are presented for illustrative purposes only and which are non-limiting.

General Experimental Procedures

All chemicals used were reagent grade and used as supplied except where expressly noted. Anhydrous methanol (MeOH) and dimethylformamide (DMF) were purchased from Aldrich in SureSeal bottles. Dichloromethane ($CH_2Cl_2$), diethyl ether, toluene and tetrahydrofuran (THF) were purchased from J. T. Baker (Cycletainer™) and passed through a neutral alumina column prior to use. Pyridine, 2,4,6 collidine and acetonitrile ($CH_3CN$) were refluxed over calcium hydride and distilled prior to use. Analytical thin-layer chromatography was performed on E. Merck silica gel 60 $F_{254}$ plates (0.25 mm). Compounds were visualized by dipping the plates in a cerium sulfate-ammonium molybdate solution followed by heating. Liquid column chromatography was performed using forced flow of the indicated solvent on Silicycle 230–400 mesh (60 Å pore diameter) silica gel. $^1$H NMR spectra were obtained on a Varian VXR-500 (500 MHz) or a Varian-300 (300 MHz) spectrometer and are reported in parts per million ($\delta$) relative to $CHCl_3$ (7.27 ppm). Coupling constants (J) are reported in Hertz. $^{13}$C NMR spectra were obtained on a Varian VXR-500 (125 MHz) or a Varian-300 (75 MHz) spectrometer and are reported in $\delta$ relative to $CDCl_3$ (77.23 ppm) as an internal reference.

Specific Experimental Procedures 1,3,4,6-Tetra-O-acetyl-2-azido-2-deoxy-D-glucopyranose Preparation of $TfN_3$ Dichloromethane was added to a solution of $NaN_3$ (59.5 g, 0.92 mol) in water (150 mL) at 0° C. $CH_2Cl_2$ (250 mL). The mixture was stirred vigorously and treated with trifluoromethanesulfonic anhydride (31.0 mL, 0.19 mol) over a period of 3 h at 0° C. After the complete addition of trifluoromethanesulfonic anhydride, the reaction mixture was stirred at 0° C. for 2.5 h. The aqueous phase was extracted with $CH_2Cl_2$ (2×100 mL) and the combined organic layers washed with saturated $Na_2CO_3$ and saved for use in the next step. [Caution: $TfN_3$ is explosive when not in solution.]

To a solution of glucosamine hydrochloride 1 (20.0 g, 0.092 mol) in water (300 mL) was added $CuSO_4$ (140 mg, 0.88 mmol) and $K_2CO_3$ (19.2 g, 0.14 mol). Methanol (600 mL) was added to the reaction mixture followed by the addition of the $TfN_3$ solution. Methanol was added until the solution was homogeneous (~300 mL). The clear blue solution was allowed to stir for 24 h at room temperature. Glycine (70 g) was added and the reaction mixture was again allowed to stir for 24 h. The glycine was filtered off and the solvent was removed in vacuo to afford a brown oil. The oil was taken up in pyridine (95 mL), cooled to 0° C. and DMAP (~30 mg) and acetic anhydride (86 mL, 0.91 mol) were added. The solution was stirred for 12 h at room temperature. The reaction was quenched with saturated $NaHCO_3$ and the aqueous phase was extracted with $CH_2Cl_2$ (3×1000 mL). The organic phase was dried over $MgSO_4$, filtered and the solvent was removed in vacuo to yield a brown oil. Warm ethanol was added until the solution was homogeneous. The resulting solution was cooled to −20° C. and a white precipitate formed. Cold water was then added, the white precipitate was filtered and washed with water and cold ethanol to afford β-product (23.8 g, 0.063 mol, 68%) as a colorless solid. $^1$H-NMR (300 MHz, $CDCl_3$) δ 5.55 (d, J=8.6 Hz, 1H), 5.15–5.00 (m, 2H), 4.31 (dd, J=4.6, 12.5 Hz, 1H), 4.08 (dd, J=2.1, 12.5 Hz, 1H), 3.75 (ddd, J=2.1, 4.4, 6.3 Hz, 1H), 3.65–3.72 (m, 1H), 2.20 (s, 3H), 2.10 (s, 3H), 2.08 (s, 3H), 2.04 (s, 3H); IR (thin film) 2959, 2112, 1747 $cm^{-1}$. Flash chromatography of the mother liquor (Hexanes:EtOAc 7:3) afforded a colorless oil (mixture of α/β) (5.6 g, 0.015 mmol, 17%). The spectral data was in agreement with the reported data. (P. B. Alper, S.-C. Hung, C.-H. Wong, Tetrahedron Lett. 1996, 37, 6029–6032; A. Vasella, C. Witzig, J.-L. Chiara, M. Martin-Lomas, Helv. Chim. Acta 1991, 74, 2073–2077).

tert-Butyldimethylsilyl 3,4,6-tri-O-acetyl-2-azido-2-deoxy-β-D-glucopyranoside 2

1,3,4,6-Tetra-O-acetyl-2-azido-2-deoxy-D-glucopyranose (30.2 g, 80 mmol) was coevaporated twice with toluene and dissolved in THF and methanol (7:3, 300 mL). The solution was cooled to 0° C. and gaseous anhydrous ammonia was bubbled through at a modest rate. After 15 min, nitrogen was bubbled through the solution to remove excess ammonia and the solvent was removed in vacuo to afford a brown oil. The residue was coevaporated twice with toluene and dissolved in $CH_2Cl_2$ (150 mL). Imidazole (10.9 g, 160 mmol) and tert-butyldimethylsilyl chloride (13.3 g, 88 mmol) were added. After 2 h, the mixture was diluted with EtOAc, washed with water, 1 N HCl (2×) and water. The organic layer was dried over $MgSO_4$, filtered, and the solvent was removed in vacuo. Crystallization from ethanol afforded 2 (29.8 g, 67 mmol, 84%) as colorless crystals. $^1$H-NMR (300 MHz, $CDCl_3$) δ 5.00–4.90 (m, 2H), 4.63 (d, J=7.6 Hz, 1H), 4.20 (dd, J=5.9, 12.1 Hz, 1H), 4.09 (dd, J=2.6, 12.1 Hz, 1H), 3.70–3.64 (m, 1H), 3.48–3.40 (m, 1H), 2.10 (s, 3H), 2.08 (s, 3H), 2.00 (s, 3H), 0.95 (s, 9H), 0.15 (s, 6H). The spectral data was in agreement with the reported data. (W. Kinzy, R. R. Schmidt, Liebigs Ann. Chem. 1985, 1537–1545; for the procedure see: B. La Ferla, L. Lay, M. Guerrini, L. Poletti, L. Panza, G. Russo, Tetrahedron 1999, 55, 9867–9880).

tert-Butyldimethylsilyl 2-azido-4,6-O-benzylidene-2-deoxy-β-D-glucopyranoside 3 tert-Butyldimethylsilyl 3,4,6-tri-O-acetyl-2-azido-2-deoxy-β-D-glucopyranoside 2 (36.9 g; 82.8 mmol) was dissolved in methanol (300 mL) and NaOMe (25% in MeOH, 5.4 mL) was added. After 15 min, DOWEX-50 acidic resin was added and the mixture was stirred until the pH reached 6. The DOWEX resin was filtered off and the solvent was removed in vacuo to afford a yellow oil. The residue was coevaporated twice with acetonitrile and dissolved in acetonitrile (400 mL). Benzaldehyde dimethyl acetal (24.8 mL, 165 mmol) and p-toluenesulfonic acid monohydrate (400 mg, 2.1 mmol) were added. After stirring overnight at room temperature, triethylamine (5 mL) was added and the solvents evaporated. Flash chromatography on silica gel (Hexanes:EtOAc 95:5→9:1) afforded 3 (29.0 g, 71.2 mmol, 86%) as a colorless oil. $^1$H-NMR (300 MHz, CDCl$_3$) δ 7.55–7.45 (m, 2H), 7.45–7.38 (m, 3H), 5.52 (s, 1H), 4.65 (d, J=7.65 Hz, 1H), 4.29 (dd, J=4.9, 10.4 Hz, 1H), 3.77 (t, J=10.1 Hz, 1H), 3.60–3.30 (m, 4H), 2.91 (s, 1H), 1.00 (s, 9H), 0.19 (s, 6H). The spectral data was in agreement with the reported data. (C. Murakata, T. Ogawa, *Carbohydrate Res*. 1992, 234, 75–91).

tert-Butyldimethylsilyl 2-azido-3-O-benzyl-4,6-O-benzylidene-2-deoxy-β-D-glucopyranoside 4 tert-Butyldimethylsilyl 2-azido-4,6-O-benzylidene-2-deoxy-β-D-glucopyranoside 3 (28.1 g, 68.97 mmol) was dissolved in CH$_2$Cl$_2$ (250 mL). Powdered, freshly activated 4 Å molecular sieves (45 g) and benzyl bromide (20.5 mL, 172 mmol) were added and the mixture was stirred for 30 min. Silver(I) oxide (47 g, 203 mmol) was added and the reaction vessel was covered in aluminum foil to exclude light. After 8 h, the reaction mixture was filtered through Celite and the filtrate was concentrated in vacuo. Flash chromatography on silica (Hexanes:EtOAc 50:1) afforded 4 (32.6 g, 65.5 mmol, 95%) as a colorless solid. $^1$H NMR (300 MHz, CDCl$_3$) 7.60–7.28 (m, 10H), 5.51 (s, 1H), 4.98 (d, J=11.5 Hz, 1H), 4.84 (d, J=11.5 Hz, 1H), 4.63 (d, J=7.5 Hz, 1H), 4.33 (dd, J=5.0, 9.4 Hz, 1H), 3.89–3.73 (m, 2H), 3.60–3.35 (m, 3H), 0.98 (s, 9H), 0.17 (s, 6H). The spectral data was in agreement with the reported data. (C. Murakata, T. Ogawa, *Carbohydrate Res*. 1992, 234, 75–91).

tert-Butyldimethylsilyl 3-O-acetyl-2-azido-4,6-O-benzylidene-2-deoxy-β-D-glucopyranoside 5 tert-Butyldimethylsilyl 2-azido-4,6-O-benzylidene-2-deoxy-β-D-glucopyranoside 3 (9.5 g, 23.3 mmol) was dissolved in CH$_2$Cl$_2$ (150 mL) and pyridine (21 mL), DMAP (280 mg, 2.3 mmol) and acetic anhydride (10 mL, 106 mol) were added. The reaction mixture was stirred overnight, water was added and stirred for 1 h. The organic layer was extracted with water, 1 N HCl, water and saturated NaHCO$_3$. The organic phase was dried over MgSO$_4$, filtered and the solvent was removed in vacuo. Flash chromatography on silica gel (Hexanes:EtOAc 50:1→5:1) afforded 5 (9.96 g, 22.1 mmol, 95%) as a colorless crystalline solid. $[α]^{24}_D$: −72.1 (c 0.99, CH$_2$Cl$_2$); IR (thin film) 2111, 1751, 1370, 1222, 1099, 841 cm$^{-1}$; $^1$H-NMR (300 MHz, CDCl$_3$) δ 7.45–7.33 (m, 5H), 5.49 (s, 1H), 5.13 (dd, J=9.7, 9.9 Hz, 1H), 4.72 (d, J=7.6 Hz, 1H), 4.31 (dd, J=4.9, 10.5 Hz, 1H), 3.80 (dd, J=10.2, 10.3 Hz, 1H), 3.65 (dd, J=9.4, 9.5 Hz, 1H), 3.49 (ddd, J=4.9, 9.6, 9.6 Hz, 1H), 3.42 (dd, J=7.5, 10.1 Hz, 1H), 2.14 (s, 3H), 0.95 (s, 9H), 0.19 (s, 3H), 0.18 (s, 3H); $^{13}$C-NMR (75 MHz, CDCl$_3$) δ 169.9, 136.9, 129.3, 128.4, 126.3, 101.7, 97.8, 78.9, 71.1, 68.7, 67.4, 66.8, 25.8, 21.2, 18.2, −4.1, −4.9; FAB MS (C$_{21}$H$_{31}$N$_3$O$_6$Si) m/z (M$^+$) calcd 449.1982, obsd 449.1876.

Synthesis of 6-O-Acetyl Glucosamine Series:

tert-Butyldimethylsilyl 2-azido-3-O-benzyl-2-deoxy-β-D-glucopyranoside tert-Butyldimethylsilyl 2-azido-3-O-benzyl-4,6-O-benzylidene-2-deoxy-β-D-glucopyranoside 4 (32.6 g, 65.5 mmol) was dissolved in CH$_2$Cl$_2$ (1.5 L) and trifluoroacetic acid (60% aq., 54 mL) was added. The resulting mixture was stirred vigorously at room temperature for 8.5 h and saturated NaHCO$_3$ was added careflly. After phase separation, the aqueous layer was extracted with CH$_2$Cl$_2$. The combined organic layers were dried over NaSO$_4$, filtered and the solvents were removed in vacuo. Flash chromatography on silica (Hexanes:EtOAc 4:1→1:1) afforded 7 (25 g, 61 mmol, 92%) as a colorless oil. $[α]^{24}_D$: −30.4 (c 1.00, CH$_2$Cl$_2$); IR (thin film) 3415, 2110, 1361, 1079 cm$^{-1}$; $^1$H-NMR (300 MHz, CDCl$_3$) δ 7.44–7.30 (m, 5H), 4.97 (d, J=11.4 Hz, 1H), 4.72 (d, J=11.4 Hz, 1H), 4.58 (d, J=7.5 Hz, 1H), 3.84 (dd, J=3.7, 11.8 Hz, 1H), 3.75 (dd, J=4.8, 11.8 Hz, 1H), 3.59 (dd, J=8.7, 9.5 Hz, 1H), 3.36–3.26 (m, 2H), 3.22 (dd, J=8.6, 9.9 Hz, 1H), 0.96 (s, 9H), 0.19 (s, 3H), 0.18 (s, 3H); $^{13}$C-NMR (75 MHz, CDCl$_3$) δ 138.2, 128.9, 128.34, 128.26, 97.5, 82.5, 75.3, 75.2, 70.7, 68.5, 62.8, 25.8, 18.1, −4.0, −4.9; FAB MS (C$_{19}$H$_{31}$N$_3$O$_5$Si) m/z (M$^+$) calcd 409.2033, obsd 409.2029. The spectral data was in agreement with the reported data (A. G. M. Barrett, D. Pilipauskas, J. Org. Chem. 1991, 56, 2787–2800).

tert-Butyldimethylsilyl 3-O-acetyl-2-azido-2-deoxy-β-D-glucopyranoside tert-Butyldimethylsilyl 3-O-acetyl-2-azido-4,6-O-benzylidene-2-deoxy-β-D-glucopyranoside 5 (9.5 g, 21.1 mmol) was dissolved in CH$_2$Cl$_2$ (500 mL) and trifluoroacetic acid (60% aq., 17 mL) was added. The resulting mixture was stirred vigorously at room temperature overnight and saturated NaHCO$_3$ was added carefully. After phase separation, the aqueous layer was extracted with CH$_2$Cl$_2$. The combined organic layers were dried over Na$_2$SO$_4$, filtered and the solvents were removed in vacuo. Flash chromatography on silica gel (Hexanes:EtOAc 4:1→1:1) afforded product (7.25 g, 20 mmol, 95%) as a colorless solid. $[α]^{24}_D$: −26.4 (c 1.00, CH$_2$Cl$_2$); IR (thin film) 3387, 2112, 1748, 1254, cm$^{-1}$; $^1$H-NMR (500 MHz, CDCl$_3$) δ 4.77 (dd, J=9.2, 9.5 Hz, 1H), 4.64 (d, J=7.6 Hz, 1H), 3.90 (dd, J=3.7, 11.9 Hz, 1H), 3.81 (dd, J=4.9, 11.9 Hz, 1H), 3.66 (dd, J=9.5, 9.5 Hz, 1H), 3.41–3.36 (m, 1H), 3.34 (dd, J=7.6, 10.4 Hz, 1H), 3.08–2.92 (br s, 1H), 2.15–1.92 (br s, 1H), 2.19 (s, 3H), 0.94 (s, 9H), 0.174 (s, 3H), 0.168 (s, 3H); $^{13}$C-NMR (125 MHz, CDCl$_3$) δ 172.2, 97.2, 76.0, 75.8, 70.1, 66.2, 62.6, 25.7, 21.2, 18.1, −4.1, −5.0; FAB MS (C$_{14}$H$_{27}$N$_3$O$_6$Si) m/z (M$^+$) calcd 361.1669, obsd 361.1677.

tert-Butyldimethylsilyl 6-O-acetyl-2-azido-3-O-benzyl-2-deoxy-β-D-glucopyranoside 6

Acetyl chloride (4.5 mL, 63.3 mmol) was added dropwise to a solution of tert-butyldimethylsilyl 2-azido-3-O-benzyl-2-deoxy-β-D-glucopyranoside (25 g, 61 mmol) in 2,4,6-collidine (110 mL) under nitrogen at −40° C. After stirring at −40° C. overnight, water was added. The mixture was poured into EtOAc and extracted with 1 N HCl, brine and saturated NaHCO$_3$. The organic phase was dried over Na$_2$SO$_4$, filtered and the solvents were removed in vacuo to afford 6 (26.5 g, 58.7 mmol, 96%) as a colorless solid. $[α]^{24}_D$: −27.1 (c 1.00, CH$_2$Cl$_2$); IR (thin film) 3482, 2110, 1743, 1255 cm$^{-1}$; $^1$H-NMR (300 MHz, CDCl$_3$) δ 7.43–7.30 (m, 5H), 4.96 (d, J=11.4 Hz, 1H), 4.73 (d, J=11.4 Hz, 1H), 4.55 (d, J=7.6 Hz, 1H), 4.34–4.27 (m, 2H), 3.50–3.38 (m, 2H), 3.33 (dd, J=7.6, 9.9 Hz, 1H), 3.21 (dd, J=8.3, 9.9 Hz, 1H), 2.59–2.46 (br s, 1H), 2.09 (s, 3H), 0.96 (s, 9H), 0.18 (s, 6H); $^{13}$C-NMR (75 MHz, CDCl$_3$) δ 171.5, 138.1, 128.8, 128.31, 128.28, 97.4, 82.2, 75.3, 73.8, 70.3, 68.3, 63.5, 25.8, 21.1, 18.3, −4.1, −5.0; FAB MS (C$_{21}$H$_{33}$N$_3$O$_6$Si) m/z (M$^+$) calcd 451.2138, obsd 451.2135.

tert-Butyldimethylsilyl 3,6-di-O-acetyl-2-azido-2-deoxy-β-D-glucopyranoside 7

Acetyl chloride (1.5 mL, 21.1 mmol) was added slowly to a solution of tert-butyldimethylsilyl 3-O-acetyl-2-azido-2-deoxy-β-D-glucopyranoside (7.25 g, 20 mmol) in 2,4,6-collidine (47 mL) under nitrogen at −40° C. After stirring at −40° C. overnight, water was added. The mixture was poured into EtOAc and extracted with 1 N HCl, brine and saturated NaHCO$_3$. The organic phase was dried over Na$_2$SO$_4$, filtered and the solvents were removed in vacuo. Flash chromatography on silica gel (Hexanes:EtOAc 5:1→4:1) afforded 7 (7.59 g, 18.8 mmol, 94%) as a colorless solid. $[α]^{24}_D$: −31.6 (c 1.00, CH$_2$Cl$_2$); IR (thin film on NaCl)

3459, 2112, 1747, 1233, 1042, 841 cm$^{-1}$; $^1$H-NMR (300 MHz, CDCl$_3$) δ 4.81–4.74 (m, 1H), 4.62 (d, J=7.6 Hz, 1H), 4.37–4.31 (m, 2H), 3.75–3.46 (m, 2H), 3.53 (dd, J=7.7, 10.3 Hz, 1H), 3.13–3.09 (m, 1H), 2.18 (s, 3H), 2.10 (s, 3H), 0.94 (s, 9H), 0.17 (s, 6H); $^{13}$C-NMR (75 MHz, CDCl$_3$) δ 171.8, 171.5, 97.2, 75.5, 74.3, 69.8, 66.0, 63.4, 25.8, 21.2, 21.1, 18.2, −4.2, −5.0; FAB MS (C$_{16}$H$_{29}$N$_3$O$_7$Si) m/z (M$^+$) calcd 403.1775, obsd 403.1779.

tert-Butyldimethylsilyl 6-O-acetyl-2-azido-3-O-benzyl-4-O-tert-butyldimethylsilyl-2-deoxy-β-D-glucopyranoside tert-Butyldimethylsilyl trifluormethanesulfonate (3.4 mL, 14.8 mmol) was added to a solution of tert-butyldimethylsilyl 6-O-acetyl-2-azido-3-O-benzyl-2-deoxy-β-D-glucopyranoside 6 (5.15 g, 11.4 mmol) and 2,6-lutidine (3.3 mL, 28.3 mmol) in CH$_2$Cl$_2$ (50 mL) at −20° C. The reaction was allowed to warm to room temperature and stir for 1 h. The mixture was poured into EtOAc and the aqueous layer was extracted with 1 N HCl, brine and saturated NaHCO$_3$. The organic layer was dried over Na$_2$SO$_4$, filtered and the solvents were removed in vacuo. Flash chromatography on silica gel (Hexanes:EtOAc 199:1→98:2) afforded product (5.8 g, 10.3 mmol, 90%) as a colorless oil. [α]$^{24}_D$: +36.1 (c 1.00, CH$_2$Cl$_2$); IR (thin film) 2110, 1748, 1112 cm$^{-1}$; $^1$H-NMR (300 MHz, CDCl$_3$) δ 7.40–7.28 (m, 5H), 4.93 (d, J=11.1 Hz, 1H), 4.71 (d, J=11.1 Hz, 1H), 4.56 (d, J=7.6 Hz, 1H), 4.42 (dd, J=2.2, 11.6 Hz, 1H), 4.07 (dd, J=6.6, 11.6 Hz, 1H), 3.59 (dd, J=8.3, 9.5 Hz, 1H), 3.45 (ddd, J=2.2, 6.6, 9.5 Hz, 1H), 3.34 (dd, J=7.6, 9.9 Hz, 1H), 3.20 (dd, J=8.3, 9.9 Hz, 1H), 2.08 (s, 3H), 0.94 (s, 9H), 0.89 (s, 9H), 0.164 (s, 3H), 0.160 (s, 3H), 0.05 (s, 3H), 0.03 (s, 3H); $^{13}$C-NMR (75 MHz, CDCl$_3$) δ 170.8, 138.4, 128.5, 127.7, 127.6, 97.4, 83.0, 75.2, 74.6, 71.3, 69.2, 63.6, 26.1, 25.8, 21.1, 18.3, −3.5, −4.1, −4.6, −5.0; FAB MS (C$_{27}$H$_{47}$N$_3$O$_6$Si$_2$) m/z (M$^+$) calcd 565.3003, obsd 565.3011.

tert-Butyldimethylsilyl 3,6-di-O-acetyl-2-azido-4-O-tert-butyldimethylsilyl-2-deoxy-β-D-glucopyranoside tert-Butyldimethylsilyl trifluoromethanesulfonate (4.1 mL, 17.9 mmol) was added to a solution of tert-butyldimethylsilyl 3,6-di-O-acetyl-2-azido-2-deoxy-β-D-glucopyranoside 7 (4.70 g, 11.65 mmol) and 2,6-lutidine (3.5 mL, 30 mmol) in CH$_2$Cl$_2$ (25 mL) at −20° C. The reaction was allowed to warm to room temperature and stirred for 1 h. The mixture was poured into EtOAc and extracted with 1 N HCl, brine and saturated NaHCO$_3$. The organic layer was dried over Na$_2$SO$_4$, filtered and solvents removed in vacuo. Flash chromatography on silica gel (Hexanes:EtOAc 199:1→98:2) afforded product (5.61 g, 10.8 mmol, 93%) as a colorless oil. [α]$^{24}_D$: −3.1 (c 1.00, CH$_2$Cl$_2$); IR (thin film) 2111, 1750, 1363, 1221 cm$^{-1}$; $^1$H-NMR (300 MHz, CDCl$_3$) δ 4.87 (dd, J=8.8, 10.4 Hz, 1H), 4.63 (d, J=7.6 Hz, 1H), 4.39 (dd, J=2.2, 11.7 Hz, 1H), 4.08 (dd, J=6.2, 11.7 Hz, 1H), 3.67 (dd, J=9.1, 9.2 Hz, 1H), 3.54–3.46 (m, 1H), 3.27 (dd, J=7.6, 10.4 Hz, 1H), 2.14 (s, 3H), 2.08 (s, 3H), 0.92 (s, 9H), 0.83 (s, 9H), 0.15 (s, 3H), 0.14 (s, 3H), 0.05 (s, 3H), 0.04 (s, 3H); $^{13}$C-NMR (75 MHz, CDCl$_3$) δ 170.7, 169.9, 97.1, 74.6, 74.5, 69.6, 66.8, 63.1, 25.80, 25.75, 21.6, 21.1, 18.2, 18.1, −3.9, −4.3, −4.6, −5.0; FAB MS (C$_{22}$H$_{43}$N$_3$O$_7$Si$_2$) m/z (M$^+$) calcd 517.2639, obsd 517.2635.

Synthesis of 6-O-Benzyl Glucosamine Series:

tert-Butyldimethylsilyl 2-azido-3,6-di-O-benzyl-2-deoxy-β-D-glucopyranoside 8 tert-Butyldimethylsilyl 2-azido-3-O-benzyl-4,6-O-benzylidene-2-deoxy-β-D-glucopyranoside 4 (3.6 g, 7.24 mmol) and triethylsilane (6.5 mL, 43.4 mmol) were dissolved in anhydrous CH$_2$Cl$_2$ (70 mL) under nitrogen at 0° C. and trifluoroacetic acid (3.3 mL, 43.4 mmol) was added dropwise over 5 min. The reaction mixture was slowly warmed to room temperature, stirred for 5 h and quenched with saturated NaHCO$_3$. After addition of CH$_2$Cl$_2$ and phase separation, the aqueous phase was extracted with CH$_2$Cl$_2$. The combined organic phases were dried over MgSO$_4$, filtered and the solvents were removed in vacuo. Flash chromatography on silica gel (Hexanes:EtOAc 8:1→6:1) afforded 8 (3.1 g, 6.2 mmol, 85%) as a colorless oil. [α]$^{24}_D$: −33.9 (c 1.00, CH$_2$Cl$_2$); IR (thin film) 3472, 2111, 1257, 1113, 1069 cm$^{-1}$; $^1$H-NMR (300 MHz, CDCl$_3$) δ 7.45–7.28 (m, 10H), 4.93 (d, J=11.4 Hz, 1H), 4.77 (d, J=11.4 Hz, 1H), 4.61 (d, J=12.1 Hz, 1H), 4.56 (d, J=12.1 Hz, 1H), 4.55 (d, J=7.5 Hz, 1H), 3.73 (d, J=4.8 Hz, 2H), 3.65 (dd, J=8.5, 9.7 Hz, 1H), 3.46–3.39 (m, 1H), 3.33 (dd, J=7.5, 10.0 Hz, 1H), 3.23 (dd, J=8.5, 10.0 Hz, 1H), 0.95 (s, 9H), 0.18 (s, 6H); $^{13}$C-NMR (75 MHz, CDCl$_3$) δ 138.3, 137.9, 128.8, 128.6, 128.23, 128.16, 127.9, 127.8, 97.4, 82.5, 75.2, 74.1, 73.9, 72.2, 70.6, 68.3, 25.9, 18.3, −4.0, −5.0; FAB MS (C$_{26}$H$_{37}$N$_3$O$_5$Si) m/z (M$^+$) calcd 499.2502, obsd 499.2513. The spectral data was in agreement with the reported data (C. Murakata, T. Ogawa, Carbohydrate Res. 1992, 234, 75–91).

tert-Butyldimethylsilyl 3-O-acetyl-2-azido-6-O-benzyl-2-deoxy-β-D-glucopyranoside 9 tert-Butyldimethylsilyl 3-O-acetyl-2-azido-4,6-O-benzylidene-2-deoxy-β-D-glucopyranoside 5 (42.0 mg, 0.093 mmol) and triethylsilane (75 μL, 0.47 mmol) were dissolved in CH$_2$Cl$_2$ (930 μL) under argon at 0° C. and trifluoroacetic acid (36 μL, 0.47 mmol) was added dropwise over 6 min. The reaction mixture was slowly warmed to room temperature, stirred for 3 h and quenched with saturated NaHCO$_3$. After addition of CH$_2$Cl$_2$ and phase separation, the aqueous phase was extracted three times with CH$_2$Cl$_2$. The combined organic phases were dried over MgSO$_4$, filtered and the solvents were removed in vacuo. Flash chromatography on silica gel (Hexanes:EtOAc 8:1→6:1) furnished 9 (38.1 mg, 91%) as a colorless oil. [α]$^{24}_D$: −21.6 (c 1.00, CH$_2$Cl$_2$); IR (thin film) 3434, 2111, 1749, 1252 cm$^{-1}$; $^1$H-NMR (300 MHz, CDCl$_3$) δ 7.40–2.28 (m, 5H), 4.80 (dd, J=9.1 Hz, 10.3 Hz, 1H), 4.61 (d, J=7.7 Hz, 1H), 4.61–4.57 (m, 2H), 3.75 (dd, J=1.6, 4.9 Hz, 1H), 3.69 (ddd, J=3.5, 9.3, 9.3 Hz, 1H), 3.53–3.45 (m, 1H), 3.36 (dd, J=7.7, 10.3 Hz, 1H), 3.00 (d, J=3.7 Hz, 1H), 2.18 (s, 3H), 0.95 (s, 9H), 0.178 (s, 3H), 0.175 (s, 3H); $^{13}$C-NMR (75 MHz, CDCl$_3$) δ 171.5, 137.7, 128.6, 128.0, 127.8, 97.3, 75.4, 74.4, 73.9, 71.1, 70.3, 66.1, 25.8, 21.3, 18.2, −4.1, −5.0; FAB MS (C$_{21}$H$_{33}$N$_3$O$_6$Si) m/z (M$^+$) calcd 451.2138, obsd 451.2131.

tert-Butyldimethylsilyl 2-azido-3,6-di-O-benzyl-4-O-tert-butyldimethylsilyl-2-deoxy-β-D-glucopyranoside To a solution of tert-butyldimethylsilyl 2-azido-3,6-di-O-benzyl-2-deoxy-β-D-glucopyranoside 8 (353.7 mg, 0.708 mmol) and 2,6-lutidine (206 μL, 1.77 mmol) in CH$_2$Cl$_2$ (800 μL) was added tert-butyldimethylsilyl trifluoromethanesulfonate (244 μL, 1.06 mmol) under argon at room temperature. The reaction mixture was stirred for 1 h and quenched with saturated NaHCO$_3$. After addition of CH$_2$Cl$_2$ and phase separation the aqueous phase was extracted four times with CH$_2$Cl$_2$. The combined organic phases were dried over MgSO$_4$, filtered and solvents removed in vacuo. Flash chromatography on silica gel (Hexanes:EtOAc 25:1) afforded product (420 mg, 97%) as a colorless solid. [α]$^{24}_D$: +31.1 (c 1.00, CH$_2$Cl$_2$); IR (thin film) 2109, 1472, 1360, 1107, 1066 cm$^{-1}$; $^1$H-NMR (300 MHz, CDCl$_3$) δ 7.40–7.28 (m, 5H), 4.93 (d, J=11.1 Hz, 1H), 4.72 (d, J=11.1 Hz, 1H), 4.64 (d, J=12.2 Hz, 1H), 4.58 (d, J=7.7 Hz, 1H), 4.53 (d, J=12.2 Hz, 1H), 3.78–3.64 (m, 2H), 3.59 (dd, J=5.5, 10.8

Hz, 1H), 3.44–3.39 (m, 1H), 3.34 (dd, J=8.5, 9.8 Hz, 1H), 3.19 (dd, J=8.5, 9.8 Hz, 1H), 0.96 (s, 9H), 0.87 (s, 9H), 0.20 (s, 3H), 0.19 (s, 3H), 0.03 (s, 3H), 0.02 (s, 3H); $^{13}$C-NMR (75 MHz, CDCl$_3$) δ 138.7, 138.5, 128.50, 128.46, 127.63, 127.60, 97.5, 83.4, 76.6, 75.0, 73.5, 71.0, 69.3, 69.2, 26.1, 25.8, 18.23, 18.19, −3.6, −4.0, −4.6, −5.0; FAB MS (C$_{32}$H$_{51}$N$_3$O$_5$Si$_2$) m/z (M$^+$) calcd 613.3367, obsd 613.3359.

tert-Butyldimethylsilyl 3-O-acetyl-2-azido-6-O-benzyl-4-O-tert-butyldimethylsilyl-2-deoxy-β-D-glucopyranoside tert-Butyldimethylsilyl trifluoromethanesulfonate (9.5 μL, 0.041 mmol) was added to a solution of tert-butyldimethylsilyl 3-O-acetyl-2-azido-6-O-benzyl-2-deoxy-β-D-glucopyranoside 9 (12.4 mg, 0.027 mmol) and 2,6-lutidine (8.0 μL, 0.069 mmol) in CH$_2$Cl$_2$ (200 μL) under argon at room temperature. The reaction mixture was stirred for 1 h and quenched with saturated NaHCO$_3$. After addition of CH$_2$Cl$_2$ and phase separation, the aqueous phase was extracted three times with CH$_2$Cl$_2$. The combined organic phases were dried over MgSO$_4$, filtered and the solvents were removed in vacuo. Flash chromatography on silica gel (Hexanes:EtOAc 30:1) afforded product (15.3 mg, 98%) as a colorless solid. [α]$^{24}_D$: −11.3 (c 0.71, CH$_2$Cl$_2$); IR (thin film) 2109, 1752, 1473, 1221, 1107, 899 cm$^{-1}$; $^1$H-NMR (300 MHz, CDCl$_3$) δ 7.38–7.29 (m, 5H), 4.87 (dd, J=9.0, 10.5 Hz, 1H), 4.65 (d, J=12.4 Hz, 1H), 4.64 (d, J=7.8 Hz, 1H), 4.53 (d, J=12.4 Hz, 1H), 3.79 (dd, J=9.3, 9.1 Hz, 1H), 3.70–3.60 (m, 2H), 3.45–3.38 (m, 1H), 2.15 (s, 3H), 0.95 (s, 9H), 0.82 (s, 9H), 0.18 (s, 3H), 0.17 (s, 3H), 0.06 (s, 3H), 0.03 (s, 3H); $^{13}$C-NMR (75 MHz, CDCl$_3$) δ 170.1, 138.3, 128.5, 127.7, 127.6, 97.2, 76.4, 74.9, 73.5, 69.1, 68.5, 67.0, 25.9, 25.8, 21.7, 18.2, 18.1, −3.9, −4.1, −4.5, −5.0; FAB MS (C$_{27}$H$_{47}$N$_3$O$_6$Si$_2$) m/z (M$^+$) calcd 565.3003, obsd 565.3011.

Synthesis of Glucosamine Donors:

6-O-Acetyl-2-azido-3-O-benzyl-4-O-tert-butyldimethylsilyl-2-deoxy-α-D-glucopyranosyl fluoride 10α and 6-O-Acetyl-2-azido-3-O-benzyl-4-O-tert-butyldimethylsilyl-2-deoxy-β-D-glucopyranosyl fluoride 10β tert-Butyldimethylsilyl 6-O-acetyl-2-azido-3-O-benzyl-4-O-tert-butyldimethylsilyl-2-deoxy-β-D-glucopyranoside (4.0 g, 7.07 mmol) was dissolved in THF (60 mL) and cooled to 0° C. Glacial acetic acid (500 μL, 8.7 mmol) and TBAF (1 M in THF, 8.2 mL, 8.2 mmol) were added simultaneously. After 30 min, the mixture was poured into ether (200 mL) and washed three times with brine. The organic layer was dried over NASO$_4$, filtered and the solvents were removed in vacuo. The residue was coevaporated with toluene, dissolved in anhydrous THF (20 mL) and cooled to −30° C. DAST (1.2 mL, 9.08 mmol) was added dropwise and the mixture was stirred for 5 min at −30° C. and 30 min at room temperature. The reaction mixture was cooled to −30° C. and anhydrous methanol (500 μL) was added. After warming to room temperature, the mixture was poured into EtOAc (300 mL) and washed with saturated NaHCO$_3$, water and brine. The organic layer was dried over NASO$_4$, filtered and the solvents were removed in vacuo. Flash chromatography on silica gel (Hexanes:EtOAc 95:5) afforded a mixture (5:1) of 10α and 10β (3.0 g, 6.62 mmol, 94%) as a crystalline solid. 10α: $^1$H-NMR (300 MHz, CDCl$_3$) δ 7.45–7.28 (m, 5H), 5.68 (dd, J=2.7, 52.7, 1H), 4.92 (d, J=11.0 Hz, 1H), 4.84 (d, J=11.0 Hz, 1H), 4.45 (dd, J=1.9, 12.1 Hz, 1H), 4.11 (dd, J=4.7, 12.1 Hz, 1H), 4.04–3.94 (m, 1H), 3.83–3.71 (m, 2H), 3.74–3.36 (m, 1H), 2.11 (s, 3H), 0.92 (s, 9H), 0.06 (s, 3H), 0.05 (s, 3H); $^{13}$C-NMR (75 MHz, CDCl$_3$) δ 170.7, 137.7, 128.5, 127.5, 107.6, 104.6, 80.1, 75.6, 73.14, 73.08, 70.4, 64.3, 64.0, 62.5, 26.1, 21.1, 18.3, −3.4, −4.7. 10β: $^1$H-NMR (300 MHz, CDCl$_3$) δ 7.45–7.28 (m, 5H), 5.68 (dd, J=2.7 Hz, 52.7 Hz, 1H), 4.92 (d, J=11.0 Hz, 1H), 4.84 (d, J=11.0 Hz, 1H), 4.45 (dd, J=1.9 Hz, 12.1 Hz, 1H), 4.11 (dd, J=4.7 Hz, 12.1 Hz, 1H), 4.04–3.94 (m, 1H), 3.83–3.71 (m, 2H), 3.74–3.36 (m, 1H), 2.11 (s, 3H), 0.92 (s, 9H), 0.06 (s, 3H), 0.05 (s, 3H); $^{13}$C-NMR (75 MHz, CDCl$_3$) δ 170.7, 137.7, 128.6, 128.5, 128.2, 127.9, 127.6, 109.6, 106.7, 82.4, 82.3, 75.4, 74.8, 74.7, 70.2, 66.6, 66.3, 62.8, 26.0, 21.1, 18.2, −3.5, −4.7.

O-(6-O-Acetyl-2-azido-3-O-benzyl-4-O-tert-butyldimethylsilyl-2-deoxy-α-D-glucopyranosyl) trichloroacetimidate 11α and O-(6-O-Acetyl-2-azido-3-O-benzyl-4-O-tert-butyldimethylsilyl-2-deoxy-β-D-glucopyranosyl) trichloroacetimidate 11β tert-Butyldimethylsilyl 6-O-acetyl-2-azido-3-O-benzyl-4-O-tert-butyldimethylsilyl-2-deoxy-β-D-glucopyranoside (1.16 g, 2.05 mmol) was dissolved in anhydrous THF (20 mL) and cooled to 0° C. Glacial acetic acid (146 μl, 2.56 mmol) and TBAF (1M in THF) (2.25 mL, 2.25 mmol) were added simultaneously. After 30 min, the mixture was poured into ether (200 mL) and washed three times with brine. The organic layer was dried over Na$_2$SO$_4$, filtered and the solvents were removed in vacuo. The residue was dissolved in CH$_2$Cl$_2$ (50 mL) and cooled to 0° C. Trichloroacetonitrile (3.1 mL, 30.9 mmol) and DBU (30 μL, 0.2 mmol) were added and the mixture was stirred for 1 h at 0° C. and concentrated in vacuo. Flash chromatography on silica gel (Hexanes:EtOAc 85:15) afforded a mixture of 11α and 11β (27/73) (1.12 g, 1.88 mmol, 92%) as a colorless oil. 11α: [α]$^{24}_D$: +118.6 (c 1.69, CH$_2$Cl$_2$); IR (thin film) 3344, 2954, 2929, 2857, 2110, 1745, 1674, 1363, 1255, 1142, 1069, 1021, 836 cm$^{-1}$; $^1$H-NMR (500 MHz, CDCl$_3$) δ 8.75 (s, 1H, NH), 7.41–7.28 (m, 5H, arom. H), 6.44 (d, J=3.4 Hz, 1H, H-1), 4.92 (d, J=11.3 Hz, 1H, benzyl-CH$_2$), 4.86 (d, J=11.0 Hz, 1H, benzyl-CH$_2$), 4.40 (dd, J=12.2, 2.1 Hz, 1H, H-6a), 4.08 (dd, J=12.2, 4.6 Hz, 1H, H-6b), 3.95–3.99 (m, 1H), 3.77–3.82 (m, 2H), 3.66–3.71 (m, 1H), 2.06 (s, 3H, acetyl-CH$_3$), 0.91 (s, 9H, tert-butyl), 0.06 (s, 3H, CH$_3$), 0.05 (s, 3H, CH$_3$); $^{13}$C-NMR (125 MHz, CDCl$_3$) δ 170.8, 160.9, 137.9, 128.5, 127.8, 127.6, 94.8, 80.5, 75.5, 73.3, 70.8, 63.7, 62.7, 26.1, 21.0, 18.2, −3.5, −4.8; FAB MS (C$_{23}$H$_{33}$Cl$_3$N$_4$O$_6$Si) m/z (M$^+$) calcd 594.1235, obsd 594.1219. 11β: [α]$^{24}_D$: +43.6 (c 1.11, CH$_2$Cl$_2$); IR (thin film) 3329, 2928, 2857, 2113, 1745, 1676, 1253, 1098, 1063, 838 cm$^{-1}$; $^1$H-NMR (500 MHz, CDCl$_3$) δ 8.74 (s, 1H, NH), 7.48–7.28 (m, 5H, arom. H), 5.66 (d, J=8.2 Hz, 1H, H-1), 4.94 (d, J=11.3 Hz, 1H, benzyl-CH$_2$), 4.79 (d, J=11.3 Hz, 1H, benzyl-CH$_2$), 4.42 (dd, J=11.9, 2.4 Hz, 1H, H-6a), 4.13 (dd, J=12.2, 4.9 Hz, 1H, H-6b), 3.77 (dd, J=9.5, 8.5 Hz, 1H), 3.69 (dd, J=9.8, 8.2 Hz, 1H), 3.60 (ddd, J=9.5, 4.9, 2.4 Hz, 1H, H-5), 3.36 (dd, J=9.5, 8.5 Hz, 1H), 2.08 (s, 3H, acetyl-CH$_3$), 0.90 (s, 9H, tert-butyl), 0.05 (s, 3H, CH$_3$), 0.04 (s, 3H, CH$_3$); $^{13}$C-NMR (125 MHz, CDCl$_3$) δ 170.9, 161.2, 138.1, 128.6, 127.9, 127.6, 97.1, 83.4, 75.5, 74.4, 70.4, 66.2, 62.8, 26.0, 21.1, 18.2, −3.5, −4.8; FAB MS (C$_{23}$H$_{33}$Cl$_3$N$_4$O$_6$Si) m/z (M$^+$) calcd 594.1235, obsd 594.1222.

3,6-Di-O-acetyl-2-azido-4-O-tert-butyldimethylsilyl-2-deoxy-α-D-glucopyranosyl bromide 12

TBAF (1.0 M in THF, 6.4 mL) and glacial acetic acid (350 μL, 5.9 mmol) were added dropwise to a solution of tert-butyldimethylsilyl 3,6-di-O-acetyl-2-azido-4-O-tert-butyldimethylsilyl-2-deoxy-β-D-glucopyranoside (2.90 g, 5.6 mmol) in THF (60 mL) under nitrogen at 0° C. The reaction mixture was warmed to room temperature, stirred for 1.5 h and quenched with saturated NaHCO$_3$. After extracting with CH$_2$Cl$_2$ (3×), the combined organic phases were dried over MgSO$_4$, filtered and the solvents were removed in vacuo. The crude material was evaporated three times with toluene, dried under vacuum for 1 h and dissolved in THF (17 mL). The resulting solution was added to a suspension of $SOBr_2$ (760 μL, 9.6 mmol) and imidazole (585 mg, 8.6 mmol) in anhydrous THF (55 mL) at 0° C. The resulting suspension was stirred for 1 h, diluted with anhydrous ether, filtered over a pad of florisil and ground $Na_2S_2O_3$ and concentrated to furnish 12 as a yellow solid (2.1 g, 4.5 mmol, 76%) which was used without further purification. $[α]^{24}_D$: +5.8 (c 1.00, $CHCl_3$); IR (thin film) 2929, 2859, 2113, 1746, 1473, 1235, 1006 $cm^{-1}$; $^1$H-NMR (500 MHz, $CDCl_3$) δ 6.40 (d, J=3.9 Hz, 1H, H-1), 5.43 (dd, J=8.8, 10.4 Hz, 1H, H-3), 4.41 (dd, J=2.1, 12.5 Hz, 1H, H-6a), 4.17–4.11 (m, 2H, H-6b, H-5), 3.87 (t, J=8.8 Hz, 1H, H-4), 3.58 (dd, J=3.9, 10.4 Hz, 1H, H-2), 2.17 (s, 3H, $OCH_3$), 2.10 (s, 3H, $OCH_3$), 0.86 (s, 9H, $C(CH_3)_3$), 0.07 (s, 3H, $SiCH_3$), 0.06 (s, 3H, $SiCH_3$); $^{13}$C-NMR (100 MHz, $CDCl_3$) δ 170.6, 169.6, 88.1, 75.1, 73.7, 68.6, 63.4, 61.9, 25.8, 21.5, 20.9, 18.1, −3.8, −4.8; FAB MS ($C_{16}H_{28}BrN_3O_7Si$) m/z ($M^+$) calcd 465.0930, obsd 465.0940. (Procedure: D. K. Baeschlin, A. R. Chaperon, L. G. Green, M. G. Hahn, S. J. Ince, S. V. Ley, Chem. Eur. J. 2000, 6, 172–186).

O-(3,6-Di-O-acetyl-2-azido-4-O-tert-butyldimethylsilyl-2-deoxy-α-D-glucopyranosyl) trichloroacetimidate 13α and O-(3,6-Di-O-acetyl-2-azido-4-O-tert-butyldimethyl-silyl-2-deoxy-β-D-glucopyranosyl) trichloroacetimidate 13β

TBAF (1.0 M in THF, 1.4 mL) and glacial acetic acid (80 μL, 5.9 mmol) were added dropwise to a solution of tert-butyldimethylsilyl 3,6-di-O-acetyl-2-azido-4-O-tert-butyldimethylsilyl-2-deoxy-β-D-glucopyranoside (590 mg, 1.14 mmol) in THF (12 mL) under nitrogen at 0° C. The reaction mixture was warmed to room temperature, stirred for 1.5 h and quenched with saturated $NaHCO_3$ solution. After extraction with $CH_2Cl_2$ (3×), the combined organic phases were dried over $MgSO_4$, filtered and the solvents were removed in vacuo. The crude material was dried by coevaporation with anhydrous toluene and vacuum for 1 h and dissolved in $CH_2Cl_2$ (25 mL). Trichloroacetonitrile (1.3 mL, 12.50 mmol) and freshly activated 4 Å powdered molecular sieves (300 mg) were added and the mixture was stirred for 30 minutes at room temperature. After cooling to 0° C., DBU (30 μl, 0.2 mmol) was added and the temperature was allowed to rise to room temperature. After 1 h, the mixture was filtered through Celite and the solvents were removed in vacuo. Flash chromatography on silica gel (Hexanes:EtOAc 85:15) afforded 13α (437 mg, 0.80 mmol, 70%) and 13β (94 mg, 0.17 mmol, 15%). 13α: $^1$H-NMR (500 MHz, $CDCl_3$) δ 8.81 (s, 1H, NH), 6.44 (d, J=3.6 Hz, 1H, H-1), 5.43 (dd, J=8.8, 10.4 Hz, 1H, H-3), 4.41 (dd, J=1.9, 12.0 Hz, 1H, H-6a), 4.12–3.99 (m, 2H, H-6b, H-5), 3.87 (t, J=9.1 Hz, 1H, H-4), 3.58 (dd, J=3.6, 10.7 Hz, 1H, H-2), 2.17 (s, 3H, $OCH_3$), 2.01 (s, 3H, $OCH_3$), 0.86 (s, 9H, $C(CH_3)_3$), 0.08 (s, 3H, $SiCH_3$), 0.06 (s, 3H, $SiCH_3$); $^{13}$C-NMR (125 MHz, $CDCl_3$) δ 170.5, 169.7, 160.8, 94.7, 72.77, 69.1, 62.5, 61.5, 25.9, 21.6, 21.0, 18.2, −3.8, −4.6. 13β: $^1$H-NMR (500 MHz, $CDCl_3$) δ 8.81 (s, 1H, NH), 5.73 (d, J=8.2 Hz, 1H, H-1), 5.03 (dd, J=8.8 Hz, J=9.8 Hz, 1H, H-3), 4.40 (dd, J=2.1 Hz, J=11.9 Hz, 1H, H-6a), 4.13 (dd, J=4.2 Hz, J=11.9 Hz, 1H, H-6b), 3.87 (t, J=9.5 Hz, 1H, H-4), 3.58 (m, 2H, H-2, H-5), 2.17 (s, 3H, $OCH_3$), 2.08 (s, 3H, $OCH_3$), 0.84 (s, 9H, $C(CH_3)_3$), 0.05 (s, 3H, SiCH3), 0.04 (s, 3H, $SiCH_3$); $^{13}$C-NMR (125 MHz, $CDCl_3$) δ 170.7, 169.9, 160.8, 96.6, 75.3, 68.8, 64.1, 62.4, 25.9, 25.8, 25.8, 21.5, 21.1, 18.1, −3.9, −4.8.

O-(3,6-Di-O-benzyl-2-azido-4-O-tert-butyldimethylsilyl-2-deoxy-D-glucopyranosyl)trichloroacetimidate 14 tert-Butyldimethylsilyl 6-O-benzyl-2-azido-3-O-acetyl-4-O-tert-butyldimethylsilyl-2-deoxy-β-D-glucopyranoside 8 (0.121 mg, 0.197 mmol) was dissolved in anhydrous THF (1.5 mL) and cooled to 0° C. Glacial acetic acid (20.0 μL, 0.256 mmol) and TBAF (1M in THF, 240 μl, 0.240 mmol) were added simultaneously. After 30 min, the mixture was poured into EtOAc (50 mL) and washed with sat. $NaHCO_3$. The organic layer was dried over $Na_2SO_4$, filtered and the solvents were removed in vacuo. The residue was dissolved in $CH_2Cl_2$ (1 mL) and cooled to 0° C. Trichloroacetonitrile (1.0 mL) and DBU (5 μL, 0.03 mmol) were added and the mixture was stirred for 1 h at 0° C., diluted with $CH_2Cl_2$ (30 mL), passed through a plug of silica and concentrated in vacuo. Flash chromatography on silica gel (Hexanes:EtOAc 5:1) afforded 14α and 14β (87.5 mg, 0.137 mmol, 69%) as an inseparable 1:1 mixture. $^1$H-NMR (500 MHz, $CDCl_3$) δ 8.76 (s, 1H, NHβ), 8.73 (s, 1H, NHα), 7.40–7.27 (m, 15H, arom. H), 6.48 (d, J=3.6 Hz, 1H, H1α), 8.24 (d, J=8.2, 1H, H1β), 4.94 (d, J=11.6 Hz, 1H), 4.91 (d, J=11.9 Hz, 1H), 4.85 (d, J=11.0 Hz, 1H), 4.78 (d, J=11.3 Hz, 1H), 4.66 (d, J=12.2 Hz, 1H), 4.60 (d, J=12.2 Hz, 1H), 4.53 (d, J=12.5 Hz, 1H), 4.50 (d, J=11.9 Hz, 1H), 3.95–3.90 (m, 1H), 3.86 (app t, J=9.0 Hz, 1H), 3.81–3.73 (m, 3H), 3.71–3.64 (m, 5H), 3.60–3.57 (m, 2H), 3.38 (app t, J=9.0 Hz, 1H), 0.88 (s, 9H), 0.87 (s, 9H), 0.06–0.02 (m, 12H). $^{13}$C-NMR (125 MHz, $CDCl_3$) δ 161.2, 161.0, 138.4, 138.3, 138.1, 128.5, 128.5, 128.5, 127.8, 127.7, 127.6, 97.1, 95.2, 83.5, 80.6, 77.7, 75.4, 75.2, 73.3, 70.6, 70.4, 68.4, 66.3, 63.9, 26.2, 26.1, 18.2, 18.2, −3.5, −3.6, −4.6.

O-(6-O-Benzyl-2-azido-3-O-acetyl-4-O-tert-butyldimethylsilyl-2-deoxy-α-D-glucopyranosyl) trichloroacetimidate 15α and O-(6-O-Benzyl-2-azido-3-O-acetyl-4-O-tert-butyldimethylsilyl-2-deoxy-β-D-glucopyranosyl) trichloroacetimidate 15β tert-Butyldimethylsilyl 6-O-benzyl-2-azido-3-O-acetyl-4-O-tert-butyldimethylsilyl-2-deoxy-β-D-glucopyranoside 9 (0.170 mg, 0.30 mmol) was dissolved in anhydrous THF (3 mL) and cooled to 0° C. Glacial acetic acid (20 μL, 0.35 mmol) and TBAF (1M in THF) (330 μL, 0.33 mmol) were added simultaneously. After 30 min, the mixture was poured into ether (50 mL) and washed three times with brine. The organic layer was dried over $Na_2SO_4$, filtered and the solvents were removed in vacuo. The residue was dissolved in $CH_2Cl_2$ (3 mL) and cooled to 0° C. Trichloroacetonitrile (770 μl, 7.67 mmol) and DBU (5 μL, 0.03 mmol) were added and the mixture was stirred for 1 h at 0° C. and concentrated in vacuo. Flash chromatography on silica gel (Hexanes:EtOAc 85:15) afforded a mixture of 15α and 15β (2.7/1) (0.160 mg, 0.27 mmol, 89%) as a colorless oil. 15α $^1$H-NMR (500 MHz, $CDCl_3$) δ 8.77 (s, 1H, NH), 7.36–7.27 (m, 5H, arom. H), 6.50 (d, J=3.4 Hz, 1H, H-1), 5.43 (dd, J=7.9, 10.7 Hz, 1H, H-3), 4.58 (d, J=11.9 Hz, 1H, benzyl-$CH_2$), 4.51 (d, J=11.9 Hz, 1H, benzyl-$CH_2$), 4.01–3.95 (m, 2H, H-4, H-5), 3.75 (dd, J=3.3, 11.3 Hz, 1H, H-6a), 3.65 (dd, 1H, H-6b), 3.48 (dd, J=3.4, 10.4 Hz, 1H, H-2), 2.17 (s, 3H, acetyl-$CH_3$), 0.84 (s, 9H, tert-butyl), 0.07 (s, 6H, $CH_3$); $^{13}$C-NMR (125 MHz, $CDCl_3$) δ 170.0, 161.0, 138.1, 128.5, 127.8, 127.7, 95.2, 74.7, 73.6, 73.1, 68.7, 68.0, 61.7, 25.9, 21.6, 18.2, −4.0, −4.6. 15β: $[α]^{24}_D$: +x (c x, $CH_2Cl_2$); IR (thin film) XX $cm^{-1}$; $^1$H-NMR (500 MHz, $CDCl_3$) δ 8.78 (s, 1H, NH), 7.34–7.27 (m, 5H, arom. H), 5.76 (d, J=8.5 Hz, 1H, H-1), 5.03 (dd, J=8.8, 10.0 Hz, 1H, H-3), 4.64 (d, J=12.2 Hz, 1H, benzyl-$CH_2$), 4.53 (d, J=12.3 Hz, 1H, benzyl-$CH_2$), 3.91 (t, J=9.1 Hz, 1H, H-4), 3.68–3.58 (m, 4H, H-2, H-5, H6a, H6b), 2.16 (s, 3H, acetyl-$CH_3$), 0.82 (s, 9H, tert-butyl), 0.06 (s, 3H, $CH_3$), 0.04 (s, 3H, $CH_3$).

Synthesis of Non-Reducing End Monosaccharide:
tert-Butyldimethylsilyl-6-O-acetyl-2-azido-2-deoxy-β-D-glucopyranoside 16 tert-Butyldimethylsilyl 3,4,6-tri-O-acetyl-2-azido-2-deoxy-β-D-glucopyrano side 2 (1.23 g; 2.77 mmol) was dissolved in methanol (10 mL). NaOMe (25% in methanol, 170 μL) was added. After 15 min DOWEX-50 acidic resin was added and the mixture was stirred until the pH reached 6. The DOWEX resin was filtered off and the solvent was removed under reduced pressure to afford a yellow oil. The residue was coevaporated twice with toluene, dissolved in 2,4,6-collidine (7 mL), cooled to −40° C. and acetyl chloride (196 μL, 2.74 mmol) was added. After stirring the reaction mixture for 3 h, a second portion of acetyl chloride (42 μL, 0.6 mmol) was added. The mixture was stirred for another 1 h at −40° C. and for 1 h at room temperature and then quenched with saturated $NaHCO_3$. After addition of $CH_2Cl_2$ and phase separation the aqueous phase was extracted three times with $CH_2Cl_2$. The combined organic phases were dried over $MgSO_4$, filtered and the solvents were removed in vacuo. Flash chromatography (Hexanes:EtOAc 4:1) on silica afforded 16 (933 mg, 2.58 mmol, 93%) as a colorless syrup. $[\alpha]^{24}_D$: −7.0 (c 1.00, $CHCl_3$); IR (thin film) 3412, 2929, 2958, 2111, 1741, 1463, 1370, 1257, 1177 $cm^{-1}$; $^1$H-NMR (500 MHz, $CDCl_3$) δ 4.55 (d, J=7.5 Hz, 1H), 4.38–4.26 (m, 2H), 4.13 (bs, 2H, OH), 3.45–3.20 (m, 4H), 2.06 (s, 3H, $OCH_3$), 0.93 (s, 9H, $C(CH_3)_3$), 0.15 (s, 3H, $SiCH_3$), 0.14 (s, 3H, $SiCH_3$); $^{13}$C-NMR (125 MHz, $CDCl_3$) δ 171.9, 97.3, 74.5, 73.8, 70.6, 68.2, 63.7, 25.7, 21.0, 18.1, −3.5, −4.6; FAB MS ($C_{14}H_{27}N_3O_6Si$) m/z ($M^+$) calcd 361.1669, obsd 361.1680.

tert-Butyldimethylsilyl-6-O-acetyl-2-azido-3,4-di-O-benzyl-2-deoxy-β-D-glucopyranoside 17 tert-Butyldimethylsilyl-6-O-acetyl-2-azido-2-deoxy-β-D-glucopyranoside 16 (7.1 g, 19.64 mmol) was dissolved in $CH_2Cl_2$ (100 mL). Powdered, freshly activated 4 Å molecular sieves (20 g) and benzyl bromide (12 mL, 100 mmol) were added and this mixture stirred for 30 min. Silver(I) oxide (26.4 g, 114 mmol) was added and light was excluded from the reaction mixture. After 48 h, the reaction mixture was filtered over Celite and the filtrate was concentrated under reduced pressure. Flash chromatography on silica gel (Hexanes-EtOAc 97:3) afforded 17 (8.5 g, 15.7 mmol, 80%) as a colorless oil. $[\alpha]^{24}_D$: −4.7 (c 1.40, $CH_2Cl_2$); IR (thin film) 3031, 2955, 2858, 2109, 1745, 1454, 1252, 1042, $cm^{-1}$; $^1$H-NMR (500 MHz, $CDCl_3$) δ 7.43–7.29 (m, 10H, arom. H), 4.95 (d, J=11.0 Hz, 1H, benzyl-$CH_2$), 4.89 (d, J=11.0 Hz, 1H, benzyl-$CH_2$), 4.82 (d, J=10.7 Hz, 1H, benzyl-$CH_2$), 4.61 (d, J=11.0 Hz, 1H, benzyl-$CH_2$), 4.56 (d, J=7.6 Hz, 1H, H-1), 4.36 (dd, J=11.9, 1.5 Hz, 1H, H-6a), 4.17 (dd, J=11.9, 5.8 Hz, 1H, H-6b), 3.55–3.49 (m, 2H, H-4 and H-5), 3.47–3.43 (m, 1H, H-3), 3.38 (dd, J=9.8, 7.6 Hz, 1H, H-2), 2.06 (s, 3H, acetyl-$CH_3$), 0.98 (s, 9H, tert-butyl), 0.20 (s, 3H, $CH_3$), 0.19 (s, 3H, $CH_3$); $^{13}$C-NMR (125 MHz, $CDCl_3$) δ 170.8, 138.0, 137.7, 128.7, 128.6, 128.2, 128.2, 128.1, 97.3, 83.1, 77.7, 75.7, 75.2, 73.2, 68.8, 63.2, 25.8, 21.0, 18.2, −4.2, −5.1; FAB MS ($C_{28}H_{39}N_3O_6Si$) m/z ($M^+$) calcd 541.2608, obsd 541.2606.

O-(6-O-Acetyl-2-azido-3,4-di-O-benzyl-2-deoxy-α-D-glucopyranosyl) trichloroacetimidate 18α and O-(6-O-Acetyl-2-azido-3,4-di-O-benzyl-2-deoxy-β-D-glucopyranosyl) trichloroacetimidate 18β

To a solution of 17 (756 mg, 1.4 mmol) in anhydrous THF (15 mL) at 0° C. glacial acetic acid (100 μl, 1.75 mmol) and TBAF (1 M in THF, 1.55 mL, 1.55 mmol) were added simultaneously. After 30 min this mixture was poured into ether (150 mL) and extracted three times with brine. The organic layer was dried over $Na_2SO_4$, filtered and the solvents were removed in vacuo. The residue was dissolved in anhydrous dichloromethane (50 mL) and cooled in an ice bath. Trichloroacetonitrile (2.1 mL, 21 mmol) and DBU (21 μL, 0.14 mmol) were added. After 45 min, the solvents were removed in vacuo. Flash chromatography on silica gel (Hexanes:EtOAc 85:15→8:2) afforded a mixture (58:42) of 18α and 18β (708 mg, 1.24 mmol, 88%) as a colorless oil. $^1$H-NMR (500 MHz, $CDCl_3$) δ 8.76 (s, 1H, NH), 7.44–7.26 (m, 10H, arom. H), 6.42 (d, J=3.4 Hz, 0.58H, H-1α), 5.64 (d, J=8.2 Hz, 0.42H, H-1β), 4.97–4.86 (m, 4H, benzyl-$CH_2$), 4.64–4.60 (m, 1H), 4.35–4.24 (m, 2H), 4.10–4.06 (m, 1H), 3.73–3.57 (m, 2H), 2.03 (s, 3H, acetyl-$CH_3$).

Synthesis of Uronic Acid Monosaccharides:
Methyl 3-O-benzyl-1,2-O-isopropylidene-α-D-glucofuranosiduronate 20

1,2:5,6-Di-O-isopropylidene-α-D-glucofuranose 19 (52.06 g, 200 mmol) was dissolved in THF (500 mL) and NaH (60% in mineral oil, washed with pentanes) (9.6 g, 240 mmol) was added in portions. After the evolution of hydrogen ceased, tetrabutylammonium iodide (500 mg, 1.35 mmol) and benzyl bromide (25 ml, 210 mmol) were added and the mixture stirred for 10 h at room temperature. Water was added slowly to the reaction mixture and the organic solvents were removed in vacuo. The aqueous phase was extracted three times with EtOAc. The combined organic phases were dried over $Na_2SO_4$, filtered through a plug of silica gel and the solvents were removed in vacuo.

Aqueous acetic acid (66%, 300 mL) was added to the resulting oil and the mixture was stirred for 14 h at room temperature and for 6 h at 40° C. After removal of the solvents, the remaining residue was dissolved in $CH_2Cl_2$ and extracted with saturated $NaHCO_3$. After phase separation, the aqueous layer was extracted with $CH_2Cl_2$. The combined organic phases were dried over $Na_2SO_4$, filtered and the solvents were removed in vacuo.

The residual oil was dissolved in $CH_2Cl_2$ (750 mL) and pyridine (80 mL), before DMAP (3,5 g, 28.6 mmol) and tert-butyldimethylsilyl chloride (32 g, 212 mmol) were added. After stirring at room temperature for 19 h, the mixture was extracted with water, 1 N HCl, brine and saturated $NaHCO_3$. The organics were dried over $Na_2SO_4$, filtered and the solvents were removed in vacuo. The residue was dissolved in anhydrous pyridine (170 mL) and DMAP (1 g, 8.2 mmol) was added. The mixture was cooled to 0° C. and acetic anhydride (38 ml, 403 mmol) was added dropwise. After stirring overnight at room temperature, the solvents were removed in vacuo. The residue was dissolved in EtOAc and extracted with water, 1 N HCl, brine and saturated $NaHCO_3$. The organic layer was dried over $Na_2SO_4$, filtered and the solvents were removed in vacuo.

The residue (91.2 g, max. 195 mmol) was dissolved in THF (300 mL) and cooled to 0° C. To this solution, HF-pyridine (24 mL) in pyridine (80 mL) was added and stirred overnight at room temperature. The reaction mixture was poured into water and extracted three times with EtOAc. The combined organic phases were extracted with water, 1 N HCl, water, saturated $NaHCO_3$, dried over $Na_2SO_4$, filtered and the solvents were removed in vacuo.

The residue was dissolved in $CH_2Cl_2$ (400 mL) and TEMPO (800 mg, 5.1 mmol) was added. A mixture of saturated $NaHCO_3$ (700 mL), water (200 mL), KBr (2.25 g, 18.9 mmol) and tetrabutylammonium bromide (3.45 g, 10.7 mmol) was added and the resulting mixture was cooled to 0° C. With vigorous stirring, commercially available household bleach (700 mL) was added in 100 mL portions every 10 min. After complete addition, stirring was continued for 30 min and methanol was added until the mixture was decolorized. After 20 min, the aqueous layer was extracted with $CH_2Cl_2$ followed by the dropwise addition of conc. HCl to pH 1. The aqueous layer was extracted three times with $CH_2Cl_2$. The organic layers were dried over $Na_2SO_4$, filtered and the solvents were removed in vacuo.

The residue was dissolved in methanol (280 mL), 4 N NaOH (42 mL) was added and the mixture was stirred overnight at room temperature. The mixture was acidified with conc. HCl and extracted five times with $CH_2Cl_2$. The combined organic phases were dried over $Na_2SO_4$, filtered and the solvents were removed in vacuo.

The residue was dissolved in anhydrous DMF (200 mL) and powdered $KHCO_3$ (27.4 g, 274 mmol) and methyl iodide (17 mL, 273 mmol) were added. After stirring at room temperature overnight, the mixture was poured into ether and extracted twice with water, saturated $Na_2SO_3$, and water. The organic phase was dried over $Na_2SO_4$, filtered and the solvents were removed in vacuo to afford 20 (44 g, 130 mmol, 65%) as a slightly yellow oil. $^1$H-NMR (300 MHz, $CDCl_3$) δ 7.40–7.27 (m, 5H), 6.04 (d, J=3.9 Hz, 1H), 4.70–4.52 (m, 4H), 4.41 (dd, J=6.2, 3.8 Hz, 1H), 4.16 (d, J=3.8 Hz, 1H), 3.76 (s, 3H), 3.34 (d, J=9.1 Hz, 1H), 1.50 (s, 3H), 1.34 (s, 3H). The spectral data was in agreement with the reported data (J.-C. Jacquinet, M. Petitou, P. Duchaussoy, I. Lederman, J. Choay, G. Torri, P. Sinay. *Carbohydrate Research* 1984, 130, 221–241).

Methyl 3-O-benzyl-D-glucopyranosiduronate 21

Methyl 3-O-benzyl-1,2-O-isopropylidene-α-D-glucofuranosiduronate 20 (3.43 g, 10.14 mmol) was dissolved in 90% aqueous trifluoroacetic acid (20 mL) and stirred for 15 min at room temperature. The solvent was evaporated and the residue coevaporated twice with water and twice with toluene to afford methyl 3-O-benzyl-D-glucopyranosiduronate 21, which was used without further purification. The spectral data was in agreement with the reported data (J.-C. Jacquinet, M. Petitou, P. Duchaussoy, I. Lederman, J. Choay, G. Torri, P. Sinay. *Carbohydrate Research* 1984, 130, 221–241).

Methyl 3-O-benzyl-1,2-O-isopropylidene-5-O-levulinoyl-β-L-idofuranosiduronate 22

A solution of trifluoromethanesulfonic anhydride (13 mL) in $CH_2Cl_2$ (250 mL) was added dropwise to a mixture of pyridine (13 mL) and $CH_2Cl_2$ (132 mL) at -20° C. The mixture was allowed to warm to -10° C. and a solution of methyl 3-O-benzyl-1,2-O-isopropylidene-α-D-glucofuranosiduronate 20 (12 g, 35.5 mmol) in $CH_2Cl_2$ (123 mL) was added dropwise. After 1 h at -10° C., the mixture was poured into ice cold water containing $NaHCO_3$ and stirred for 1 h. The organic layer was washed with 3% HCl, water, dried over $MgSO_4$, filtered and the solvents were removed in vacuo. Sodium levulinate (9.8 g, 71 mmol) was added to a solution of the crude residue in DMF (65 mL) and the resulting mixture was stirred overnight at 80° C. and cooled to room temperature. After dilution with EtOAc, the mixture was washed with water and the organic phase was dried over $MgSO_4$, filtered and the solvents were removed in vacuo. Flash chromatography on silica gel (Toluene:EtOAc 9:1→7:3) afforded 22 (12.8 g, 29.3 mmol, 82%) as an amorphous solid. $[α]^{24}_D$: -4.2 (c 1, $CHCl_3$); IR (thin film) 2512, 1751, 1718, 1025 cm$^{-1}$; $^1$H-NMR (500 MHz, $CDCl_3$) δ 7.36–7.28 (m, 5H, arom. H), 5.97 (d, J=3.9 Hz, 1H, H-1), 5.53 (d, J=7.0 Hz, 1H, H-5), 4.66–4.62 (m, 3H, benzyl-$CH_{2a}$, H-2, H-4), 4.50 (d, J=11.4 Hz, 1H, benzyl-$CH_{2b}$), 4.16 (d, 1H, H-3), 3.69 (s, 3H, $OCH_3$), 2.73–2.63 (m, 4H, levulinic-$CH_2$), 2.12 (s, 3H, $OCH_3$), 1.59 (s, 3H, $CH_3$), 1.34 (s, 3H, $CH_3$); $^{13}$C-NMR (125 MHz, $CDCl_3$) δ 205.3, 171.9, 168.5, 137.2, 128.6, 128.4, 128.0, 112.7, 105.1, 83.1, 82.7, 72.5, 70.9, 52.8, 38.0, 30.0, 28.0, 27.3, 26.8; FAB MS ($C_{22}H_{28}O_9$) m/z (M$^+$) calcd 436.1733, obsd 436.1742.

Methyl 3-O-benzyl-L-idopyranosiduronate 23

Hydrazine hydrate (7.3 mL, 146 mmol) was added to a solution of methyl 3-O-benzyl-1,2-O-isopropylidene-5-O-levulinoyl-β-L-idofuranosiduronate 22 (12.8 g, 29.3 mmol) in pyridine-acetic acid (3:2, 290 mL) at 0° C. After 15 min, acetone (1.2 L) was added, and the mixture was stirred at room temperature for 15 min. After removal of the solvents in vacuo, the crude product was dissolved in aqueous trifluoroacetic acid (90%, 70 mL). The mixture was stirred for 15 min, the solvents removed in vacuo and coevaporated twice with water to give a white solid, which was recrystallized from ethyl acetate/hexanes to afford 23 (8.0 g, 26.8 mmol, 91%). Analytical data was in agreement with reported data (J.-C. Jacquinet, M. Petitou, P. Duchaussoy, I. Lederman, J. Choay, G. Torri, P. Sinay. *Carbohydrate Research* 1984, 130, 221–241).

Methyl 3-O-benzyl-1,2-O-isopropylidene-α-D-glucopyranosiduronate 24

Methyl 3-O-benzyl-1,2-O-isopropylidene-α-D-glucofuranosiduronate 21 (3.43 g, 10.14 mmol) was dissolved in trifluoroacetic acid (90% aqueous, 20 mL) and stirred for 15 min at room temperature. The solvent was removed under reduced pressure and the residue coevaporated twice with water and twice with toluene. The residue was dissolved in DMF (10 mL) and 2-methoxypropene (10 mL, 100 mmol) and cooled to 0° C. A solution of (1S)-(+)-camphorsulfonic acid (230 mg, 1 mmol) in DMF (2 mL) was added and stirring was continued at 0° C. for 1 h and at room temperature overnight. Methanol (15 mL) was added and the mixture was stirred for 3 h at room temperature. Triethylamine (3 mL) was added and the mixture was concentrated. The residue was dissolved in $Et_2O$ and washed with water and twice with brine. The organic layer was dried over $Na_2SO_4$ and after filtration the solvent was removed under reduced pressure. Flash chromatography on silica gel (hexanes:EtOAc 9:1) afforded methyl 3-O-benzyl-1,2-O-isopropylidene-α-D-glucopyranosiduronate 24 (1.65 g, 4.88 mmol, 48%) as a colorless oil. $[α]^{24}_D$: +22.3 (c 1.13, $CH_2Cl_2$); IR (thin film on NaCl) 3520, 3037, 2987, 1752, 1455, 1169, 1105 cm$^{-1}$; $^1$H-NMR (500 MHz, $CDCl_3$) δ 7.34–7.26 (m, 5H, arom. H), 5.87 (d, J=2.7 Hz, 1H, H-1), 4.63 (d, J=11.9 Hz, 1H, benzyl-$CH_2$), 4.54 (d, J=11.6 Hz, 1H, benzyl-$CH_2$), 4.54 (d, J=3.7 Hz, 1H, H-5), 4.24–4.20 (m, 1H, H-4), 4.11–4.09 (m, 1H, H-3), 4.00 (dd, J=3.1 Hz, J=3.4 Hz, 1H, H-2), 3.58 (s, 3H, $OCH_3$), 3.51 (d, J=10.4 Hz, 1H, OH), 1.60 (s, 3H, $CH_3$), 1.37 (s, 3H, $CH_3$); $^{13}$C-NMR (125 MHz, $CDCl_3$) δ 170.3, 137.2, 128.6, 128.2, 127.8, 111.4, 94.4, 75.8, 75.5, 73.7, 72.4, 67.0, 52.2, 28.0, 25.9; FAB MS ($C_{17}H_{22}O_7$) m/z (M)$^+$ calcd 338.1366, obsd 338.1377. Further elution (hexanes-EtOAc 7:3) afforded 25 (1.1 g, 32%) as a colorless oil.

Methyl 3-O-benzyl-1,2-O-cyclopentylidene-α-D-glucopyranosiduronnate 26 and Methyl 3-O-benzyl-1,2-O-cyclopentylidene-α-D-glucofuranosiduronate 27

Methyl 3-O-benzyl-1,2-O-isopropylidene-α-D-glucofuranosiduronate 21 (3.34 g, 9.87 mmol) was dissolved in trifluoroacetic acid (90% aqueous, 20 ml) and stirred for 15 min at room temperature. The solvent was removed under reduced pressure and the residue coevaporated twice with water and twice with toluene. The residue was dissolved in DMF (10 mL) and methoxycyclopentene (7.1 g, 72 mmol) and cooled to 0° C. A solution of (1S)-(+)-camphorsulfonic acid (244 mg, 1.05 mmol) in DMF (2 mL) was added and stirring was continued at 0° C. for 1 h and at room temperature overnight. Methanol (5 mL) was added and the mixture was stirred for 30 min at room temperature. Triethylamine (3 mL) was added and the mixture was concentrated. The residue was dissolved in Et$_2$O and washed with water and brine (2×). The organic layer was dried over Na$_2$SO$_4$ and after filtration the solvent was removed under reduced pressure. Flash chromatography on silica gel (toluene-EtOAc 98.5:1.5) afforded methyl 3-O-benzyl-1,2-O-cyclopentylidene-α-D-glucopyranosiduronate 26 (2.05 g, 57%) as a colourless oil. $[α]^{24}_D$: +33.9 (c 1.48, CH$_2$Cl$_2$); IR (thin film on NaCl) 3510, 3032, 2955, 2873, 1750, 1454, 1436, 1336, 1206 cm$^{-1}$; $^1$H-NMR (500 MHz, CDCl$_3$) δ 7.37–7.27 (m, 5H, arom.), 5.84 (d, J=2.8 Hz, 1H, H-1), 4.66 (d, J=11.6 Hz, 1H, benzyl-CH$_2$), 4.57 (d, J=11.9 Hz, 1H, benzyl-CH$_2$), 4.52 (d, J=4.3 Hz, 1H, H-5), 4.23–4.19 (m, 1H, H-4), 4.04 (dd, J=3.0, 2.4 Hz, 1H, H-2), 4.00 (dd, J=3.4,3.1 Hz, 1H, H-3), 3.63 (s, 3H, OCH$_3$), 3.40 (d, J=9.5 Hz, 1H, OH), 2.14–2.08 (m, 1H, cyclopentenyl), 1.92–1.86 (m, 1H, cyclopentenyl), 1.79–1.62 (m, 6H, cyclopentenyl); $^{13}$C-NMR (125 MHz, CDCl$_3$) δ 170.5, 137.3, 128.6, 128.2, 127.8, 94.2, 75.9, 75.0, 74.2, 72.4, 67.4, 52.3, 37.7, 36.8, 23.5, 23.2; FAB MS (C$_{19}$H$_{24}$O$_7$) m/z (M)$^-$ calcd 364.1522, obsd 364.1534. Further elution (toluene:EtOAc 9:1) afforded methyl 3-O-benzyl-1,2-O-cyclopentylidene-α-D-glucofuranosiduronate 27 (1.04 g, 2.85 mmol, 29%) as a colorless oil. $[α]^{24}_D$: +0.7 (c 1.37, CH$_2$Cl$_2$); IR (thin film on NaCl) 3470, 2955, 2875, 1738, 1455, 1208 cm$^{-1}$; $^1$H-NMR (400 MHz, CDCl$_3$) δ 7.37–7.27 (m, 5H, arom.), 5.98 (d, J=4.0 Hz, 1H, H-1), 4.66 (d, J=11.5 Hz, 1H, benzyl-CH$_2$), 4.63–4.52 (m, 3H, benzyl-CH$_2$, H-3, H-5), 4.43 (dd, J=6.0 Hz, J=4.0 Hz, 1H, H-4), 4.16 (d, J=4.0 Hz, 1H, H-2), 3.73 (s, 3H, OCH$_3$), 3.36 (br. s, 1H, OH), 2.00–1.93 (m, 1H, cyclopentenyl), 1.86–1.76 (m, 1H, cyclopentenyl), 1.74–1.60 (m, 6H, cyclopentenyl); $^{13}$C-NMR (100 MHz, CDCl$_3$) δ 173.1, 136.9, 128.7, 128.3, 128.1, 121.9, 105.3, 83.3, 82.7, 80.1, 72.8, 70.1, 52.5, 37.1, 36.7, 23.4, 23.2; FAB MS (C$_{19}$H$_{24}$O$_7$) m/z (M)$^+$ calcd 364.1522, obsd 364.1530.

Methyl 3-O-benzyl-1,2-O-isopropylidene-β-L-idopyranosiduronate 28

Methyl 3-O-benzyl-L-idopyranosiduronate 23 (1.7 g, 5.70 mmol) was dissolved in DMF (6 mL) and 2-methoxypropene (10.7 mL, 114 mmol) was added. The mixture was cooled at 0° C. and (1S)-(+)-camphorsulfonic acid (132 mg, 0.57 mmol) in DMF (2 mL) was added dropwise under stirring. The mixture was stirred for 6 h at 0° C., then methanol (2 mL) was added and stirred for 30 min at 0° C. before the reaction was quenched by addition of triethylamine After dilution with EtOAc, the solution was washed with water. The organic layer was dried over MgSO$_4$ and evaporated. Flash chromatography on silica gel (toluene:EtOAc 99:1→96:4) afforded 28 (1.3 g, 3.84 mmol, 68%) as a yellow oil. $[α]^{24}_D$: -29.5 (c 1.00, CHCl$_3$); IR (thin film on NaCl) 2937, 1764, 1374, 843 cm$^{-1}$; $^1$H-NMR (500 MHz, CDCl$_3$) δ 7.40–7.30 (m, 5H, arom.), 5.35 (d, J=1.9 Hz, 1H, H-1), 4.71 (d, J=11.7 Hz, 1H, benzyl-CH$_2$), 4.63 (d, J=11.7 Hz, 1H, benzyl-CH$_2$), 4.49 (s, 1H, H-5), 4.12–4.10 (m, 1H, H-3), 4.0 (d, J=1.8 Hz, 1H, H-4), 3.97 (dd, J=1.9, 3.7 Hz, 1H, H-2), 3.80 (s, 3H, OCH$_3$), 3.12 (d, J=11.6 Hz, 1H, OH), 1.63 (s, 3H, CH$_3$), 1.38 (s, 3H, CH$_3$); $^{13}$C-NMR (125 MHz, CDCl$_3$) δ 169.4, 137.1, 128.8, 128.5, 128.0, 112.1, 96.5, 75.5, 73.4, 72.2, 67.4, 52.6, 28.4, 25.7; FAB MS (C$_{17}$H$_{22}$O$_7$) m/z (M)$^+$ calcd 338.1365, obsd 338.1357. Further elution (toluene:EtOAc 9:1) afforded 29 (382 mg, 20%) as a colorless oil.

Methyl 3-O-benzyl-1,2-O-cyclopentylidene-β-L-idopyranosiduronate 30 and Methyl 3-O-benzyl-1,2-O-cyclopentylidene-β-L-idofuranosiduronate 31

A mixture of (1S)-(+)-camphorsulfonic acid (77 mg, 0.33 mmol) and methoxycyclopentylidene (3.3 g, 33.5 mmol) in DMF (2 mL) was cooled to 0° C. A solution of methyl-3-O-benzyl-L-idopyranosiduronate 23 (1.0 g, 3.35 mmol) in DMF (1 mL) was added dropwise under stirring. The mixture was stirrred for 3 h at 0° C. and overnight at room temperature, after which methanol (2 mL) was added and stirred 30 minutes. The reaction was quenched by adding triethylamine After dilution with EtOAc, the solution was washed with water and dried over MgSO$_4$. After filtration the solvent was removed under reduced pressure and the syrup was purified by flash chromatography on silica gel (toluene:AcOEt 99:1→98:2) to yield 30 (684 mg, 1.88 mmol, 56%) as a yellow syrup. $[α]^{24}_D$: +10.9 (c 1.00, CHCl$_3$); IR (thin film on NaCl) 3534, 2954, 2111, 1764, 1437, 1336, 1120 cm$^{-1}$; $^1$H-NMR (500 MHz, CDCl$_3$) δ 7.40–7.30 (m, 5H, arom.), 5.35 (d, J=1.9 Hz, 1H, H-1), 4.70 (d, J=11.7 Hz, 1H, benzyl-CH$_2$), 4.63 (d, J=11.7 Hz, 1H, benzyl-CH$_2$), 4.50 (s, 1H, H-5), 4.11–4.09 (m, 1H, H-3), 4.07 (d, J=1.6 Hz, 1H, H-4), 3.88 (dd, J=2.1, 3.6 Hz, 1H, H-2), 3.80 (s, 3H, OCH$_3$), 3.10 (d, J=11.9 Hz, 1H, OH), 2.14–2.08 (m, 1H, cyclopentenyl), 2.23–2.16 (m, 1H, cyclopentenyl), 1.86–1.61 (m, 6H, cyclopentenyl); $^{13}$C-NMR (125 MHz, CDCl$_3$) δ 169.4, 137.2, 128.8, 128.5, 128.0, 121.5, 96.1, 75.7, 73.5, 72.9, 72.1, 67.4, 52.6, 38.3, 36.6, 23.5, 23.4; FAB MS (C$_{19}$H$_{24}$O$_7$) m/z (M)$^+$ calcd 364.1522, obsd 364.1530. Further elution (toluene:EtOAc 9:1) afforded methyl 3-O-benzyl-1,2-O-cyclopentylidene-α-D-idofuranosiduronate 31 (219 mg, 0.6 mmol, 18%) as a colorless oil. $[α]^{24}_D$: -13.9 (c 1.00, CHCl$_3$); IR (thin film on NaCl) 3485, 2954, 2874, 1738, 1453, 1338, 1207, 1120 cm$^{-1}$; $^1$H-NMR (500 MHz, CDCl$_3$) δ 7.38–7.30 (m, 5H, arom.), 5.97 (d, J=4.1 Hz, 1H, H-1), 4.74 (d, J=11.6 Hz, 1H, benzyl-CH$_2$), 4.64 (dd, J=1.2, 4.1 Hz, 1H, H-2), 4.57–450 (m, 2H, H-3, H-5), 4.53 (d, J=11.4 Hz, 1H, benzyl-CH$_2$,), 4.20 (dd, J=1.5, 4.7 Hz, 1H, H-4), 3.74 (s, 3H, OCH$_3$), 3.30 (d, J=3.3 Hz, 1H, OH), 2.00–1.91 (m, 1H, cyclopentenyl), 1.81–1.65 (m, 6H, cyclopentenyl); $^{13}$C-NMR (100 MHz, CDCl$_3$) δ 172.3, 137.0, 128.7, 128.3, 128.1, 122.2 105.1, 83.5, 83.0, 80.4, 72.5, 70.1, 52.8, 37.3, 37.1, 23.4, 23.3; FAB MS (C$_{19}$H$_{24}$O$_7$) m/z (M)$^+$ calcd 364.1522, obsd 364.1534.

6-O-Acetyl-2-azido-3-O-benzyl-4-O-tert-butyldimethylsilyl-2-deoxy-α-D-glucopyranosyl-(1→4)-methyl 3-O-benzyl-1,2-O-isopropylidene-α-D-glucopyranosiduronate 32

Coupling of 11 and 24

Compound 11 (1.87 g, 3.14 mmol) and 24 (850 mg, 2.51 mmol) were coevaporated with toluene (3×) and dissolved in anhydrous dichloromethane (50 mL). Freshly activated powdered 4 Å molecular sieves (1 g) were added and the mixture was stirred at room temperature for 1 h. The reaction mixture was cooled to -78° C. and tert-butyldimethylsilyl trifluoromethanesulfonate (72 μL, 0.314 mmol) was added dropwise. The mixture was warmed to room temperature over 2.5 h. Triethylamine (3 mL) was added, the mixture was filtered through a pad of Celite and the solvent was removed under reduced pressure. Flash chromatography on silica gel (hexanes:EtOAc 85:15) afforded 32 (1.68 g, 2.18 mmol, 86%) as a colorless foam.

Coupling of 10 and 24

Compound 10 (540 mg, 1.19 mmol) and 24 (362 mg, 1.07 mmol) were coevaporated with toluene (3×), dissolved in Et$_2$O (20 ml) and cooled to 0° C. To this mixture freshly activated 4 Å molecular sieves (1 g), SnCl$_2$ (229 mg, 1.21 mmol) and AgClO$_4$ (250 mg, 1.21 mmol) were added. This mixture was stirred for 90 min at 0° C., then warmed to 12° C. over 22 h. The mixture was filtered through a pad of Celite, washed with sat. NaHCO$_3$ and brine. The organic layer was dried over Na$_2$SO$_4$ and after filtration the solvent was removed under reduced pressure. Flash chromatography on silica gel (hexanes:EtOAc 9:1) afforded 32 (660 mg, 0.86 mmol, 80%) as a colorless foam. $[\alpha]^{24}_D$: +97.2 (c 2.55, CH$_2$Cl$_2$); IR (thin film on NaCl) 3032, 2953, 2930, 2858, 2106, 1746, 1455, 1372, 1250 cm$^{-1}$; $^1$H-NMR (500 MHz, CDCl$_3$) δ 7.40–7.27 (m, 10H, arom.), 5.78 (d, J=3.7 Hz, 1H, H-1B), 5.17 (d, J=3.7 Hz, 1H, H-1A), 4.88 (d, J=11.0 Hz, 1H, benzyl-CH$_2$), 4.78 (d, J=11.0 Hz, 1H, benzyl-CH$_2$), 4.68 (s, 2H, benzyl-CH$_2$), 4.59 (d, J=6.1 Hz, 1H, H-5B), 4.38 (dd, J=2.1, 11.9 Hz, 1H, H-6Aa), 4.25–4.21 (m, 2H, H-2B, H-4B), 4.09–4.05 (m, 2H, H-6Ab, H-3B), 3.89–3.85 (m, 1H, H-5A), 3.74 (dd, J=8.5, 10.4 Hz, 1H, H-3A), 3.71 (s, 3H, OCH$_3$), 3.63 (dd, J=8.5, 9.8 Hz, 1H, H-4A), 3.25 (dd, J=3.7, 10.4 Hz, 1H, H-2A), 2.08 (s, 3H, acetyl-CH$_3$), 1.63 (s, 3H, isopropylidene-CH$_3$), 1.39 (s, 3H, isopropylidene-CH$_3$), 0.89 (s, 9H, tert-butyl), 0.02 (s, 3H, CH$_3$), 0.00 (s, 3H, CH$_3$); $^{13}$C-NMR (MHz, CDCl$_3$) δ 170.9, 170.1, 138.1, 137.3, 128.6, 128.4, 128.2, 128.0, 127.7, 127.5, 111.0, 98.2, 95.7, 80.0, 76.0, 75.6, 75.1, 73.9, 72.3, 71.9, 71.3, 71.2, 63.6, 62.9, 52.5, 27.6, 26.0, 25.9, 21.0, 18.1, −3.6, −4.8; FAB MS (C$_{38}$H$_{53}$N$_3$O$_{12}$Si) m/z (M)$^+$ calcd 771.3399, obsd 771.3386.

6-O-Acetyl-2-azido-3-O-benzyl-4-O-tert-butyldimethylsilyl-2-deoxy-a-D-glucopyranosyl-(1→4)-methyl 3-O-benzyl-1,2-O-cyclopentylidene-α-D-glucopyranosiduronate 33

From 11

Compound 11 (870 mg, 1.46 mmol) and 26 (425 mg, 1.17 mmol) were coevaporated with toluene (3×) and dissolved in CH$_2$Cl$_2$ (20 mL). Freshly activated powdered 4 Å molecular sieves (500 mg) were added and the mixture was stirred at room temperature for 30 min. The mixture was cooled to −25° C. and tert-butyldimethylsilyl trifluoromethanesulfonate (33 μL, 0.146 mmol) was added dropwise. The reaction mixture was warmed to room temperature and stirred overnight. Triethylamine (3 mL) was added, the mixture was filtered through a pad of Celite and the solvent was removed under reduced pressure. Flash chromatography on silica gel (hexanes:EtOAc 95:5→99:1) afforded 33 (744 mg, 0.93 mmol, 80%) as a colorless foam. From 10: Compound 10 (610 mg, 1.35 mmol) and 26 (402 mg, 1.10 mmol) were coevaporated with toluene (3×), dissolved in Et$_2$O (20 ml) and cooled to 0° C. To this mixture freshly activated powdered 4 Å molecular sieves (1 g), SnCl$_2$ (260 mg, 1.37 mmol) and AgClO$_4$ (290 mg, 1.40 mmol) were added. The mixture was stirred for 8 h at 0° C., then warmed to 12° C. over 8 h. The mixture was filtered through a pad of Celite, washed with sat. NaHCO$_3$ and brine. The organic layer was dried over Na$_2$SO$_4$ and after filtration the solvent was removed under reduced pressure. Flash chromatography on silica gel (hexanes:EtOAc 95:5→9:1) afforded 33 (693 mg, 0.87 mmol, 79%) as a colorless foam. $[\alpha]^{24}_D$: +87.5 (c 1.20, CH$_2$Cl$_2$); IR (thin film on NaCl) 3025, 2954, 2849, 2105, 1746, 1455, 1250 cm$^{-1}$; $^1$H-NMR (500 MHz, CDCl$_3$) δ 7.40–7.27 (m, 10H, arom.), 5.74 (d, J=4.0 Hz, 1H, H-1B), 5.15 (d, J=3.4 Hz, 1H, H-1A), 4.87 (d, J=11.0 Hz, 1H, benzyl-CH$_2$), 4.79 (d, J=11.0 Hz, 1H, benzyl-CH$_2$), 4.70 (d, J=11.6 Hz, 1H, benzyl-CH$_2$), 4.67 (d, J=11.9 Hz, 1H, benzyl-CH$_2$), 4.59 (d, J=6.7 Hz, 1H, H-5B), 4.38 (dd, J=2.1, 11.9 Hz, 1H, H-6Aa), 4.26 (dd, J=3.1, 6.7 Hz, 1H, H-4B), 4.14 (dd, J=3.4, 4.0 Hz, 1H, H-2B), 4.08–4.04 (m, 2H, H-6Ab, H-3B), 3.89–3.84 (m, 1H, H-5A), 3.74 (dd, J=8.5, 10.4 Hz, 1H, H-3A), 3.71 (s, 3H, OCH$_3$), 3.64 (dd, J=9.2 Hz, J=8.9 Hz, 1H, H-4A), 3.24 (dd, J=3.7, 10.4 Hz, 1H, H-2A), 2.08–2.00 (m, 5H, acetyl-CH$_3$, cyclopentenyl), 1.79–1.62 (m, 6H, cyclopentenyl), 0.89 (s, 9H, tert-butyl), 0.02 (s, 3H, CH$_3$), 0.00 (s, 3H, CH$_3$); $^{13}$C-NMR (125 MHz, CDCl$_3$) δ 171.0, 170.2, 138.1, 137.3, 128.7, 128.5, 128.2, 128.0, 127.8, 127.5, 120.6, 98.0, 95.5, 80.0, 75.7, 75.3, 75.2, 74.0, 72.3, 71.4, 71.2, 71.2, 63.6, 62.9, 52.6, 37.0, 36.9, 26.0, 23.8, 23.3, 21.1, 18.1, −3.5, −4.8; FAB MS (C$_{40}$H$_{55}$N$_3$O$_{12}$Si) m/z (M)$^+$ calcd 797.3555, obsd 797.3578.

6-O-Acetyl-2-azido-3-O-benzyl-4-O-tert-butyldimethylsilyl-2-deoxy-α-D-glucopyranosyl-(1→4)-methyl 3-O-benzyl-D-glucopyranosiduronate 34

From 32

Compound 32 (1.68 g, 2.18 mmol) was dissolved in dichloroacetic acid (75% aqueous, 20 mL) and stirred at room temperature for 1 h. The reaction mixture was added slowly to sat. NaHCO$_3$ and extracted with CH$_2$Cl$_2$ (3×). The organic layer was dried over Na$_2$SO$_4$ and after filtration the solvent was removed under reduced pressure. Flash chromatography on silica gel (hexanes:EtOAc 1:1) afforded 34 (1.29 g, 1.86 mmol, 81%) colorless foam. From 33: Compound 33 (1.19 g, 1.49 mmol) was dissolved in dichloroacetic acid (50% aqueous, 15 mL) and stirred at room temperature for 2 h. The reaction mixture was added slowly to sat. NaHCO$_3$ and extracted with CH$_2$Cl$_2$ (3×). The organic layer was dried over Na$_2$SO$_4$ and after filtration the solvent was removed under reduced pressure. Flash chromatography on silica gel (hexanes:EtOAc 1:1) afforded 34 (980 mg, 1.34 mmol, 90%) as a colorless foam. FAB MS (C$_{35}$H$_{49}$N$_3$O$_{12}$Si) m/z (M)$^+$ calcd 731.3086, obsd 731.3107.

6-O-Acetyl-2-azido-3,4-di-O-benzyl-2-deoxy-α-D-glucopyranosyl-(1→4)-methyl 3-O-benzyl-1,2-O-isopropylidene-α-D-glucopyranosiduronate 35

Compound 18 (946 mg, 1.65 mmol) and 24 (451 mg, 1.33 mmol) were coevaporated with toluene (3×) and dissolved in CH$_2$Cl$_2$ (30 mL). Freshly activated powdered 4 Å molecular sieves (700 mg) were added and the mixture was stirred at room temperature for 1 h. The mixture was cooled to −78° C. and tert-butyldimethylsilyl trifluoromethanesulfonate (38 μL, 0.165 mmol) was added dropwise. The reacion mixture was warmed to room temperature and stirred overnight. Triethylamine (3 mL) was added and the mixture was filtered through a pad of Celite and the solvent was removed under reduced pressure. Flash chromatography (hexanes:EtOAc 8:2) afforded 35 (828 mg, 1.11 mmol, 83%) as a colorless oil. $[\alpha]^{24}_D$: +58.0 (c 1.53, CH$_2$Cl$_2$); IR (thin film on NaCl) 3029, 2938, 2017, 1743, 1454 cm$^{-1}$; $^1$H-NMR (500 MHz, CDCl$_3$) δ 7.41–7.27 (m, 15H, arom.), 5.72 (d, J=4.0 Hz, 1H, H-1B), 5.14 (d, J=3.7 Hz, 1H, H-1A), 4.90 (d, J=10.7 Hz, 1H, benzyl-CH$_2$), 4.87 (d, J=10.7 Hz, 1H, benzyl-CH$_2$), 4.86 (d, J=11.0 Hz, 1H, benzyl-CH$_2$), 4.70 (s, 2H, benzyl-CH$_2$), 4.59 (d, J=11.0 Hz, 1H, benzyl-CH$_2$), 4.48 (d, J=7.3 Hz, 1H, H-5B), 4.30 (dd, J=2.4, 11.9 Hz, 1H, H-6Aa), 4.28–4.22 (m, 3H, H-2B, H-4B, H-6Ab), 4.06 (at, J=3.7 Hz, 1H, H-3B), 4.00–3.92 (m, 2H, H-3A, H-5A), 3.73 (s, 3H, OCH$_3$), 3.54 (dd, J=8.8, 10.1 Hz, 1H, H-4A), 3.30 (dd, J=3.7, 10.4 Hz, 1H, H-2A), 2.05 (s, 3H, acetyl-CH$_3$), 1.62 (s, 3H, isopropylidene-CH$_3$), 1.39 (s, 3H, isopropylidene-CH$_3$); $^{13}$C-NMR (125 MHz, CDCl$_3$) δ 171.4, 170.7, 138.4, 138.2, 137.9, 129.3, 129.2, 128.8, 128.7, 128.7, 128.6, 128.5, 111.7, 98.3, 96.7, 80.5, 78.5, 77.1, 76.3, 76.1, 75.7, 74.4, 72.8, 72.1, 70.6, 63.9, 63.2, 53.2, 28.0, 26.5, 21.5; FAB MS (C$_{39}$H$_{45}$N$_3$O$_{12}$) m/z (M)$^+$ calcd 747.3003, obsd 747.3001.

6-O-Acetyl-2-azido-3,4-di-O-benzyl-2-deoxy-α-D-glucopyranosyl-(1→4)-methyl 3-O-benzyl-1,2-O-cyclopentylidene-α-D-glucopyranosiduronate 36

Compound 18 (855 mg, 1.50 mmol) and 26 (436 mg, 1.20 mmol) were coevaporated with toluene (3×) and dissolved in CH$_2$Cl$_2$ (20 mL). Freshly activated powdered 4 Å molecular sieves (250 mg) were added and the mixture was stirred at room temperature for 1 h. The mixture was cooled to −20° C. and tert-butyldimethylsilyl trifluoromethanesulfonate (100 μL, 0.44 mmol) was added dropwise. The reacion mixture was stirred for 2.5 h at −20° C. Triethylamine (3 mL) was added, the mixture was filtered through a pad of Celite and the solvent was removed under reduced pressure. Flash chromatography on silica gel (hexanes:EtOAc 85:15→8:2) afforded 36 (760 mg, 0.98 mmol, 82%) as a colorless oil. [α]$^{24}_D$: +62.3 (c 1.07, CH$_2$Cl$_2$); IR (thin film on NaCl) 2948, 2107, 1743, 1454, 1362 cm$^{-1}$; $^1$H-NMR (500 MHz, CDCl$_3$) δ 7.40–7.27 (m, 15H, arom), 5.69 (d, J=4.0 Hz, 1H, H-1B), 5.12 (d, J=3.7 Hz, 1H, H-1A), 4.90 (d, J=10.7 Hz, 1H, benzyl-CH$_2$), 4.87 (d, J=10.7 Hz, 1H, benzyl-CH$_2$), 4.86 (d, J=11.3 Hz, 1H, benzyl-CH$_2$), 4.70 (s, 2H, benzyl-CH$_2$), 4.60 (d, J=11.0 Hz, 1H, benzyl-CH$_2$), 4.48 (d, J=7.3 Hz, 1H, H-5B), 4.31 (dd, J=2.1, 12.2 Hz, 1H, H-6Aa), 4.28–4.24 (m, 2H, H-4B, H-6Ab), 4.18 (dd, J=3.7, 4.0 Hz, 1H, H-2B), 4.06 (at, J=3.4 Hz, 1H, H-3B), 4.01–3.93 (m, 2H, H-3A, H-5A), 3.74 (s, 3H, OCH$_3$), 3.55 (dd, J=8.8, 10.0 Hz, 1H, H-4A), 3.29 (dd, J=3.7, 10.4 Hz, 1H, H-2A), 2.09–2.03 (m, 5H, acetyl-CH$_3$, cyclopentenyl), 1.79–1.68 (m, 6H, cyclopentenyl); $^{13}$C-NMR (125 MHz, CDCl$_3$) δ 171.4, 170.7, 138.4, 138.2, 137.9, 129.3, 129.2, 128.8, 128.7, 128.7, 128.6, 128.5, 121.2, 98.1, 96.4, 80.5, 78.5, 76.8, 76.1, 76.0, 75.7, 74.5, 72.8, 71.6, 70.6, 63.8, 63.2, 53.2, 37.4, 37.3, 24.4, 23.8, 21.5; FAB MS (C$_{41}$H$_{47}$N$_3$O$_{12}$) m/z (M)$^+$ calcd 773.3160, obsd 773.3179.

6-O-acetyl-2-azido-3,4-di-O-benzyl-2-deoxy-α-D-glucopyranosyl)-(1→4)-methyl-3-O-benzyl-D-glucopyranosiduronate 37
From 35

Compound 35 (315 mg, 0.42 mmol) was dissolved in dichloroacetic acid (75% aqueous, 4 mL) and stirred at room temperature for 2 h. The reaction mixture was added slowly to sat. NaHCO$_3$ and extracted with CH$_2$Cl$_2$ (3×). The organic layer was dried over Na$_2$SO$_4$ and after filtration the solvent was remove under reduced pressure. Flash chromatography on silica gel (hexanes:EtOAc 1:1) afforded 37 (250 mg, 0.35 mmol, 84%) as a colorless foam. From 36: Compound 36 (836 mg, 1.08 mmol) was dissolved in dichloroacetic acid (75% aqueous 12 mL) and stirred at room temperature for 2 h. The reaction mixture was added slowly to sat. NaHCO$_3$ and extracted with CH$_2$Cl$_2$ (3×). The organic layer was dried over Na$_2$SO$_4$ and after filtration the solvent was removed under reduced pressure. Flash chromatography (hexanes:EtOAc 1:1) afforded 37 (619 mg, 0.87 mmol, 81%) as a colorless foam. FAB MS (C$_{36}$H$_{41}$N$_3$O$_{12}$) m/z (M)$^+$ calcd 707.2690, obsd 707.2678.

6-O-Acetyl-2-azido-3-O-benzyl-4-O-tert-butyldimethylsilyl-2-deoxy-α-D-glucopyranosyl-(1→4)-methyl 3-O-benzyl-1,2-O-isopropylidene-α-L-idopyranosiduronate 39

A mixture of 11 (1.38 g, 2.32 mmol) and 28 (627 mg, 1.9 mmol) was coevaporated with toluene (3×) and dried under vacuum for 1 h. The mixture was dissolved in CH$_2$Cl$_2$ (20 mL) and was stirred for 30 min at room temperature under argon in the presence of freshly activated powdered 4 Å molecular sieves (800 mg). After cooling the mixture to −30° C., tert-butyldimethylsilyltrifluoromethanesulfonate (1 M in dry CH$_2$Cl$_2$, 230 μL, 0.23 mmol) was added dropwise. The mixture was warmed to room temperature over 1 h. Triethylamine (4 mL) was added, the mixture was filtered through a pad of Celite and the solvent was removed under reduced pressure. The residue was purified by silica gel column chromatography (toluene:EtOAc 95:5→92:8) to yield 39 (1.30 g, 1.68 mmol, 91%) as a colorless glass. [α]$^{24}_D$: +93.3 (c 1, CHCl$_3$); IR (thin film on NaCl) 2890, 2100, 1740, 1020 cm−1; 1H-NMR (500 MHz, CDCl3) 7.38–1.20 (m, 10H, arom.), 5.28 (d, J=2.4 Hz, 1H, H-1B), 4.93 (d, J=3.0 Hz, 1H, H-1A), 4.76 (d, J=11.0 Hz, 1H, benzyl-CH$_2$), 4.65 (d, J=11.0 Hz, 1H, benzyl-CH$_2$), 4.61 (s, 2H, H-6Aa, benzyl-CH$_2$) 4.41–4.36 (m, 2H, H-3A, benzyl-CH$_2$), 4.13 (t, J=2.1 Hz, 1H, H-3B), 3.99 (s, 1H, H-5B), 3.95 (dd, J=3.0, 12.2 Hz, 1H, H-6Ab), 3.91 (s, 1H, H-4B, H-6Ab), 3.74–3.71 (m, 1H, H-4A), 3.71 (s, 3H, OCH$_3$), 3.61–3.59 (m, 2H, H-2B, H-5A) 3.30 (dd, J=3.3, 9.5 Hz, 1H, H-2A), 2.08 (s, 3H, acetyl-CH$_3$), 1.98 (s, 3H, acetyl-CH$_3$), 1.57 (s, 3H, isopropyl-CH$_3$), 1.33 (s, 3H, isopropyl-CH$_3$), 0.78 (s, 9H, tert-butyl), −0.10 (s, 6H, CH$_3$); $^{13}$C-NMR (125 MHz, CDCl$_3$) δ 170.8, 169.0, 138.2, 137.1 128.8, 128.4, 128.0 127.9, 127.7, 127.6, 112.2, 98.1, 97.1, 80.1, 97.3, 75.4, 75.2, 73.5, 72.9, 72.8, 71.5, 71.3, 70.6, 68.9, 64.6, 62.5, 52.5, 28.3, 26.3, 26.0, 21.1, 18.1, −3.6, −5.0; FAB MS (C$_{38}$H$_{53}$N$_3$O$_{12}$Si) m/z (M)$^+$ calcd 771.3399, obsd 771.3415.

3,6-Di-O-acetyl-2-azido-4-O-tert-butyldimethylsilyl-2-deoxy-α-D-glucopyranosyl-(1→4)-methyl 3-O-benzyl-1,2-O-isopropylidene-μ-L-idopyranosiduronate 40

A mixture of 38 (500 mg, 0.91 mmol) and 28 (241 mg, 0.71 mmol) was coevaporated with toluene (3×) and dried under vacuum for 1 h. The mixture was dissolved in CH$_2$Cl$_2$ (15 mL) and was stirred for 30 min at room temperature under argon in the presence of freshly activated powdered 4 Å molecular sieves (400 mg). After cooling the mixture to −30° C., tert-butyldimethylsilyltrifluoromethanesulfonate (0.1 M in dry CH$_2$Cl$_2$, 1 mL, 0.1 mmol) was added dropwise. The mixture was warmed to 0° C. over 1 h. Triethylamine (1.8 mL) was added, the mixture was filtered through a pad of Celite and the solvent was removed under reduced pressure. The residue was purified by silica gel column chromatography (toluene:EtOAc 95:5→92:8) to yield 40 (463 mg, 0.64 mmol, 90%) as a colorless glass. [α]$^{24}_D$: +87.4 (c 1.00, CHCl$_3$); IR (thin film on NaCl) 2880, 2086, 1731, 1440, 1054 cm$^{-1}$; $^1$H-NMR (500 MHz, CDCl$_3$) δ 7.38–7.32 (m, 5H, arom.), 5.34 (d, J=2.1 Hz, 1H, H-1B), 5.32–5.36 (dd, 1H, H-3A), 4.93 (d, J=3.0 Hz, 1H, H-1A), 4.70 (d, J=11.6 Hz, 1H, benzyl-CH$_2$), 4.67 (d, J=11.6 Hz, 1H, benzyl-CH$_2$), 4.50 (dd, J=2.1, 12.5 Hz, 1H, H-6Aa), 4.42 (d, J=1.5 Hz, 1H, H-5B), 4.27 (t, J=2.1 Hz, 1H, H-3B), 4.06–4.02 (m, 2H, H-4B, H-6Ab), 3.98–3.94 (m, 2H, H-2B, H-5A), 3.80–3.74 (m, 1H, H-4A), 3.79 (s, 3H, OCH$_3$), 3.17 (dd, J=10.7, 3.4 Hz, 1H, H-2A), 2.08 (s, 3H, acetyl-CH$_3$), 2.00 (s, 3H, acetyl-CH$_3$), 1.64 (s, 3H, isopropyl-CH$_3$), 1.39 (s, 3H, isopropyl-CH$_3$), 0.81 (s, 9H, tert-butyl), 0.03 (s, 3H, CH$_3$), 0.01 (s, 3H, CH$_3$); $^{13}$C-NMR (125 MHz, CDCl$_3$) δ 170.6, 169.8, 169.1, 137.3, 128.8, 128.4, 128.1, 112.5, 99.1, 97.3, 75.7, 74.8, 73.9, 73.0, 72.8, 71.3, 71.3, 68.9, 62.4, 62.3, 52.7, 28.1, 26.2, 25.7, 21.5, 21.1, 18.0, −3.9, −4.9; FAB MS (C$_{33}$H$_{49}$N$_3$O$_{13}$Si) m/z (M)$^+$ calcd 723.3035, obsd 723.3058.

3,6-Di-O-acetyl-2-azido-4-O-tert-butyldimethylsilyl-2-deoxy-β-D-glucopyranosyl-(1→4)-methyl 3-O-benzyl-1,2-O-cyclopentylidene-β-L-idopyranosiduronate 41

A mixture of 38 (200 mg, 0.36 mmol) and 13 (95 mg, 0.28 mmol) was coevaporated with toluene (3×) and dried under vacuum for 1 h. The mixture was dissolved in CH$_2$Cl$_2$ (5 mL) and was stirred for 30 min at room temperature under argon in the presence of freshly activated powdered 4 Å molecular sieves (150 mg). After cooling the mixture to −30° C., tert-butyldimethylsilyltrifluoromethanesulfonate (0.1 M in dry $CH_2Cl_2$, 0.4 mL, 0.04 mmol) was added dropwise. The mixture was warmed to 0° C. over 1 h. Triethylamine (0.7 mL) was added, the mixture was filtered through a pad of Celite and the solvent was removed under reduced pressure. The residue was purified by silica gel column chromatography (toluene:EtOAc 96:3→90:10) to yield 41 (217 mg, 0.29 mmol, 88%) as a colorless glass. $[\alpha]^{24}_D$: +75.6 (c 1.00, $CH_2Cl_2$); IR (thin film on NaCl) 2955, 2858, 2109, 1744, 1455 $cm^{-1}$; $^1H$-NMR (400 MHz, $CDCl_3$) δ 7.38–7.30 (m, 5H, arom.), 5.34–5.29 (m, 2H, H-1B, H-3A), 4.68 (t, J=12.0 Hz, 2H, benzyl-$CH_2$), 4.51 (m, 1H, H-6Aa), 4.46 (d, J=1.5 Hz 1H, H-5B), 4.28 (dd, J=2.1, 2.9 Hz, 1H, H-3B), 4.13 (t, 1H, H-4B), 4.07–4.02 (m, 2H, H-5A, H-6Ab), 3.87 (t, 1H, H-2B), 3.80–3.74 (m, 1H, H-4A), 3.77 (s, 3H, $OCH_3$), 3.07 (dd, J=3.4, 10.6 Hz, 1H, H-2A), 2.13 (s, 3H, acetyl-$CH_3$), 2.06 (s, 3H, acetyl-$CH_3$), 2.09–04 (m, 2H, cyclopentenyl), 1.78–1.63 (m, 6H, cyclopentenyl), 0.82 (s, 9H, tert-butyl), 0.04 (s, 3H, $CH_3$), 0.02 (s, 3H, $CH_3$); $^{13}C$-NMR (125 MHz, $CDCl_3$) δ 170.6, 169.8, 169.1, 137.3, 128.7, 128.3, 121.7, 98.9, 96.9, 76.9, 75.8, 74.4, 74.1, 73.0, 72.7, 71.1, 71.0, 68.9, 62.3, 62.1, 52.6, 37.6, 36.9, 25.7, 23.5, 21.5, 21.0, 18.0, −3.9, −4.9; FAB MS ($C_{35}H_{51}N_3O_{13}Si$) m/z $(M)^+$ calcd 749.3191, obsd 749.3197.

6-O-Acetyl-2-azido-3-O-benzyl-4-O-tert-butyldimethylsilyl-2-deoxy-α-D-glucopyranosyl-(1→4)-methyl 3-O-benzyl-L-idopyranosiduronate 42

A solution of 39 (1.20 g, 1.55 mmol) in dichloroacetic acid (40 mL, 60% aq) was stirred at room temperature for 3 h, diluted with water and neutralized with $NaHCO_3$ (24 g). The aqueous phase was extracted three times with $CH_2Cl_2$. The combined organic phases were dried over $MgSO_4$. After filtration the solvent was removed under reduced pressure to afford 42 (1.05 g, 1.4 mmol, 92%) as an essentially pure white solid. Compound 42 can be further purified by silica gel column chromatography. (hexane:EtOAc 70:30). FAB MS ($C_{35}H_{49}N_3O_{12}Si$) m/z $(M)^+$ calcd 731.3086, obsd 731.3002.

3,16-Di-O-acetyl-2-azido-4-O-tert-butyldimethlylsilyl-2-deoxy-α-D-glucopyranosyl-(1→4)-methyl 3-O-benzyl-L-idopyranosiduronate 43
From 40

A solution of 40 (770 mg, 1.06 mmol) in dichloroacetic acid (10 mL, 60% aq) was stirred at room temperature for 3 h, diluted with water and neutralized with $NaHCO_3$ (7 g). The aqueous phase was extracted three times with $CH_2Cl_2$ and the combined organic phases were dried over $MgSO_4$. After filtration the solvent was removed under reduced pressure to afford 43 (647 mg, 0.95 mmol, 89%) as a white solid. Compound 43 can be further purified by silica gel column chromatography (hexane:EtOAc 70:30). FAB MS ($C_{30}H_{45}N_3O_{13}Si$) m/z $(M)^+$ calcd 683.2722, obsd 683.2743.
From 41: A solution of 41 (200 mg, 0.27 mmol) in dichloroacetic acid (3 mL, 60% aq) was stirred at room temperature for 3 h, diluted with water and neutralized with $NaHCO_3$ (7 g). The aqueous phase was washed three times with $CH_2Cl_2$. The combined organic phases were dried over $MgSO_4$. After filtration the solvent was removed under reduced pressure to afford 43 (160 mg, 0.23 mmol, 88%) as an essentially pure white solid.

6-O-Acetyl-2-azido 3-O-benzyl-4-O-tert-butyldimethylsilyl-2-deoxy-α-D-glucopyranosyl-(1→4)-methyl 3-O-benzyl-1,2-O-monochloroacetyl-α/β-D-glucopyranosiduronate 44

Pyridine (2.1 mL, 24 mmol), monochloroacetic anhydride (3.0 g, 9.00 mmol) and DMAP (19 mg, 0.157 mmol) were added to a solution of 34 (1.3 g, 1.57 mmol) in $CH_2Cl_2$ (21 mL). The solution was stirred at room temperature for 6 h, water was added and the mixture was stirred for one additional hour. The organic phase was washed with sat. $NaHCO_3$, water and aqueous HCl (10%), dried over $MgSO_4$ and filtered. The solvent was removed under reduced pressure and the residue was purified by silica gel column chromatography (hexane:EtOAc 90:20) to yield 44 (1.5 g, 1.7 mmol, 96%) as a colorless syrup. FAB MS ($C_{39}H_{51}Cl_2N_3O_{14}Si$) m/z $(M)^+$ calcd 883.2517, obsd 883.2506.

6-O-Acetyl-2-azido-3,4-di-O-benzyl-2-deoxy-α-D-glucopyranosyl-(1→4)-methyl 3-O-benzyl-1,2-O-monochloroacetyl-α/β-D-glucopyranosiduronate 45

Pyridine (0.65 mL, 7.4 mmol), monochloroacetic anhydride (820 mg, 2.5 mmol) and DMAP (7 mg, 0.06 mmol) were added to a solution of 37 (400 mg, 0.6 mmol) in $CH_2Cl_2$ (6.5 mL). The solution was stirred at room temperature for 6 h, water was added and the mixture was stirred for one additional hour. The organic phase was washed with saturated solution of $NaHCO_3$, water and 10% HCl, dried over $MgSO_4$ and filtered. The solvent was removed under reduced pressure and the residue was purified by silica gel column chromatography (hexane:EtOAc 90:20) to yield 45 (452 mg, 0.53 mmol 93%) as a colorless syrup. FAB MS ($C_{40}H_{43}Cl_2N_3O_{14}$) m/z $(M)^+$ calcd 859.2122, obsd 859.2113.

6-O-Acetyl-2-azido 3-O-benzyl-4-O-tert-butyldimethylsilyl-2-deoxy-α-D-glucopyranosyl-(1→4)-methyl-3-O-benzyl-2-O-monochloroacetyl-α-D-glucopyranosyluronate trichloroacetimidate 46
From 44

Benzylamine (70 μL, 0.63 mmol) was added in three portions, every 2 h, to a solution of 44 (1 g, 1.2 mmol) $Et_2O$ (40 mL) at 0° C. and kept overnight at −20° C. The mixture was diluted with $CH_2Cl_2$, filtered and washed with aqueous HCl (10%). The organic phase was dried over $MgSO_4$, filtered and the solvent was removed under reduced pressure. Flash chromatography on silica gel (hexane:EtOAc 90:10→80:20) afforded 6-O-acetyl-2-azido-3-O-benzyl-4-O-tert-butyldimethylsilyl-2-deoxy-α-D-glucopyranosyl-(1→4)-methyl 3-O-benzyl-2-O-monochloroacetyl-D-glucopyranosiduronate (704 mg, 0.87 mmol, 75%) as a white solid. FAB MS ($C_{37}H_{50}ClN_3O_{13}Si$) m/z $(M)^+$ calcd 807.2801, obsd 807.2796.
From 50

A mixture of tetrabutylammonium fluoride (1.0 M in THF, 0.6 mL) and glacial acetic acid (55 μl, 0.9 mmol) was added dropwise to a solution of 50 (539 mg, 0.58 mmol) in THF (6 mL) under nitrogen at 0° C. The reaction mixture was warmed to room temperature, stirred for 1.5 h and quenched with brine. After dilution with $CH_2Cl_2$, the two phases were separated. The organic phase was dried over $MgSO_4$, filtered and the solvent was removed under reduced pressure. The crude material was purified by silica gel column chromatography (hexane:EtOAc 90:10→80:20) to yield 6-O-acetyl-2-azido-3-O-benzyl-4-O-tert-butyldimethylsilyl-2-deoxy-α-D-glucopyranosyl-(1→4)-methyl 3-O-benzyl-2-O-monochloroacetyl-α/β-D-glucopyranosiduronate (198 mg, 43%) as a white solid.

A solution of 6-O-acetyl-2-azido-3-O-benzyl-4-O-tert-butyldimethylsilyl-2-deoxy-α-D-glucopyranosyl-(1→4)-methyl 3-O-benzyl-2-O-monochloroacetyl-D-glucopyranosiduronate (540 mg, 0.7 mmol) and trichloroacetonitrile (2 mL, 19.2 mmol) in $CH_2Cl_2$ (14 mL) containing freshly activated 4 Å molecular sieves (100 mg), was stirred 30 minutes at room temperature. After cooling to 0° C., before DBU (45 μl, 0.3 mmol) was added. The mixture was allowed to reach room temperature after 1 h the mixture was filtered through a pad of Celite and concentrated. The residue was purified by silica gel column chromatography (hexane:EtOAc 85:15) to yield 46 (546 mg, 0.57 mmol, 85%) as a white solid. $[\alpha]^{24}_D$: +81.5 (c 1.00, CHCl$_3$); IR (thin film on NaCl) 2930, 2106, 1745, 1678, 1252, 1029 cm$^{-1}$; $^1$H-NMR (300 MHz, CDCl$_3$) δ 8.69 (s, 1H, NH), 7.36–7.26 (m, 10H, H-arom.), 6.56 (d, J=3.2 Hz, H-1B), 5.60 (d, J=3.6 Hz, 1H, H-1A), 5.14–5.19 (m, 1H, H-2B), 4.96–4.78 (m, 4H, benzyl-CH$_2$), 4.49 (d, 1H, H-5B), 4.35 (dd, J=11.8 Hz, 1H, H-6aA), 4.28–4.25 (m, 2H, H-4B, H-3B), 4.04 (dd, J=3.8, 12.1 Hz, 1H, H-6bA), 3.99 (d, J=9.5 Hz, H-5B), 3.84–3.76 (m, 2H, CH$_2$Cl), 3.79 (s, 3H, OCH$_3$), 3.72–3.61 (m, 2H, H-3A, H-5A), 3.50 (m, 1H, H-4A), 3.26 (dd, J=3.6, 10.2 Hz, 1H, H-2A), 2.10 (s, 3H, COCH$_3$), 0.88 (s, 9H, C(CH$_3$)$_3$), −0.01 (s, 6H, SiCH$_3$); $^{13}$C-NMR (125 MHz, CDCl$_3$) δ 171.0, 168.5, 166.5, 160.8, 138.0, 137.9, 128.8, 128.5, 128.1, 127.8, 127.5, 127.4, 98.2, 92.9, 80.1, 79.6, 75.5, 75.3, 75.0, 74.3, 72.6, 71.3, 70.9, 63.7, 62.5, 53.1, 40.3, 26.0, 21.1, 18.2, −3.5, −4.8; FAB MS (C$_{39}$H$_{50}$Cl$_4$N$_4$O$_{13}$Si) m/z (M)$^+$ calcd 950.1898, obsd 950.1892.

O-(6-O-Acetyl-2-azido 3,4-di-O-benzyl-2-deoxy-α-D-glucopyranosyl-(1→4)-methyl-3-O-benzyl-2-O-monochloroacetyl-α-glucopyranosyduronate) trichloroacetimidate 47

Benzylamine (70 μL, 0.63 mmol) was added in three portions, every 2 h, to a solution of 45 (400 mg, 0.46 mmol) in EtO (25 mL) at 0° C. and kept overnight at −20° C. The mixture was diluted with CH$_2$Cl$_2$, filtered and washed with aqueous HCl (10%). The organic phase was dried over MgSO$_4$, filtered and the solvent was removed under reduced pressure. Flash chromatography on silica gel (hexane:EtOAc 90:10→80:20) afforded 6-O-acetyl-2-azido-3,4-di-O-benzyl-2-deoxy-α-D-glucopyranosyl-(1→4)-methyl 3-O-benzyl-2-O-monochloroacetyl-D-glucopyranosiduronate (277 mg, 0.35 mmol, 76%) as a white solid. FAB MS (C$_{38}$H$_{42}$ClN$_3$O$_{13}$Si) m/z (M)$^+$ calcd 783.2406 obsd 783.2400.

A solution of 6-O-acetyl-2-azido-3,4-di-O-benzyl-2-deoxy-α-D-glucopyranosyl-(1→4)-methyl 3-O-benzyl-2-O-monochloroacetyl-D-glucopyranosiduronate (226 mg, 0.292 mmol) and trichloroacetonitrile (0.790 mL, 7.6 mmol) in CH$_2$Cl$_2$ (7 mL) containing freshly activated 4 Å molecular sieves (100 mg), was stirred 30 minutes at room temperature. After cooling to 0° C., DBU (5 μl, 0.03 mmol) was added. The mixture was allowed to reach room temperature and after 1 h it was filtered through a pad of Celite and concentrated. The residue was purified by silica gel column chromatography (hexane:EtOAc 85:15) to yield 47 (240 mg, 0.26 mmol, 90%) as a white solid. FAB MS (C$_{40}$H$_{42}$Cl$_4$N$_4$O$_{13}$Si) m/z (M)$^+$ calcd 926.1502, obsd 926.1514; $^1$H-NMR (500 MHz, CDCl$_3$) 8.70 (s, 1H, NH), 7.38–7.27 (m, 15H, arom.), 6.56 (d, J=3.4 Hz, 1H, H-1B) 5.53 (d, J=3.7 Hz, 1H, H-1A), 5.17–5.14 (m, 1H, H-2B), 4.99–4.78 (m, 5H, benzyl-CH$_2$), 4.46–4.42 (m, 2H, H-4B, benzyl-CH$_2$), 4.28–4.19 (m, 4H, H-3B, H-5B, H-6aA, H-6Ab), 3.97–3.90 (m, 1H, H-3A), 3.84–3.70 (m, 2H, CH$_2$Cl), 3.77 (s, 3H, OCH$_3$), 3.62–3.49 (m, 2H, H-4A, H-5A), 3.32 (dd, J=3.8, 10.4 Hz, 1H, H-2A), 2.04 (s, 3H, acetyl-CH$_3$); $^{13}$C-NMR (100 MHz, CDCl$_3$) 170.8, 168.4, 166.5, 160.7, 137.9, 137.8, 137.7, 137.6, 129.0, 128.7, 128.6, 128.5, 128.4, 128.2, 128.1, 128.0, 98.4, 92.9, 90.7, 80.1, 79.3, 77.6, 77.5, 75.7, 75.6, 75.2, 75.1, 73.5, 72.6, 70.1, 63.3, 62.3, 53.2, 40.3, 21.0.

tert-Butyldimethylsilyl (6-O-acetyl-2-azido-3-O-benzyl-4-O-tert-butyldimethylsilyl-2-deoxy-α-D-glucopyranosyl)-(1→4)-methyl 3-O-benzyl-2-O-levulinyl-β-D-glucopyranosiduronate 48

Compound 34 (1.12 g, 1.53 mmol) and imidazole (208 mg, 3.05 mmol) were dissolved in CH$_2$Cl$_2$ (10 mL) and cooled to −15° C. tert-Butyldimethylsilyl-chloride (253 mg, 1.68 mmol) was added to the mixture and stirring was continued at −15° C. After 5 h tert-butyldimethylsilylchloride (125 mg, 0.83 mmol) was added and after 6 h imidazole (100 mg, 1.47 mmol) and tert-butyldimethylsilylchloride (253 mg, 1.68 mmol) were added. After 18 h one additional portion of tert-butyldimethylsilylchloride (70 mg, 0.46 mmol) was added. After 40 h, water was added and the mixture was warmed to room temperature. After dilution with EtOAc the mixture was washed with sat. NaHCO$_3$ and brine. The organic layer was dried over Na$_2$SO$_4$ and after filtration the solvent was removed under reduced pressure. Flash chromatography on silica gel (hexanes:EtOAc 9:1→8:2) afforded tert-butyldimethylsilyl (6-O-acetyl-2-azido-3-O-benzyl-4-O-tert-butyldimethylsilyl-2-deoxy-α-D-glucopyranosyl)-(1→4)-methyl 3-O-benzyl-β-D-glucopyranosiduronate, (1.08 g, 1.28 mmol, 84%) as a colorless foam. $[\alpha]^{24}_D$: +65.9 (c 1.55, CH$_2$Cl$_2$); IR (thin film on NaCl) 3475, 3031, 2953, 2857, 2106, 1747, 1472, 1254 cm$^{-1}$; $^1$H-NMR (500 MHz, CDCl$_3$) δ 7.41–7.27 (m, 10H, arom.), 5.64 (d, J=3.7 Hz, 1H, H-1A), 5.07 (d, J=11.0 Hz, 1H, benzyl-CH$_2$), 4.89 (d, J=11.0 Hz, 1H, benzyl-CH$_2$), 4.83 (d, J=11.0 Hz, 1H, benzyl-CH$_2$), 4.81 (d, J=11.0 Hz, 1H, benzyl-CH$_2$), 4.59 (d, J=7.3 Hz, 1H, H-1B), 4.35 (dd, J=2.1, 11.9 Hz, 1H, H-6aA), 4.14 (dd, J=8.8, 9.5 Hz, 1H, H-4B), 4.07 (dd, J=3.7, 12.2 Hz, 1H, H-6Ab), 3.99 (d, J=9.8 Hz, 1H, H-5B), 3.79 (s, 3H, OCH$_3$), 3.76 (at, J=8.8 Hz, 1H, H-3B), 3.69–3.63 (m, 2H, H-3A, H-4A), 3.57 (ddd, J=9.5, 9.2, 2.1 Hz, 1H, H-2B), 3.52–3.49 (m, 1H, H-5A), 3.28–3.22 (m, 1H, H-2A), 2.31 (d, J=2.1 Hz, 1H, OH), 2.10 (s, 3H, acetyl-CH$_3$), 0.92 (s, 9H, tert-butyl), 0.89 (s, 9H, tert-butyl), 0.15 (s, 6H, 2 x CH$_3$), 0.00 (s, 6H, 2×CH$_3$); $^{13}$C-NMR (125 MHz, CDCl$_3$) δ 171.0, 168.8, 138.5, 138.1, 128.6, 128.5, 127.9, 127.8, 127.7, 127.5, 98.0, 97.7, 83.9, 80.2, 76.5, 75.2, 74.9, 74.8, 74.7, 71.0, 70.8, 63.8, 62.6, 52.8, 26.0, 25.9, 21.1, 18.2, 18.1, −3.5, −4.1, −4.9, −5.0; FAB MS (C$_{41}$H$_{63}$N$_3$O$_{12}$Si$_2$) m/z (M)$^+$ calcd 845.3950, obsd 845.3925.

tert-Butyldimethylsilyl (6-O-acetyl-2-azido-3-O-benzyl-4-O-tert-butyldimethylsilyl-2-deoxy-α-D-glucopyranosyl)-(1→4)-methyl 3-O-benzyl-β-D-glucopyranosiduronate (998 mg, 1.18 mmol) and DMAP (432 mg, 3.54 mmol) were dissolved in CH$_2$Cl$_2$ (10 mL) and a solution of levulinic anhydride (500 mg, 2.34 mmol) in CH$_2$Cl$_2$ (5 mL) was added. The reaction mixture was stirred for 2 h at room temperature and concentrated. Flash chromatography on silica gel (hexanes:EtOAc 8:2) afforded 48 (1.08 g, 1.14 mmol, 97%) as a colorless foam. $^1$H-NMR (400 MHz, CDCl$_3$) δ 7.39–7.24 (m, 10H, arom.), 5.53 (d, J=3.6 Hz, 1H, H-1A), 5.04 (dd, J=7.3, 8.8 Hz, 1H, H-2B), 4.90–4.73 (m, 5H, 4×benzyl-CH$_2$, H-1B), 4.37 (dd J=1.8, 11.9 Hz, 1H, H-6aA), 4.26 (at, J=9.2, 9.0 Hz, 1H, H-4B), 4.07–4.00 (m, 2H, H-6Ab, H-5B), 3.86 (dd, J=8.8, 8.7 Hz, 1H, H-3B), 3.79 (s, 3H, OCH$_3$), 3.68–3.61 (m, 2H, H-3A, H-4A), 3.55–3.52 (m, 1H, H-5A), 3.25 (dd, J=3.7, 9.9 Hz, 1H, H-2A), 2.68–2.63 (m, 2H, Lev-CH$_2$), 2.53–2.48 (m, 2H, Lev-CH$_2$), 2.12 (s, 3H, Lev-CH$_3$), 2.08 (s, 3H, acetyl), 0.89 (s, 9H, tert-butyl), 0.87 (s, 9H, tert-butyl), 0.12 (s, 3H, CH$_3$), 0.10 (s, 3H, CH$_3$), 0.00 (s, 3H, CH$_3$), −0.03 (s, 3H, CH$_3$); $^{13}$C-NMR (100 MHz, CDCl$_3$) δ 206.0, 171.2, 170.8, 168.5, 138.0, 137.9, 128.5, 128.4, 127.8, 127.7, 127.6, 127.4, 97.5, 96.1, 82.5, 80.2, 75.2, 75.1, 74.7, 74.5, 74.1, 71.1, 70.8, 63.8, 62.5, 52.7, 37.8, 29.9, 28.0, 26.0, 25.6, 21.0, 18.1, 17.9, −3.6, −4.2, −5.0, −5.2; FAB MS ($C_{46}H_{69}N_3O_{14}Si_2$) m/z (M)$^+$ calcd 943.4318, obsd 943.4332.

tert-Butyldimethylsilyl (6-O-acetyl-2-azido-3-O-benzyl-4-O-tert-butyldimethylsilyl-2-deoxy-α-D-glucopyranosyl)-(1→4)-methyl 2-O-allyloxycarbonyl-3-O-benzyl-β-D-glucopyranosiduronate 49 tert-Butyldimethylsilyl (6-O-acetyl-2-azido-3-O-benzyl-4-O-tert-butyldimethylsilyl-2-deoxy-α-D-glucopyranosyl)-(1→4)-methyl 3-O-benzyl-β-D-glucopyranosiduronate, (for the experimental procedure, please see the procedure to prepare compound 48) (350 mg, 0.414 mmol) and DMAP (1.01 g, 8.28 mmol) were dissolved in $CH_2Cl_2$ (10 mL) and cooled to −70° C. Allyloxycarbonylchloride (800 μl, 7.54 mmol) was added in three equal portions every 2 h. After the addition was complete the mixture was warmed to room temperature and stirred overnight. The mixture was poured into EtOAc and washed with 1 N HCl, brine and sat. NaHCO$_3$. The organic layer was dried over Na$_2$SO$_4$, filtered and the solvent was removed under reduced pressure. Flash chromatography on silica gel (hexanes:EtOAc 9:1→85:15) afforded 49 (347 mg, 0.373 mmol, 90%) as a colorless oil. $[\alpha]^{24}_D$: +82.6 (c 1.04, $CH_2Cl_2$); IR (thin film on NaCl) 3037, 2929, 2857, 2106, 1758, 1454, 1252 cm$^{-1}$; $^1$H-NMR (500 MHz, CDCl$_3$) δ 7.39–7.26 (m, 10H, arom.), 5.91–5.82 (m, 1H, alloc), 5.55 (d, J=3.7 Hz, 1H, H-1A), 5.35–5.30 (m, 1H, alloc), 5.25–5.22 (m, 1H, alloc), 4.89–4.71 (m, 6H, H-1B, H-2B, 4×benzyl-CH$_2$), 4.62–4.53 (m, 2H, alloc), 4.34 (dd, J=2.1, 11.9 Hz, 1H, H-6Aa), 4.22 (dd, J=9.5, 9.2 Hz, 1H, H-4B), 4.05 (dd, J=3.7, 12.2 Hz, 1H, H-6Ab), 3.99 (d, J=9.8 Hz, 1H, H-5B), 3.85 (d, J=9.2 Hz, 1H, H-3B), 3.80 (s, 3H, OCH$_3$), 3.68–3.61 (m, 2H, H-3A, H-4A), 3.52–3.49 (m, 1H, H-5A), 3.29–3.25 (m, 1H, H-2A), 2.10 (s, 3H, acetyl-CH$_3$), 0.89 (s, 9H, tert-butyl), 0.87 (s, 9H, tert-butyl), 0.12 (s, 3H, CH$_3$), 0.10 (s, 3H, CH$_3$), 0.00 (s, 6H, 2×CH$_3$); $^{13}$C-NMR (125 MHz, CDCl$_3$) δ 171.0, 168.5, 154.1, 138.0, 137.8, 131.4, 128.6, 128.5, 127.9, 127.8, 127.7, 127.5, 119.6, 97.8, 96.1, 82.6, 80.2, 79.1, 75.3, 75.0, 74.8, 74.6, 71.1, 70.8, 69.0, 63.9, 62.5, 52.9, 26.0, 25.6, 21.1, 18.1, 18.0, −3.5, −4.1, −4.9, −5.3; FAB MS ($C_{45}H_{67}N_3O_{14}Si_2$) m/z (M)$^+$ calcd 929.4162, obsd 929.4122.

tert-Butyldimethylsilyl (6-O-acetyl-2-azido-3-O-benzyl-4-O-tert-butyldimethylsilyl-2-deoxy-α-D-glucopyranosyl)-(1→4)-methyl 3-O-benzyl-2-O-monochloroacetyl-β-D-glucopyranosiduronate 50

Pyridine (0.5 mL, 6 mmol), monochloroacetic anhydride (360 mg, 1.00 mmol) and DMAP (9 mg, 0.05 mmol) were added to a solution of tert-butyldimethylsilyl (6-O-acetyl-2-azido-3-O-benzyl-4-O-tert-butyldimethylsilyl-2-deoxy-α-D-glucopyranosyl)-(1→4)-methyl-3-O-benzyl-β-D-glucopyranosiduronate (for the synthesis see the procedure to prepare compound 48) (439 mg, 0.52 mmol) in $CH_2Cl_2$ (5 mL). The solution was stirred at room temperature for 3 h, water was added and the mixture was stirred for one additional hour. The organic phase was washed with sat. NaHCO$_3$, water and aqueous HCl (10%), dried over MgSO$_4$ and filtered. The solvent was removed under reduced pressure and the residue was purified by silica gel column chromatography (hexanes:EtOAc 90:20) to yield 50 (470 mg, 0.51 mmol, 98%) as a colorless syrup. $[\alpha]^{24}_D$: +30.1 (c 1.00, CHCl$_3$); IR (thin film on NaCl) 2932, 2107, 1745, 1254, 1029, 839 cm$^{-1}$; $^1$H-NMR (500 MHz, CDCl$_3$) δ 7.37–7.28 (m, 10H, H arom.), 5.50 (d, J=3.4 Hz, 1H, H-1A), 5.05 (dd, J=7.9, 9.1 Hz, 1H, H-2B), 4.74 (d, J=7.3 Hz, 1H, H-1B), 4.86 (d, J=11.0 Hz, 2H, benzyl-CH$_2$), 4.79 (d, J=11.3 Hz, 1H, benzyl-CH$_2$), 4.68 (d, J=11.3 Hz, 1H, benzyl-CH$_2$), 4.35 (dd, J=1.5, 11.9 Hz, 1H, H-6aA), 4.29–4.23 (m, 1H, H-4B), 4.04 (dd, J=3.7, 12.2 Hz, 1H, H-6bA), 3.99 (d, J=9.5 Hz, H-5B), 3.89–3.83 (m, 2H, H-3B, CH$_2$Cl), 3. 79 (s, 3H, OCH$_3$), 3.78 (d, J=14.9 Hz, 1H, CH$_2$Cl), 3.60–3.67 (m, 2H, H-3A, H-5A), 3.53–3.51 (m, 1H, H4A), 3.28 (dd, J=3.0, 9.2 Hz, 1H, H-2A), 2.10 (s, 3H, COCH$_3$), 0.86 (s, 9H, C(CH$_3$)$_3$), 0.85 (s, 9H, C(CH$_3$)$_3$), 0.10 (s, 3H, SiCH$_3$), 0.82 (s, 3H, SiCH$_3$), −0.01 (s, 6H, SiCH$_3$); $^{13}$C-NMR (125 MHz, CDCl$_3$) δ 171.0, 168.4, 165.8, 138.0, 137.8, 128.7, 128.5, 128.0, 127.8, 127.7, 127.5, 97.8, 96.0, 82.6, 80.2, 76.4, 75.3, 75.2, 74.7, 74.6, 71.3, 70.8, 63.9, 62.5, 52.9, 26.1, 25.6, 21.1, 18.2, 17.9, −3.5, −4.1, −4.9, −5.1; FAB MS ($C_{43}H_{64}ClN_3O_{13}Si$) m/z (M)$^+$ calcd 921.3666, obsd 921.366.

tert-Butyldimethylsilyl (6-O-acetyl-2-azido-3,4-di-O-benzyl-2-deoxy-α-D-glucopyranosyl)-(1→4)-methyl-3-O-benzyl-2-O-levulinyl-β-D-glucopyranosiduronate 51

Compound 37 (813 mg, 1.15 mmol) and imidazole (310 mg, 4.55 mmol) were dissolved in $CH_2Cl_2$ (10 mL) and cooled to −15° C. To this mixture tert-butyldimethylsilylchloride (241 mg, 1.60 mmol) was added and stirring was continued at −15° C. After 5 h, tert-butyldimethylsilylchloride (50 mg, 0.33 mmol) was added and after 16 h another portion of tert-butyldimethylsilylchloride (100 mg, 0.66 mmol). After 40 h, water was added and the mixture was warmed to room temperature. After dilution with EtOAc the mixture was washed with sat. NaHCO$_3$ and brine. The organic layer was dried over Na$_2$SO$_4$ and after filtration the solvent was removed under reduced pressure. Flash chromatography on silica gel (hexanes:EtOAc 9:1→8:2) afforded tert-butyldimethylsilyl (6-O-acetyl-2-azido-3,4-di-O-benzyl-2-deoxy-α-D-glucopyranosyl)-(1→4)-methyl 3-O-benzyl-β-D-glucopyranosiduronate (752 mg, 0.92 mmol, 80%) as a colorless foam. $[\alpha]^{24}_D$: +26.2 (c 1.02, $CH_2Cl_2$); IR (thin film on NaCl) 3376, 3049, 2919, 2861, 2107, 1744, 1454, 1362, 1252 cm$^{-1}$; $^1$H-NMR (500 MHz, CDCl$_3$) δ 7.42–7.26 (m, 15H, arom. H), 5.60 (d, J=4.0 Hz, 1H, H-1A), 5.08 (d, J=11.0 Hz, 1H, benzyl-CH$_2$), 4.92–4.89 (m, 2H, benzyl-CH$_2$), 4.86 (d, J=10.7 Hz, 1H, benzyl-CH$_2$), 4.84 (d, J=11.0 Hz, 1H, benzyl-CH$_2$), 4.58 (d, J=7.3 Hz, 1H, H-1B), 4.57 (d, J=10.7 Hz, 1H, benzyl-CH$_2$), 4.27–4.25 (m, 2H, H-6Aa, H-6Ab), 4.14 (dd, J=8.9, 9.5 Hz, 1H, H-4B), 3.96 (d, J=9.8 Hz, 1H, H-5B), 3.91 (dd, J=8.9, 10.4 Hz, 1H, H-3A), 3.77 (s, 3H, OCH$_3$), 3.73 (dd, J=9.2, 8.9 Hz, 1H, H-3B), 3.65–3.61 (m, 1H, H-5A), 3.59–3.52 (m, 2H, H-2B, H-4A), 3.30 (dd, J=4.0, 10.4 Hz, 1H, H-2A), 2.33 (d, J=2.4 Hz, 1H, OH), 2.04 (s, 3H, acetyl-CH$_3$), 0.93 (s, 9H, tert-butyl), 0.16 (s, 3H, CH$_3$), 0.15 (s, 3H, CH$_3$); $^{13}$C-NMR (125 MHz, CDCl$_3$) δ 170.9, 168.6, 138.6, 137.8, 137.7, 128.7, 128.6, 128.3, 128.2, 128.2, 128.1, 127.9, 127.8, 98.0, 97.8, 83.9, 80.2, 77.6, 76.5, 75.6, 75.3, 75.1, 74.9, 74.7, 69.7, 63.5, 62.4, 52.8, 25.8, 21.0, 18.2, −4.1, −5.0; FAB MS ($C_{42}H_{55}N_3O_{12}Si$) m/z (M)$^+$ calcd 821.3555, obsd 821.3549.

tert-Butyldimethylsilyl (6-O-acetyl-2-azido-3,4-di-O-benzyl-2-deoxy-α-D-glucopyranosyl)-(1→4)-methyl 3-O-benzyl-β-D-glucopyranosiduronate (748 mg, 0.41 mmol) and DMAP (334 mg, 2.73 mmol) were dissolved in $CH_2Cl_2$ (5 mL) and a solution of levulinic anhydride (390 mg, 1.82 mmol) in $CH_2Cl_2$ (5 ml) was added. The reaction mixture was stirred for 2 h at room temperature and concentrated. Flash chromatography on silica gel (hexanes:EtOAc 8:2) afforded 51 (834 mg, 0.91 mmol, quant.) as a colorless foam. $[\alpha]^{24}_D$: +18.9 (c 1.01, $CH_2Cl_2$); IR (thin film on NaCl) 3036, 2929, 2857, 2108, 1747, 1720, 1454, 1362 cm$^{-1}$; $^1$H-NMR (500 MHz, CDCl$_3$) δ 7.40–7.26 (m, 15H, arom.), 5.50 (d, J=3.7 Hz, 1H, H-1A), 5.03 (dd, J=7.3, 8.8 Hz, 1H, H-2B), 4.89 (s, 2H, benzyl-CH$_2$), 4.83 (d, J=10.7 Hz, 2H, benzyl-CH$_2$), 4.74 (d, J=11.3 Hz, 1H, benzyl-CH$_2$), 4.73 (d, J=7.3 Hz, 1H, H-1B), 4.56 (d, J=11.0 Hz, 1H, benzyl-CH$_2$), 4.27–4.23 (m, 3H, H-4B, H-6Aa, H-6Ab), 3.97 (d, J=9.5 Hz, 1H, H-5B), 3.89 (dd, J=8.8, 10.1 Hz, 1H, H-3A), 3.82 (dd, J=8.9, 8.5 Hz, 1H, H-3B), 3.77 (s, 3H, OCH$_3$), 3.66–3.62 (m, 1H, H-5A), 3.53 (dd, J=10.1, 8.8 Hz, 1H, H-4A), 3.31 (dd, J=3.7, 10.4 Hz, 1H, H-2A), 2.69–2.65 (m, 2H, Lev-CH$_2$), 2.54–2.49 (m, 2H, Lev-CH$_2$), 2.14 (s, 3H, Lev-CH$_3$), 2.04 (s, 3H, acetyl-CH$_3$), 0.86 (s, 9H, tert-butyl), 0.11 (s, 3H, CH$_3$), 0.10 (s, 3H, CH$_3$); $^{13}$C-NMR (125 MHz, CDCl$_3$) δ 206.2, 171.3, 170.8, 168.5, 138.0, 137.7, 137.7, 128.7, 128.5, 128.2, 128.2, 128.2, 128.1, 127.8, 127.7, 97.7, 96.1, 82.6, 80.2, 77.6, 75.7, 75.2, 75.2, 75.2, 74.5, 74.4, 69.8, 63.5, 62.4, 52.9, 37.9, 30.0, 28.1, 25.6, 21.0, 18.0, −4.2, −5.2; FAB MS (C$_{47}$H$_{61}$N$_3$O$_{14}$Si) m/z (M)$^+$ calcd 919.3923, obsd 919.3914.

tert-Butyldimethylsilyl (6-O-acetyl-2-azido-3,4-di-O-benzyl-2-deoxy-α-D-glucopyranosyl)-(1→4)-methyl 2-O-allyloxycarbonyl-3-O-benzyl-β-D-glucopyranosiduronate 52 tert-Butyldimethylsilyl (6-O-acetyl-2-azido-3,4-di-O-benzyl-2-deoxy-α-D-glucopyranosyl)-(1→4)-methyl-3-O-benzyl-β-D-glucopyranosiduronate (for the synthesis see the procedure to prepare compound 51), (190 mg, 0.231 mmol) and DMAP (780 mg, 6.38 mmol) were dissolved in CH$_2$Cl$_2$ (5 mL) and cooled to −70° C. Allyloxycarbonylchloride (600 μL, 5.65 mmol) was added in three equal portions every 2 h. After the addition was complete the mixture was warmed to room temperature and stirred overnight. The mixture was poured into EtOAc and washed with 1 N HCl, brine and sat. NaHCO$_3$. The organic layer was dried over Na$_2$SO$_4$, filtered and the solvent was removed under reduced pressure. Flash chromatography on silica gel (hexanes:EtOAc 9:1→85:15) afforded 52 (190 mg, 0.21 mmol, 91%) as a colorless oil. [α]$^{24}$$_D$: +21.9 (c 1.25, CH$_2$Cl$_2$); IR (thin film on NaCl) 3026, 2929, 2858, 2108, 1756, 1252 cm$^{-1}$; $^1$H-NMR (500 MHz, CDCl$_3$) δ 7.41–7.26 (m, 15H, arom.), 5.92–5.84 (m, 1H, alloc), 5.52 (d, J=3.7 Hz, 1H, H-1A), 5.36–5.32 (m, 1H, alloc), 5.26–5.23 (m, 1H, alloc), 4.92–4.81 (m, 5H, 4×benzyl-CH$_2$, H-2B), 4.79–4.73 (m, 2H, 2×benzyl-CH$_2$), 4.63–4.54 (m, 3H, H-1B, alloc-CH$_2$), 4.29–4.26 (m, 2H, H-6Aa, H-6Ab), 4.22 (dd, J=9.5, 8.9 Hz, 1H, H-4B), 3.97 (d, J=9.5 Hz, 1H, H-5B), 3.90 (dd, J=8.8, 10.4 Hz, 1H, H-3A), 3.84 (dd, J=9.2, 8.8 Hz, 1H, H-3B), 3.78 (s, 3H, OCH$_3$), 3.65–3.61 (m, 1H, H-5A), 3.54 (dd, J=8.9, 10.1 Hz, 1H, H-4A), 3.32 (dd, J=3.7, 10.4 Hz, 1H, H-2A), 2.05 (s, 3H, acetyl-CH$_3$), 0.88 (s, 9H, tert-butyl), 0.13 (s, 3H, CH$_3$), 0.12 (s, 3H, CH$_3$); $^{13}$C-NMR (125 MHz, CDCl$_3$) δ 170.8, 168.3, 154.0, 137.9, 137.7, 137.6, 131.4, 128.7, 128.7, 128.5, 128.3, 128.2, 128.2, 128.1, 127.9, 127.7, 119.6, 97.8, 96.1, 82.5, 80.2, 79.1, 77.6, 75.7, 75.4, 75.2, 74.9, 74.5, 69.8, 69.0, 63.5, 62.4, 52.9, 25.6, 21.0, 18.0, −4.1, −5.4; FAB MS (C$_{46}$H$_{59}$N$_3$O$_{14}$Si) m/z (M)$^+$ calcd 905.3766, obsd 905.3751.

O-(6-O-Acetyl-2-azido-3-O-benzyl-4-O-tert-butyldimethylsilyl-2-deoxy-α-D-glucopyranosyl)-(1→4)-methyl 2-O-levulinyl-3-O-benzyl-α-D-glucopyranosiduronate trichloroacetimidate 53

Compound 48 (1.06 g, 1.12 mmol) was dissolved in THF (10 mL) and cooled to 0° C. Glacial acetic acid (90 μL, 1.57 mmol) and TBAF (1M in THF, 1.30 mL, 1.30 mmol) were added in sequence. After 30 min the mixture was poured into Et$_2$O (100 mL) and washed with brine (3×). The organic layer was dried over Na$_2$SO$_4$, filtered and the solvent was removed under reduced pressure. The residue was dissolved in CH$_2$Cl$_2$ (20 mL) and cooled to 0° C. Trichloroacetonitrile (1.7 mL, 17.0 mmol) and DBU (15 μL, 0.1 mmol) were added and the mixture was stirred at 0° C. for 1 h and at room temperature for 3 h. After removal of the solvent under reduced pressure, flash chromatography on silica gel (hexanes:EtOAc 85:15→70:30) afforded 53 (1.0 g, 1.03 mmol, 92%) as a colorless foam. [α]$^{24}$$_D$: +108.9 (c 1.69, CH$_2$Cl$_2$); IR (thin film on NaCl) 3337, 3031, 2954, 2929, 2857, 2105, 1746, 1720, 1678, 1454 cm$^{-1}$; $^1$H-NMR (500 MHz, CDCl$_3$) δ 8.71 (s, 1H, NH), 7.26–7.40 (m, 10H, arom.), 6.54 (d, J=3.7 Hz, 1H, H-1B), 5.63 (d, J=3.7 Hz, 1H, H-1A), 5.12–5.16 (m, 1H, H-2B), 4.80–4.92 (m, 4H, 4×benzyl-CH$_2$), 4.48 (d, J=9.5 Hz, 1H, H-5B), 4.35 (dd, J=2.1, 11.9 Hz, 1H, H-6Aa), 4.21–4.29 (m, 2H), 4.04 (dd, J=4.0, 12.2 Hz, 1H, H-6Ab), 3.79 (s, 3H, OCH$_3$), 3.69 (dd, J=8.5, 10.1 Hz, 1H), 3.64 (dd, J=9.5, 8.5 Hz, 1H), 3.45–3.49 (m, 1H, H-5A), 3.23 (dd, J=4.0, 10.1 Hz, 1H, H-2A), 2.61–2.71 (m, 2H, Lev-CH$_2$), 2.35–2.50 (m, 2H, Lev-CH$_2$), 2.14 (s, 3H, CH$_3$), 2.10 (s, 3H, CH$_3$), 0.88 (s, 9H, tert-butyl), 0.00 (s, 3H, CH$_3$), −0.01 (s, 3H, CH$_3$); $^{13}$C-NMR (125 MHz, CDCl$_3$) δ 206.1, 172.0, 171.0, 168.7, 160.7, 138.1, 137.9, 128.7, 128.5, 128.0, 127.7, 127.6, 127.4, 98.1, 93.3, 90.9, 80.1, 79.7, 75.3, 75.3, 74.1, 72.5, 72.4, 71.2, 70.9, 63.7, 62.6, 53.1, 37.8, 30.0, 27.7, 26.0, 21.1, 18.1, −3.5, −4.9; FAB MS (C$_{42}$H$_{55}$Cl$_3$N$_4$O$_{14}$Si) m/z (M)$^+$ calcd 972.2550, obsd 972.2579.

O-(6-O-Acetyl-2-azido-3-O-benzyl-4-O-tert-butyldimethylsilyl-2-deoxy-α-D-glucopyranosyl)-(1→4)-methyl 2-O-allyloxycarbonyl-3-O-benzyl-α-D-glucopyranosiduronate trichloroacetimidate 54

Compound 49 (271 mg, 0.291 mmol) was dissolved in anhydrous THF (5 mL) and cooled to 0° C. Glacial acetic acid (21 μL, 0.367 mmol) and TBAF (1M in THF, 320 μL, 0.32 mmol) were added in sequence. After 30 min the mixture was poured into EtO (50 mL) and washed with brine (3×). The organic layer was dried over Na$_2$SO$_4$, filtered and the solvent was removed under reduced pressure. The residue was dissolved in CH$_2$Cl$_2$ (11 mL) and cooled to 0° C. Trichloroacetonitrile (450 μL, 4.49 mmol) and DBU (5 μL, 0.033 mmol) were added and the mixture was stirred overnight at room temperature. After removal of the solvent under reduced pressure, flash chromatography on silica gel (hexanes:EtOAc 85:15) afforded 54 (190 mg, 0.198 mmol, 68%) as a colorless foam. [α]$^{24}$$_D$: +114.0 (c 1.37, CH$_2$Cl$_2$); IR (thin film on NaCl) 3340, 3026, 2953, 2857, 2105, 1754, 1679, 1454, 1367 cm$^{-1}$; $^1$H-NMR (500 MHz, CDCl$_3$) δ 8.74 (s, 1H, NH), 7.40–7.26 (m, 10H, arom.), 6.63 (d, J=3.4 Hz, 1H, H-1B), 5.91–5.82 (m, 1H, alloc), 5.65 (d, J=3.7 Hz, 1H, H-1A), 5.34–5.30 (m, 1H, alloc), 5.27–5.23 (m, 1H, alloc), 5.01 (dd, J=3.4, 9.5 Hz, 1H, H-2B), 4.93–4.85 (m, 3H, 3×benzyl-CH$_2$), 4.82 (d, J=11.0 Hz, 1H, benzyl-CH$_2$) 4.65–4.57 (m, 2H, alloc), 4.50 (d, J=9.5 Hz, 1H, H-5B), 4.37 (dd, J=1.8, 12.2 Hz, 1H, H-6Aa), 4.29–4.22 (m, 2H, H-3B, H-4B), 4.05 (dd, J=4.0, 12.2 Hz, 1H, H-6Ab), 3.80 (s, 3H, OCH$_3$), 3.71 (dd, J=10.1, 8.5 Hz, 1H, H-3A), 3.65 (dd, J=9.2, 8.5 Hz, 1H, H-4A), 3.50–3.46 (m, 1H, H-5A), 3.23 (dd, J=3.7, 10.1 Hz, 1H, H-2A), 2.11 (s, 3H, acetyl-CH$_3$), 0.89 (s, 9H, tert-butyl), 0.00 (s, 3H, CH$_3$), −0.01 (s, 3H, CH$_3$); $^{13}$C-NMR (125 MHz, CDCl$_3$) δ 171.0, 168.6, 160.7, 154.2, 138.0, 137.6, 131.2, 128.6, 128.4, 128.0, 127.8, 127.7, 127.4, 119.4, 98.2, 93.2, 90.8, 80.0, 79.4, 75.8, 75.4, 75.2, 74.1, 72.4, 71.2, 70.9, 69.2, 63.6, 62.5, 53.0, 26.0, 21.0, 18.1, −3.6, −4.9; FAB MS (C$_{41}$H$_{53}$Cl$_3$N$_4$O$_{14}$Si) m/z (M)$^+$ calcd 958.2393, obsd 958.2392.

O-(6-O-Acetyl-2-azido-3,4-di-O-benzyl-2-deoxy-α-D-glucopyranosyl)-(1→4)-methyl-2-O-levulinyl-3-O-benzyl-α-D-glucopyranosiduronate trichloroacetimidate 55

Compound 51 (345 mg, 0.376 mmol) was dissolved in THF (10 mL) and cooled to 0° C. Glacial acetic acid (27 μL, 0.472 mmol) and tetrabutylammoniumfluoride (1M in THF, 415 µL, 0.415 mmol) were added in sequence. After 40 min this mixture was poured into EtOAc (50 mL) and washed with sat. NaHCO$_3$. The organic layer was dried over Na$_2$SO$_4$, filtered and the solvent was removed under reduced pressure. The residue was dissolved in CH$_2$Cl$_2$ (10 mL) and cooled to 0° C. Trichloroacetonitrile (750 µL, 7.48 mmol) and DBU (30 µL) were added and the mixture was stirred for 2 h. After removal of the solvent under reduced pressure, flash chromatography on silica gel (hexanes:EtOAc 8:2→6:4) afforded 55 as a colorless foam (302 mg, 0.32 mmol, 85%). [α]$^{24}_D$: +79.8 (c 1.72, CH$_2$Cl$_2$); IR (thin film on NaCl) 3337, 3063, 3030, 2953, 2108, 1746, 1719, 1677, 1497, 1363 cm$^{-1}$; $^1$H-NMR (500 MHz, CDCl$_3$) δ 8.71 (s, 1H, NH), 7.40–7.25 (m, 15H, arom.), 6.53 (d, J=3.4 Hz, 1H, H-1B) 5.55 (d, J=3.7 Hz, 1H, H-1A), 5.14–5.11 (m, 1H, H-2B), 4.95–4.82 (m, 5H, benzyl-CH$_2$), 4.57 (d, J=11.0 Hz, 1H, benzyl-CH$_2$), 4.46–4.42 (m, 1H, H-4B), 4.28–4.20 (m, 4H, H-3B, H-5B, H-6Aa, H-6Ab), 3.94 (dd, J=8.5, 10.4 Hz, 1H, H-3A), 3.77 (s, 3H, OCH$_3$), 3.62–3.58 (m, 1H, H-5A), 3.51 (dd, J=8.8, 10.1 Hz, 1H, H-4A), 3.30 (dd, J=3.7, 10.4 Hz, 1H, H-2A), 2.70–2.60 (m, 2H, Lev-CH$_2$), 2.51–2.36 (m, 2H, Lev-CH$_2$), 2.14 (s, 3H, Lev-CH$_3$), 2.04 (s, 3H, acetyl-CH$_3$); $^{13}$C-NMR (125 MHz, CDCl$_3$) δ 206.1, 172.0, 170.9, 168.6, 160.7, 138.0, 137.8, 137.7, 128.7, 128.7, 128.7, 128.2, 128.1, 127.9, 127.6, 98.3, 93.2, 90.9, 80.1, 79.4, 77.6, 75.7, 75.4, 75.2, 75.0, 72.5, 72.4, 70.0, 63.3, 62.4, 53.2, 37.8, 30.0, 27.7, 21.0; FAB MS (C$_{43}$H$_{47}$Cl$_3$N$_4$O$_{14}$) m/z (M)$^+$ calcd 948.2154, obsd 948.2118.

O-(6-O-Acetyl-2-azido-3,4-di-O-benzyl-2-deoxy-α-D-glucopyranosyl)-(1→4)-methyl 3-O-benzyl-2-O-allyloxycarbonyl-α/β-D-glucopyranosiduronate trichloroacetimidate 56

Compound 52 (74 mg, 0.082 mmol) was dissolved in THF (2 mL) and cooled to 0° C. Glacial acetic acid (6 µL, 0.1 mmol) and TBAF (1 M in THF, 90 µL, 0.09 mmol) were added. After 30 min the mixture was poured into Et$_2$O (50 mL) and washed with brine (3×). The organic layer was dried over Na$_2$SO$_4$, filtered and the solvent was removed under reduced pressure. The residue was dissolved in CH$_2$Cl$_2$ (2 mL) and cooled to 0° C. Trichloroacetonitrile (120 µL, 1.19 mmol) and DBU (1.2 µL, 0.008 mmol) were added and the mixture was stirred overnight at room temperature. After removal of the solvent under reduced pressure, flash chromatography on silica gel (hexanes:EtOAc 85:15) afforded 56 (63 mg, 0.07 mmol, 83%) as a colorless foam. FAB MS (C$_{42}$H$_{45}$Cl$_3$N$_4$O$_{14}$) m/z (M)$^+$ calcd 934.1998, obsd 934.1989.

3,6-Di-O-acetyl-2-azido-4-O-tert-butyldimethylsilyl-2-deoxy-β-D-glucopyranosyl-(1→4)-methyl 1,2-O-acetyl-3-O-benzyl-α/β-L-idopyranosiduronate 57

Pyridine (2.0 mL, 24 mmol), acetic anhydride (1.4 mL, 15 mmol) and DMAP (12 mg, 0.1 mmol) were added to a solution of 53 (700 mg, 1.02 mmol) in CH$_2$Cl$_2$ (16 mL). The solution was stirred at room temperature for 1 h, water was added and the mixture was stirred for one additional hour. The organic phase was washed with sat. NaHCO$_3$, water, and aqueous HCl (10%), dried over MgSO$_4$ and filtered. The solvent was removed under reduced pressure and the residue was purified by silica gel column chromatography (hexane:EtOAc 90:20) to yield 57 (707 mg, 0.92 mmol, 95%) as a colorless syrup. FAB MS (C$_{34}$H$_{49}$N$_3$O$_{15}$Si) m/z (M$^+$) calcd 767.2933, obsd 767.2951.

6-O-Acetyl-2-azido-3-O-benzyl-4-O-tert-butyldimethylsilyl-2-deoxy-α-D-glucopyranosyl-(1→4)-methyl 1,2-O-acetyl-3-O-benzyl-L-idopyranosiduronate 58

Pyridine (1.5 mL, 18 mmol), acetic anhydride (1 mL, 11 mmol) and DMAP (10 mg, 0.08 mmol) were added to a solution of 42 (560 mg, 0.77 mmol) in CH$_2$Cl$_2$ (10 mL). The solution was stirred at room temperature for 1 h, water was added and the mixture was stirred for one additional hour. The organic phase was washed with sat. NaHCO$_3$, water and aqueous HCl (10%), dried over MgSO$_4$ and filtered. The solvent was removed under reduced pressure and the residue was purified by silica gel column chromatography (hexane:EtOAc 90:20) to yield 58 (619 mg, 0.76 mmol, 99%) as a colorless syrup. FAB MS (C$_{39}$H$_{53}$N$_3$O$_{14}$Si) m/z (M)$^+$ calcd 815.3297, obsd 815.3270.

O-3,6-Di-O-acetyl-2-azido-4-O-tert-butyldimethylsilyl-2-deoxy-α-D-glucopyranosyl-(1→4)-methyl 2-O-acetyl-3-O-benzyl-β-L-idopyranosyluronate trichloroacetimidate 59

Benzylamine (2.0 mL, 18.3 mmol) was added to a solution of 57 (650 mg, 0.85 mmol) in Et$_2$O (50 mL) at 0° C. After stirring at 0° C. for 4 h the mixture was diluted with CH$_2$Cl$_2$, filtered and washed with HCl (10%). The organic phase was dried over Na$_2$SO$_4$, filtered and the solvent was removed under reduced pressure. Flash chromatography on silica gel (hexane:AcOEt 90:10→80:20) afforded 3,6-di-O-acetyl-2-azido-4-O-tert-butyldimethylsilyl-2-deoxy-α-D-glucopyranosyl-(1→4)-methyl 2-O-acetyl-3-O-benzyl-α/β-L-idopyranosiduronate (443 mg, 72%) as a white solid. FAB MS (C$_{32}$H$_{47}$N$_3$O$_{14}$Si) m/z (M)$^+$ calcd 725.2827, obsd 725.2811.

A solution of 3,6-di-O-acetyl-2-azido-4-O-tert-butyldimethylsilyl-2-deoxy-α-D-glucopyranosyl-(1→4)-methyl 2-O-acetyl-3-O-benzyl-α/β-L-idopyranosiduronate (335 mg, 0.46 mmol) and trichloroacetonitrile (1.3 mL, 12.5 mmol) in CH$_2$Cl$_2$ (10 mL) containing freshly activated powdered 4 Å molecular sieves (100 mg) was stirred 30 minutes at room temperature. After cooling the solution to 0° C. DBU (30 µl, 0.2 mmol) was added. The temperature was allowed to rise and after 1 h stirring, the mixture was filtered through a pad of Celite and concentrated. The residue was purified by silica gel column chromatography (hexane:EtOAc 85:15) yielding 59 (373 mg, 0.43 mmol, 93%) as a white solid. [α]$^{24}_D$: +53.4 (c 1.00, CHCl$_3$); IR (thin film on NaCl) 2935, 2693, 2109, 1744, 1675, 1372 cm$^{-1}$; $^1$H-NMR (500 MHz, CDCl$_3$) δ 8.68 (s, 1H, NH), 7.36–7.30 (m, 5H, H-arom.), 6.41 (s, 1H, H-1B), 5.26 (dd, J=8.5, 10.4 Hz, 1H, H-3A), 5.17 (s, 1H, H-2B), 5.00 (d, J=3.4 Hz, 1H, H-3B), 4.98 (d, J=1.8 Hz, 1H, H-1A) 4.81 (d, J=11.6 Hz, 1H, benzyl-CH$_2$) 4.65 (d, J=11.6 Hz, 1H, benzyl-CH$_2$), 4.46 (dd, J=2.1, 12.5 Hz, 1H, H-6aA), 4.27 (s, 1H, H-5B), 4.09–4.06 (m, 2H, H-6bA, H-4B), 4.00–3.81 (m, 1H, H-5A), 3.80 (s, 3H, OCH$_3$), 3.81–3.79 (m, 1H, H-4A), 3.05 (dd, J=3.3, 10.7 Hz, 1H, H-2A), 2.20 (s, 3H, COCH$_3$), 2.14 (s, 3H, COCH$_3$), 2.10 (s, 3H, COCH$_3$), 0.84 (s, 9H, C(CH$_3$)$_3$), 0.49 (s, 3H, SiCH$_3$), 0.30 (s, 3H, SiCH$_3$); $^{13}$C-NMR (125 MHz, CDCl$_3$) δ 170.7, 170.3, 169.9, 169.1, 160.3, 137.2, 128.6, 128.1, 128.0, 98.3, 95.7, 73.7, 72.8, 72.7, 72.3, 71.1, 69.2, 68.9, 65.4, 62.4, 61.9, 52.8, 25.8, 21.5, 21.0, 20.9, 18.1, −4.0, −4.8; FAB MS (C$_{34}$H$_{47}$Cl$_3$N$_4$O$_{14}$Si) m/z (M)$^+$ calcd 868.1924, obsd 868.1938.

O-(6-O-Acetyl-2-azido-3-O-benzyl-4-O-tert-butyldimethylsilyl-2-deoxy-α-D-glucopyranosyl-(1→4)-methyl 2-O-acetyl-3-O-benzyl-β-L-idopyranosyluronate) trichloroacetimidate 60

Benzylamine (0.6 mL, 5.5 mmol) was added to a solution of 58 (600 mg, 0.73 mmol) in Et$_2$O (15 mL) at 0° C. After stirring at 0° C. for 5 h the mixture was diluted with CH$_2$Cl$_2$, filtered and washed with HCl (10%). The organic phase was dried over Na$_2$SO$_4$ and after filtration purified by silica gel column chromatography (hexane:AcOEt 90:10→80:20) to yield 6-O-acetyl-2-azido-3-O-benzyl-4-O-tert-butyldimethylsilyl-2-deoxy-α-D-glucopyranosyl-(1→4)- methyl 2-O-acetyl-3-O-benzyl-α/β-L-idopyranosiduronate (415 mg, 0.54 mmol, 77%) as a white solid. FAB MS ($C_{37}H_{51}N_3O_{13}Si$) m/z (M)+ calcd 773.3191, obsd 773.3201.

A solution of 6-O-acetyl-2-azido-3-O-benzyl-4-O-tert-butyldimethylsilyl-2-deoxy-α-D-glucopyranosyl-(1→4)-methyl 2-O-acetyl-3-O-benzyl-α/β-L-idopyranosiduronate (90 mg, 0.12 mmol) and trichloroacetonitrile (0.34 mL, 3.3 mmol) in $CH_2Cl_2$ (3 mL) containing freshly activated powdered 4 Å molecular sieves (50 mg) was stirred 30 minutes at room temperature. After cooling the solution to 0° C. DBU (2 μl, 0.012 mmol) was added. The temperature was allowed to rise and after 1 h stirring, the mixture was filtered through a pad of Celite and concentrated. The residue was purified by silica gel column chromatography (hexane:EtOAc 85:15) yielding 60 (104 mg, 0.113 mmol, 97%) as a white solid. $[α]^{24}{}_D$: +70.3 (c 1.00, $CHCl_3$); $^1$H-NMR (500 MHz, $CDCl_3$) δ 8.70 (s, 1H, NH), 7.36–7.27 (m, 10H, arom.), 6.43 (s, 1H, H-1B), 5.16 (s, 1H, H-2B), 4.93 (d, J=3.4 Hz, 1H, H-3B), 5.00 (d, J=2.1 Hz, 1H, H-1A), 4.84 (d, J=11.0 Hz, 1H, benzyl-$CH_2$), 4.83 (d, J=11.6 Hz, 1H, benzyl-$CH_2$), 4.76 (d, J=11.0 Hz, 1H, benzyl-$CH_2$), 4.67 (d, J=11.6 Hz, 1H, benzyl-$CH_2$), 4.41 (dd, J=2.1, 12.2 Hz, H-6aA), 4.21 (s, 1H, H-5B), 3.82 (s, 3H, $OCH_3$), 4.07–4.02 (m, 2H, H-6bA, H-4B), 3.75–3.70 (m, 1H, H-5A), 3.68–3.62 (m, 3H, H-4A, H-3A), 3.35 (dd, J=3.5, 9.7 Hz, 1H, H-2A), 2.17 (s, 3H, $COCH_3$), 2.07 (s, 3H, $COCH_3$), 0.88 (s, 9H, $C(CH_3)_3$), 0.05 (s, 3H, $SiCH_3$), −0.01 (s, 3H, $SiCH_3$); $^{13}$C-NMR (125 MHz, $CDCl_3$) δ 170.9, 170.1, 168.9, 160.3, 137.9, 137.2, 128.6, 128.5, 128.2, 127.9, 127.8, 127.4, 97.1, 95.4, 80.3, 75.2, 72.6, 72.1, 71.3, 70.8, 70.8, 69.3, 65.4, 64.0, 62.7, 52.7, 26.3, 21.1, 21.0, 18.1, −3.5, −4.8; FAB MS ($C_{34}H_{47}Cl_3N_4O_{14}Si$) m/z (M)+ calcd 916.2287, obsd 916.2246.

n-Pentenyl (6-O-acetyl-2-azido-3-O-benzyl-4-O-tert-butyldimethylsilyl-2-deoxy-α-D-glucopyranosyl)-(1→4)-methyl 3-O-benzyl-2-O-levulinyl-β-D-glucopyranosiduronate 61

Compound 53 (292 mg, 0.30 mmol) was coevaporated with toluene (3x), dried under vacuum for 1 h, dissolved in toluene (5 mL) and 4-penten-1-ol (300 μL, 3.00 mmol) was added. After cooling the mixture to 0° C., TMSOTf (0.1 M in toluene, 300 μL, 0.03 mmol) was added dropwise. The mixture was warmed to room temperature and stirred for 2 h. Triethylamine (0.6 mL) was added and the solvent was removed under reduced pressure. Flash chromatography on silica gel (hexanes:EtOAc 85:15) afforded 61 (203 mg, 0.60 mmol, 75%) as a colorless gum. $[α]^{24}{}_D$: +53.1 (c 1.18, $CH_2Cl_2$); IR (thin film on NaCl) 2930, 2858, 2106, 1747, 1362, 1237 cm$^{-1}$; $^1$H-NMR (500 MHz, $CDCl_3$) δ 7.25–7.39 (m, 10H, arom.), 5.75–5.84 (m, 1H, CH olef.), 5.54 (d, J=3.7 Hz, 1H, H-1A), 5.07 (dd, J=7.3, 8.5 Hz, 1H, H-2B), 4.95–5.04 (m, 2H, olef.), 4.88 (d, J=11.0 Hz, 1H, benzyl-$CH_2$), 4.74–4.82 (m, 3H of Ph$CH_2$), 4.48 (d, J=7.3 Hz, 1H, H-1B), 4.35 (dd, J=2.1, 11.9 Hz, 1H, H-6$_a$A), 4.25 (t, J=9.2 Hz, 1H, H-4B), 4.02–4.07 (m, 2H, H-6$_b$A, H-5B), 3.84–3.89 (m, 2H, H-3B, pent), 3.79 (s, 3H, $COOCH_3$), 3.61–3.67 (m, 2H, H-3A, H-4A), 3.43–3.51 (m, 2H, H-5A, pent), 3.23–3.26 (m, 1H, H-2A), 2.67–2.71 (m, 2H, lev-$CH_2$), 2.44–2.58 (m, 2H, lev-$CH_2$), 2.14 (s, 3H, lev-$CH_3$), 2.03–2.12 (m, 5H, acetyl-$CH_3$, pent-$CH_2$), 1.60–1.72 (m, 2H, pent-$CH_2$), 0.88 (s, 9H, tert-butyl), 0.00 (s, 3H, $CH_3$), −0.01 (s, 3H, $CH_3$); $^{13}$C-NMR (125 MHz, $CDCl_3$) δ 206.7, 172.0, 171.5, 169.3, 138.7, 138.6, 138.3, 129.1, 129.0, 128.4, 128.3, 128.3, 127.9, 115.7, 101.7, 98.1, 83.1, 80.7, 75.8, 75.0, 75.0, 74.9, 74.1, 71.7, 71.4, 70.0, 64.4, 63.1, 53.4, 38.5, 30.6, 30.5, 29.2, 28.6, 26.6, 21.6, 18.7, −3.0, −4.4; FAB MS ($C_{45}H_{63}N_3O_{14}Si$) m/z (M)+ calcd 897.4079, obsd 897.4067.

n-Pentenyl (6-O-acetyl-2-azido-3-O-benzyl-2-deoxy-α-D-glucopyranosyl)-(1→4)-methyl 3-O-benzyl-2-O-levulinyl-β-D-glucopyranosiduronate 62

Compound 61 (674 mg, 0.75 mmol) was dissolved in THF (80 mL). Glacial acetic acid (20 mL) and HF/pyridine-complex (12 mL) were added and the solution was stirred at room temperature for 93 h. The mixture was poured into EtOAc and washed with brine, water, sat. $NaHCO_3$ and dried over $Na_2SO_4$. After filtration, the solvent was removed under reduced pressure. Flash chromatography on silica gel (hexanes:EtOAc 8:2→6:4) afforded 62 (500 mg, 0.64 mmol, 85%) as a colorless oil. $[α]^{24}{}_D$: +0.3 (c 1.20, $CH_2Cl_2$); IR (thin film on NaCl) 3484, 3037, 2924, 2109, 1746, 1719, 1363 cm$^{-1}$; $^1$H-NMR (500 MHz, $CDCl_3$) δ 7.43–7.25 (m, 10H, arom.), 5.84–5.75 (m, 1H, CH olef.), 5.50 (d, J=3.7 Hz, 1H, H-1A), 5.07 (dd, J=7.3, 8.5 Hz, 1H, H-2B), 5.04–4.95 (m, 2H, $CH_2$ olef.), 4.90 (d, J=11.3 Hz, 1H of Ph$CH_2$), 4.88 (d, J=11.3 Hz, 1H of Ph$CH_2$), 4.81 (d, J=10.7 Hz, 1H, Ph$CH_2$), 4.75 (d, J=10.7 Hz, 1H of Ph$CH_2$), 4.57 (dd, J=3.1, 12.5 Hz, 1H, H-6$_a$A), 4.48 (d, J=7.3 Hz, 1H, H-1B), 4.24 (dd, J=9.2 Hz, J=8.9 Hz, 1H, H-4B), 4.12 (dd, J=1.8, 12.5 Hz, 1H, H-6$_b$A), 4.01 (d, J=9.5 Hz, 1H, H-5B), 3.88–3.83 (m, 2H, H-3B, pent), 3.78 (s, 3H, $COOCH_3$), 3.74 (dd, J=8.8, 10.0 Hz, 1H, H-3A), 3.50–3.38 (m, 3H, H-4A, H-5A, pent), 3.23 (dd, J=3.7, 10.4 Hz, 1H, H-2A), 3.05 (d, J=3.4 Hz, 1H, OH), 2.71–2.68 (m, 2H, lev-$CH_2$), 2.59–2.45 (m, 2H, lev-$CH_2$), 2.15 (s, 3H, lev-$CH_3$), 2.11–2.04 (m, 5H, $CH_3$, pent), 1.72–1.60 (m, 2H, pent); $^{13}$C-NMR (125 MHz, $CDCl_3$) 206.2, 172.5, 171.5, 168.9, 138.1, 138.0, 137.8, 128.8, 128.6, 128.4, 128.3, 127.9, 127.8, 115.2, 101.2, 97.8, 82.5, 79.1, 75.5, 74.6, 74.5, 74.5, 73.7, 70.9, 70.5, 69.5, 62.9, 62.6, 52.9, 38.0, 30.1, 30.0, 28.7, 28.1, 21.0; FAB MS ($C_{39}H_{49}N_3O_{14}$) m/z (M)+ calcd 783.3215, obsd 783.3206.

n-Pentenyl (6-O-acetyl-2-azido-3-O-benzyl-4-O-tert-butyldimethylsilyl-2-deoxy-α-D-glucopyranosyl)-(1→4)-methyl 3-O-benzyl-2-O-monochloroacetyl-β-O-D-glucopyranosiduronate 63

Compound 46 (816 mg, 0.856 mmol) was coevaporated with toluene (3x), dried under vacuum for 1 h, dissolved in toluene (30 mL) and 4-penten-1-ol (450 μL, 4.36 mmol) was added. After cooling the mixture to 0° C., TMSOTf (0.1 M in toluene, 1.72 mL, 0.17 mmol) was added dropwise. The mixture was warmed to room temperature and stirred for 48 h. Triethylamine (1.7 mL) was added and the solvent was removed under reduced pressure. Flash chromatography on silica gel (hexanes:EtOAc 85:15) afforded 63 (527 mg, 0.60 mmol, 70%) as a colorless gum. $[α]^{24}{}_D$: +45.5 (c 1.00, $CHCl_3$); IR (thin film on NaCl) 2954, 2109, 1745, 1223, 1072, 838 cm$^{-1}$; $^1$H-NMR (500 MHz, $CDCl_3$) δ 7.37–7.28 (m, 10H, H-arom.), 5.79–5.74 (m, 1H, CH olef.), 5.50 (d, J=3.7 Hz, 1H, H-1A), 5.09 (dd, J=7.6, 8.8 Hz, H-2B), 5.07–4.95 (m, 2H, $CH_2$ olef.), 4.74 (d, J=7.3 Hz, H-1B), 4.87 (d, J=11.3 Hz, 2H, Ph$CH_2$), 4.86 (d, J=11.0 Hz, 2H, Ph$CH_2$), 4.80 (d, J=11.3 Hz, 1H, Ph$CH_2$) 4.70 (d, J=11.0 Hz, 1H, Ph$CH_2$), 4.48 (d, 1H, H-1B), 4.35 (dd, J=2.1, 11.9 Hz, 1H, H-6$_a$A), 4.04 (t, 1H, H-4B), 4.05–4.00 (m, 2H, H-5B, H-6$_b$A), 3.89–3.80 (m, 4H, H-3B, $CH_2Cl$, 1H of $OCH_2$), 3.79 (s, 3H, $OCH_3$), 3.65–3.64 (m, 2H, H-3A, H-4A) 3.50–3.42 (m, 2H, H-5A, 1H of $OCH_2$), 3.28 (dd, J=4.0, 10.1 Hz, 1H, H-2A), 2.09 (s, 3H, $COCH_3$), 1.07–1.03 (m, 2H pent-$CH_2$), 1.69–1.58 (m, 2H pent-$CH_2$), 0.88 (s, 9H, tert-butyl), −0.01 (s, 6H, 2 $CH_3$); $^{13}$C-NMR (125 MHz, $CDCl_3$) δ 171.0, 168.6, 166.0, 137.9, 137.7, 137.4, 129.0, 128.7, 128.5, 128.1, 128.0, 127.9, 127.75, 127.7, 127.4, 115.0, 100.9, 97.7, 82.5, 80.2, 75.3, 74.9, 74.8, 74.6, 74.5, 71.3, 70.8, 69.5, 63.8, 62.5, 52.9, 44.0, 42.8, 40.6, 30.0, 28.6, 26.0, 21.0, 18.1, −3.5, −4.9; FAB MS ($C_{42}H_{36}ClN_3O_{13}Si$) m/z (M)+ calcd 875.3427, obsd 875.3432.

n-Pentenyl (6-O-acetyl-2-azido-3-O-benzyl-2-deoxy-α-D-glucopyranosyl)-(1→4)-methyl 3-O-benzyl-2-O-rnonochloroacetyl-β-O-pentenyl-D-glucopyranosiduronate 64

Compound 63 (250 mg, 0.285 mmol) was dissolved in THF (33 mL). Glacial acetic acid (8 mL) and HF/pyridine-complex (4.8 mL) were added and the solution was stirred at room temperature for 4 days. The mixture was poured into Et$_2$O and washed with brine, sat. NaHCO$_3$ and dried over Na$_2$SO$_4$. After filtration, the solvent was removed under reduced pressure. Flash chromatography on silica gel (hexanes:EtOAc 7:3) afforded 64 (186 mg, 0.244 mmol, 85%) as a colorless foam. [α]$^{24}_D$: +10.8 (c 1.00, CHCl$_3$); IR (thin film on NaCl) 3485, 2925, 2109, 1747, 1454, 1028 cm$^{-1}$; $^1$H-NMR (500 MHz, CDCl$_3$) δ 7.43–7.27 (m, 10H, arom.), 5.98–5.70 (m, 1H, CH olef.), 5.47 (d, J=3.8 Hz, H-1A), 5.09 (t, 1H, H-2B), 5.08–4.97 (m, 2H, CH$_2$ olef.), 4.95–4.93 (m, 3H, PhCH$_2$), 4.69 (d, J=10.7 Hz, 1H of Ph CH$_2$), 4.40–4.35 (m, 1H, H-2B), 4.59 (dd, J=2.7, 12.4 Hz, 1H, H-6$_a$A), 4.48 (d, J=7.7 Hz, 1H, H-1B), 4.24 (t, 1H, H-4B), 4.11 (dd, J=1.9, 12.4 Hz, 1H, H-6$_b$A), 4.0 (d, 1H, J=5.5 Hz, H-5B), 3.89–3.79 (m, 4H, H-3B, CH$_2$Cl, 1H of OCH$_2$), 3.79 (s, 3H, COOCH$_3$), 3.78–3.70 (m, 1H, H-3A), 3.50–3.38 (m, 3H, H-4A, H-5A, 1H of OCH$_2$), 3.27 (dd, J=3.8, 10.4 Hz, 1H, H-2A), 2.98 (bs, 1H, OH), 2.03–2.01 (m, 2H, pent-CH$_2$), 2.12 (s, 3H, CH$_3$), 1.73–1.59 (m, 2H, pent-CH$_2$); $^{13}$C-NMR (125 MHz, CDCl$_3$) δ 172.5, 168.6, 165.9, 138.0, 137.9, 137.7, 128.8, 128.7, 128.4, 128.3, 128.1, 127.7, 115.3, 101.0, 98.0, 82.5, 79.0, 75.5, 75.1, 75.0, 74.8, 74.6, 71.1, 70.5, 69.6, 62.9, 62.6, 53.0, 40.6, 30.0, 28.6, 21.0; FAB MS (C$_{36}$H$_{44}$ClN$_3$O$_3$) m/z (M)$^+$ calcd 761.2563, obsd 761.2557.

n-Pentenyl (6-O-acetyl-2-azido-3-O-benzyl-4-O-tert-butyldimethylsilyl-2-deoxy-α-D-glucopyranosyl)-(1→4)-methyl 2-O-allyloxycarbonyl-3-O-benzyl-β-D-glucopyranosiduronate 65

Compound 54 (93 mg, 0.097 mmol) was coevaporated with toluene (3×), dried under vacuum for 1 h, dissolved in toluene (5 mL) and 4-penten-1-ol (50 μL, 0.484 mmol) was added. After cooling the mixture to 0° C., TMSOTf (0.1 M in toluene, 200 μL, 0.019 mmol) was added dropwise. The mixture was warmed to room temperature and stirred for 30 min. Triethylamine (200 μL) was added and the solvent was removed under reduced pressure. Flash chromatography on silica gel (hexanes:EtOAc 85:15) afforded 65 (57 mg, 0.064 mmol, 66%) as a colorless gum. [α]$^{24}_D$: +64.1 (c 1.65, CH$_2$Cl$_2$); IR (thin film on NaCl) 3065, 2953, 2857, 2106, 1755, 1454, 1369 cm$^{-1}$; $^1$H-NMR (500 MHz, CDCl$_3$) δ 7.26–7.39 (m, 10H, arom.), 5.73–5.92 (m, 2H, alloc, pent), 5.55 (d, J=3.7 Hz, 1H, H-1A), 5.32–5.37 (m, 1H, alloc), 5.19–5.25 (m, 1H, alloc), 4.96–5.04 (m, 2H, pent), 4.76–4.90 (m, 5H, H-2B, 2H of PhCH$_2$), 4.55–4.64 (m, 2H, alloc), 4.49 (d, J=7.6 Hz, 1H, H-1B), 4.35 (dd, J=2.1, 11.9 Hz, 1H, H-6$_a$A), 4.21 (at, J=9.2 Hz, 1H, H-4B), 4.05 (dd, J=4.0, 12.2 Hz, 1H, H-6$_b$A), 4.00 (d, J=9.5 Hz, 1H, H-5B), 3.86–3.95 (m, 2H, H-3B, pent), 3.80 (s, 3H, COOCH$_3$), 3.62–3.70 (m, 2H, H-3A, H-4A), 3.45–3.50 (m, 2H, H-5A, pent), 3.29–3.24 (m, 1H, H-2A), 2.00–2.16 (m, 5H, CH$_3$, pent-CH$_2$), 1.60–1.77 (m, 2H, pent-CH$_2$), 0.89 (s, 9H, tert-butyl), 0.01 (s, 3H, CH$_3$), 0.00 (s, 3H, CH$_3$); $^{13}$C-NMR (125 MHz, CDCl$_3$) δ 171.0, 168.6, 154.0, 138.1, 138.0, 137.7, 131.4, 128.6, 128.5, 128.0, 127.8, 127.7, 127.4, 119.6, 115.2, 101.2, 97.8, 82.6, 80.2, 77.4, 75.3, 74.9, 74.7, 74.5, 71.2, 70.9, 69.7, 69.1, 63.9, 62.5, 52.9, 30.0, 28.7, 26.0, 21.1, 18.1, −3.5, −4.9; FAB MS (C$_{44}$H$_{61}$N$_3$O$_{14}$Si) m/z (M)$^+$ calcd 883.3923, obsd 883.3930.

n-Pentenyl (6-O-acetyl-2-azido-3-O-benzyl-2-deoxy-α-D-glucopyranosyl)-(1→4)-methyl 2-O-allyloxycarbonyl-3-O-benzyl-β-D-glucopyranosiduronate 66

Compound 65 (55 mg, 0.062 mmol) was dissolved in THF (7 mL). Glacial acetic acid (1.75 mL) and HF/pyridine-complex (1 mL) were added and the solution was stirred at room temperature for 5 days. The mixture was poured into EtOAc and washed with brine, water, sat. NaHCO$_3$ and dried over Na$_2$SO$_4$. After filtration, the solvent was removed under reduced pressure. Flash chromatography on silica gel (hexanes:EtOAc 7:3) afforded 66 (41 mg, 0.053 mmol, 85%) as a colorless oil. [α]$^{24}_D$: +11.3 (c 1.02, CH$_2$Cl$_2$); IR (thin film on NaCl) 3470, 2922, 2109, 1752, 1454, 1367, 1255 cm$^{-1}$; $^1$H-NMR (500 MHz, CDCl$_3$) δ 7.27–7.43 (m, 10H, arom.), 5.84–5.92 (m, 1H, alloc), 5.74–5.82 (m, 1H, pent), 5.51 (d, J=3.7 Hz, 1H, H-1A), 5.31–5.37 (m, 1H, alloc), 5.23–5.26 (m, 1H, alloc), 4.95–5.04 (m, 2H, CH$_2$ olef.), 4.79–4.90 (m, 4H, H-2B, 3H of PhCH$_2$), 4.77 (d, J=10.7 Hz, 1H of PhCH$_2$) 4.56–4.65 (m, 3H, alloc, H-6$_a$A), 4.49 (d, J=7.7 Hz, 1H, H-1B), 4.21 (dd, J=8.9, 9.4 Hz, 1H, H-4B), 4.11 (dd, J=1.9, 12.6 Hz, 1H, H-6$_b$A), 3.99 (d, J=9.5 Hz, 1H, H-5B), 3.87–3.92 (m, 1H, pent), 3.86 (at, J=9.0 Hz, 1H, H-3B), 3.79 (s, 3H, COOCH$_3$), 3.74 (dd, J=8.6, 10.3 Hz, 1H, H-3A), 3.45–3.51 (m, 2H, pent, H-5A), 3.41 (dd, J=10.0, 8.7 Hz, 1H, H-4A), 3.25 (dd, J=3.7, 10.4 Hz, 1H, H-2A), 2.98 (bs, 1H, OH), 2.06–2.21 (m, 5H, pent, CH$_3$), 1.60–1.74 (m, 2H, pent); $^{13}$C-NMR (125 MHz, CDCl$_3$) δ 172.5, 168.7, 154.0, 138.1, 138.0, 137.7, 131.4, 128.8, 128.6, 128.4, 128.3, 128.0, 127.8, 119.6, 115.2, 101.3, 98.0, 82.6, 79.1, 75.6, 75.1, 74.9, 74.5, 71.0, 70.5, 69.7, 69.1, 62.9, 62.6, 53.0, 30.0, 28.7, 21.0; FAB MS (C$_{38}$H$_{47}$N$_3$O$_{14}$) m/z (M)$^+$ calcd 769.3058, obsd 769.3051.

n-Pentenyl (3,6-di-O-acetyl-2-azido-4-O-tert-butyldimethylsilyl-2-deoxy-α-D-glucopyranosyl)-(1→4)-(methyl 2-O-acetyl-3-O-benzyl-α-L-idopyranosyluronate)-(1→4)-(6-O-acetyl-3-O-benzyl-2-azido-2-deoxy-α-D-glucopyranosyl)-(1→4)-methyl 3-O-benzyl-2-O-monochloroacetyl-β-D-glucopyranosiduronate 67

Compound 59 (360 mg, 0.41 mmol) and 64 (186 mg, 0.24 mmol) were coevaporated with toluene and dried under vacuum for 1 h. The mixture was dissolved in CH$_2$Cl$_2$ (3 mL) and after cooling to −25° C., TMSOTf (370 μL, 0.1M in CH$_2$Cl$_2$) was added. The mixture was stirred for 4 h and then diluted with CH$_2$Cl$_2$ and filtered through a pad of Celite. The solvent was removed under reduced pressure and the residue was purified by silica gel column chromatography (toluene:EtOAc 90:10→80:20) to yield 67 (331 mg, 0.22 mmol, 91%) as a syrup. [α]$^{24}_D$: +40.0 (c 1.00, CHCl$_3$); IR (thin film on NaCl) 2930, 2107, 1728, 1538, 1362 cm$^{-1}$; $^1$H-NMR (500 MHz, CDCl$_3$) δ 7.39–7.27 (m, 20H, H-arom.), 5.77–5.74 (m, 1H, CH olef.), 5.43 (d, J=3.7 Hz 1H, H-1C), 5.35 (d, J=4.9 Hz, 1H, H-1B), 5.23 (t, J=10.4 Hz, 1H, H-3A), 5.12 (d, J=3.7 Hz, 1H, H-1A), 5.07 (t, 1H, H-2D), 5.01–4.84 (m, 6H, H-2B, CH$_2$ olef., PhCH$_2$, H-6$_a$A), 4.73–4.64 (m, 4H, 2 PhCH$_2$), 4.57 (d, J=4.6 Hz, 1H, H-5B), 4.47 (d, J=7.6 Hz, H-1D), 4.34 (m, 2H, H-6$_a$A, H-6$_a$C), 4.24–4.18 (m, 2H, H-6$_b$C, H-4D), 4.09 (t, 1H, H-4B), 4.05 (dd, 1H, J=3.3, 12.2 Hz, H-6bA), 4.00 (m, 2H, H-5D, H-3B), 3.92–3.81 (m, 6H, 1H of OCH$_2$, CH$_2$Cl, H-5A, H-3D, H-4C), 3.79–3.72 (m, 2H, H-4A, H-3C), 3.69 (s, 3H, COOCH$_3$), 3.67 (s, 3H, COOCH$_3$), 3.56–3.54 (m, 1H, H-5C), 3.45–3.42 (m, 1H, 1H of OCH$_2$), 3.31 (dd, J=3.7, 10.7 Hz, 1H, H-2C), 3.00 (dd, J=3.7, 10.7 Hz, 1H, H-2A), 2.13 (s, 6H, 2 CH$_3$), 2.10 (s, 3H, CH$_3$), 2.05–2.01 (m, 2H, pent-CH$_2$), 2.03 (s, 3H, CH$_3$), 1.69–1.60 (m, 2H, pent-CH$_2$), 0.84 (s, 9H, tert-butyl), 0.04 (s, 3H, CH$_3$), 0.02 (s, 3H, SiCH$_3$); $^{13}$C-NMR (125 MHz, CDCl$_3$) δ 171.0, 170.7, 170.2, 169.8, 168.6, 165.9, 137.9, 137.7, 137.5, 128.7, 128.4, 128.2, 128.1, 128.0, 127.9, 127,7, 127.3, 1 115.3, 101.0, 98.2, 97.7, 82.5, 78.2, 76.0, 75.1, 75.0, 74.7, 74.6, 74.4, 73.0, 72.6, 71.0, 69.8, 69.6, 69.0, 63.3, 62.4, 61.6, 52.4, 40.7, 30.0, 28.7, 26.6, 25.7, 21.8, 21.2, 18.0, −3.9, −4.8; FAB MS ($C_{68}H_{89}ClN_6O_{26}Si$) m/z (M)$^+$ calcd 1468.5284, obsd 1468.5361.

n-Pentenyl (3,6-di-O-acetyl-2-azido-4-O-tert-butyldimethylsilyl-2-deoxy-α-D-glucopyranosyl)-(1→4)-(methyl 2-O-acetyl-3-O-benzyl-β-L-idopyranosyluronate)-(1→4)-(6-O-acetyl-2-azido-3-O-benzyl-2-deoxy-α-D-glucopyranosyl)-(1→4)-methyl 3-O-benzyl-2-O-levulinyl-β-D-glucopyranosiduronate 68

Compound 62 (290 mg, 0.33 mmol) and 5 (173 mg, 0.22 mmol) were coevaporated with toluene and dried under vacuum for 1 h. The mixture was dissolved in $CH_2Cl_2$ (3 mL) and after cooling to −25° C., TMSOTf (330 μL, 0.1 M in $CH_2Cl_2$) was added. The mixture was stirred for 4 h and then diluted with $CH_2Cl_2$ and filtered through a pad of Celite. The solvent was removed under reduced pressure and the residue was purified by silica gel column chromatography (toluene:EtOAc 90:10→80:20) to yield 68 (289 mg, 88%) as a syrup. $^1$H-NMR (500 MHz, $CDCl_3$) δ 7.37–7.15 (m, 15H), 5.83–5.75 (m, 1H), 5.47 (d, J=4.0 Hz, 1H), 5.35 (d, J=4.9 Hz, 1H), 5.24 (dd, J=8.8, 10.7 Hz, 1H), 5.13 (d, J=3.3 Hz, 1H), 5.08–5.03 (m, 1H), 4.99–4.90 (m, 4H), 4.80–4.67 (m, 5H), 4.58 (d, J=4.9 Hz, 1H), 4.47 (d, J=7.3 Hz, 1H), 4.37–4.31 (m, 2H), 4.25–4.18 (m, 2H), 4.10 (at, J=6.1 Hz, 1H), 4.06 (dd, J=3.7, 12.2 Hz, 1H), 4.02–3.98 (m, 2H), 3.94–3.91 (m, 1H), 3.88–3.80 (m, 3H), 3.79–3.69 (m, 2H), 3.68 (s, 3H), 3.65 (s, 3H), 3.56–3.54 (m, 1H), 3.48–3.43 (m, 1H), 3.28 (dd, J=6.9, 10.3 Hz, 1H), 3.00 (dd, J=3.3, 10.7 Hz, 1H), 2.68 (t, J=6.7 Hz, 1H), 2.57–2.44 (m, 2H), 2.26–2.01 (m, 17H), 1.71–1.61 (m, 2H); $^{13}$C-NMR (125 MHz, $CDCl_3$) δ 206.2, 171.4, 170.6, 170.2, 170.0, 169.8, 168.9, 138.1, 138.0, 137.8, 137.5, 129.2, 128.7, 128.6, 128.4, 128.2, 128.1, 127.9, 127.7, 125.5, 115.1, 101.2, 98.3, 98.2, 97.3, 82.5, 78.1, 76.2, 76.0, 75.1, 74.5, 74.4, 74.3, 73.5, 73.0, 72.5, 70.9, 70.4, 70.3, 69.6, 69.4, 68.9, 63.2, 62.4, 61.8, 61.5, 52.8, 52.3, 37.9, 30.0, 29.9, 28.7, 28.0, 25.7, 21.6, 21.5, 21.0, 20.9, 18.0, −3.9, −4.9.

n-Pentenyl (6-O-acetyl-2-azido-3-O-benzyl-4-O-tert-butyldimethylsilyl-2-deoxy-α-D-glucopyranosyl-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl-(1→4)-methyl 3-O-benzyl-2-O-levulinyl-β-O-D-glucopyranosiduronate 69

Compound 60 (85 mg, 0.09 mmol) and 62 (60 mg, 0.07 mmol) were coevaporated with toluene and dried under vacuum for 1 h. The mixture was dissolved in $CH_2Cl_2$ (2 mL) and after cooling to −25° C., TMSOTf (90 μL, 0.1 M in $CH_2Cl_2$) was added. The mixture was stirred for 4 h and then diluted with $CH_2Cl_2$ and filtered through a pad of Celite. The solvent was removed under reduced pressure and the residue was purified by silica gel column chromatography (toluene:EtOAc 90:10→80:20) to yield 69 (107 mg, 86%) as a syrup. $^1$H-NMR (500 MHz, $CDCl_3$) δ 7.37–7.25 (m, 20H), 5.82–5.74 (m, 1H), 5.47 (d, J=3.6 Hz, 1H), 5.26 (d, J=4.6 Hz, 1H), 5.0.7–5.02 (m, 3H), 4.99–4.88 (m, 3H), 4.83–4.65 (m, 8H), 4.47 (d, J=7.3 Hz, 1H), 4.35–4.32 (m, 2H), 4.25–4.18 (m, 2H), 4.07–3.95 (m, 4H), 3.87–3.82 (m, 3H), 3.80–3.73 (m, 2H), 3.72–3.64 (m, 4H), 3.61 (s, 3H), 3.59–3.55 (m, 2H), 3.47–3.43 (m, 1H), 3.27 (dd, J=3.9, 10.3 Hz, 1H), 3.23 (dd, J=3.3, 10.1, 1H), 2.68 (t, J=6.7 Hz, 2H), 2.57–2.44 (m, 2H), 2.18 (s, 3H), 2.14 (s, 3H), 2.13–2.05 (m, 5H), 2.02 (s, 3H), 1.70–1.61 (m, 2H), 0.89 (m, 9H), −0.01 (s, 3H), −0.02 (s, 3H); $^{13}$C-NMR (125 MHz, $CDCl_3$) δ 206.2, 171.4, 170.9, 170.8, 170.1, 169.6, 168.9, 138.1, 137.9, 137.8, 137.7, 137.5, 128.7, 128.6, 128.4, 128.2, 128.0, 127.9, 127.8, 127.7, 127.4, 115.2, 101.2, 98.2, 97.7, 97.4, 82.6, 80.2, 78.1, 75.9, 75.2, 75.0, 74.8, 74.5, 74.0, 73.6, 72.7, 71.2, 70.8, 70.2, 70.0, 69.7, 69.5, 63.7, 63.2, 62.6, 61.9, 52.9, 52.1, 38.0, 30.1, 30.0, 28.7, 28.0, 26.0, 21.1, 21.0, 18.1, −3.53, −4.87.

n-Pentenyl (3,6-di-O-acetyl-2-azido-2-deoxy-α-D-glucopyranosyl)-(1→4)-(methyl 2-O-acetyl-3-O-benzyl-α-idopyranosyluronate)-(1→4)-(6-O-acetyl-2-azido-3-O-benzyl-2-deoxy-α-D-glucopyranosyl)-(1→4)-methyl 3-O-benzyl-2-O-monochloroacetyl-β-D-glucopyranosiduronate Compound 67 (60 mg, 0.21 mmol) was dissolved in THF (26 mL). Glacial acetic acid (6.4 mL) and HF/pyridine-complex (3.8 mL) were added and the solution was stirred at room temperature for three days. The mixture was poured into EtOAc and washed with brine, water, sat. $NaHCO_3$ and dried over $NASO_4$. After filtration, the solvent was removed under reduced pressure. Flash chromatography on silica gel (hexanes/EtOAc 5:3) afforded 70 (247 mg, 85%). $[α]^{24}_D$: +20.4 (c 1.00, $CHCl_3$); IR (thin film on NaCl) 3510, 2924, 2109, 1742 cm$^{-1}$; $^1$H-NMR (500 MHz, $CDCl_3$) δ 7.39–7.27 (m, 20H, arom.), 5.80–5.75 (m, 1H, CH olef.), 5.44 (d, J=3.7 Hz 1H, H-1C), 5.31 (d, J=4.9 Hz, 1H, H-1B), 5.22 (t, J=10.2 Hz, 1H, H-3A), 5.16–5.12 (m, 2H), 5.07–4.83 (m, 5H), 4.73–4.64 (m, 5H), 4.57–4.52 (d, 1H), 4.37 (d, 1H), 4.34–4.25 (m, 3H), 4.08 (m, 1H), 4.00–3.95 (m, 3H), 3.90–3.81 (m, 6H), 3.80–3.72 (m, 2H), 3.69 (s, 3H, $COOCH_3$), 3.67 (s, 3H, $COOCH_3$), 3.60–3.53 (m, 1H, H-5C), 3.51–3.42 (m, 1H of $OCH_2$), 3.27 (dd, J=3.7, 10.7 Hz, 1H, H-2C), 3.17 (dd, J=3.7, 10.7 Hz, 1H, H-2A), 3.07 (bs, 1H, OH), 2.14 (s, 3H, $CH_3$), 2.13 (s, 3H, $CH_3$), 2.12 (s, 3H, $CH_3$), 2.05–2.01 (m, 2H, pent-$CH_2$), 2.08 (s, 3H, $CH_3$), 1.74–1.60 (m, 2H, pent-$CH_2$); $^{13}$C-NMR (125 MHz, $CDCl_3$) δ 171.9, 171.3, 171.1, 170.3, 169.7, 168.6, 165.9, 138.0, 137.7, 137.4, 115.3, 100.9, 98.6, 98.4, 97.6, 82.5, 78.2, 75.8, 75.7, 75.1, 75.0, 74.9, 74.7, 74.6, 74.0, 73.8, 72.4, 71.4, 70.2, 70.1, 69.8, 69.5, 68.9, 63.3, 62.5, 61.9, 61.1, 52.9, 52.4, 40.6, 30.0, 28.7, 21.0, 21.0, 20.9; FAB MS ($C_{62}H_{75}ClN_6O_{26}$) m/z (M)$^+$ calcd 1354.4420, obsd 1354.441.

n-Pentenyl (3,6-di-O-acetyl-2-azido-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-methyl 3-O-benzyl-2-O-levulinyl-β-D-glucopyranosiduronate 71

Compound 68 (170 mg, 0.11 mmol) was dissolved in THF (13 mL). Glacial acetic acid (3 mL) and HF/pyridine-complex (1.88 mL) were added and the solution was stirred at room temperature for three days. The mixture was poured into EtOAc and washed with brine, water, sat. $NaHCO_3$ and dried over $Na_2SO_4$. After filtration, the solvent was removed under reduced pressure. Flash chromatography on silica gel (hexanes:EtOAc 5:3) afforded 71 (135 mg, 86%) as a pale yellow oil. $^1$H-NMR (500 MHz, $CDCl_3$) δ 7.37–7.15 (m, 15H), 5.82–5.74 (m, 1H), 5.47 (d, J=3.6 Hz, 1H), 5.29 (d, J=4.3 Hz, 1H), 5.21 (t, J=10.1 Hz, 1H), 5.07–5.02 (m, 2H), 4.98–4.90 (m, 3H), 4.79–4.68 (m, 5H), 4.61 (d, J=4.3 Hz, 1H), 4.50–4.46 (m, 2H), 4.32–4.30 (m, 1H), 4.25–4.14 (m, 3H), 4.07 (t, J=5.2 Hz, 1H), 3.98 (d, J=9.5 Hz, 1H), 3.95 (t, J=5.5 Hz, 1H), 3.90–3.82 (m, 4H), 3.74 (t, J=10.1 Hz, 1H), 3.67 (s, 3H), 3.66 (s, 3H), 3.56–3.54 (m, 1H), 3.47–3.42 (m, 2H), 3.27 (dd, J=3.6, 10.3 Hz, 1H), 3.17 (dd, J=3.6, 10.7 Hz, 1H), 3.01 (bs, 1H), 2.68 (t, J=6.7 Hz, 2H), 2.57–2.43 (m, 2H), 2.26–2.08 (m, 17H), 1.70–1.60 (m, 2H).

n-Pentenyl (6-O-acetyl-2-azido-3-O-benzyl-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-methyl 3-O-benzyl-2-O-levulinyl-β-O-pentenyl-D-glucopyranosiduronate 72

Compound 69 (70 mg, 0.045 mmol) was dissolved in THF (5.3 mL). Glacial acetic acid (1.3 mL) and HF/pyridine-complex (0.8 mL) were added and the solution was stirred at room temperature for three days. The mixture was poured into EtOAc and washed with brine, water, sat. NaHCO$_3$ and dried over Na$_2$SO$_4$. After filtration, the solvent was removed under reduced pressure. Flash chromatography on silica gel (hexanes/EtOAc 5:3) afforded 72 (50 mg, 75%). $^1$H-NMR (500 MHz, CDCl$_3$) δ 7.40–7.25 (m, 20H), 5.82–5.76 (m, 1H), 5.48 (d, J=3.6 Hz, 1H), 5.25 (d, J=4.6 Hz, 1H), 5.07–4.89 (m, 6H), 4.84 (s, 2H), 4.80–4.68 (m, 5H), 4.63 (d, J=4.3 Hz, 1H), 4.51 (dd, J=3.5, 12.5 Hz, 1H), 4.47 (d, J=7.3 Hz, 1H), 4.34–4.32 (m, 1H), 4.26–4.20 (m, 2H), 4.09 (dd, J=2.1, 12.5, 1H), 4.04 (t, J=5.5 Hz, 1H), 4.00 (d, J=9.5 Hz, 1H), 3.95 (t, J=5.5 Hz, 1H), 3.88–3.82 (m, 3H), 3.78–3.71 (m, 3H), 3.69–3.64 (m, 4H), 3.57 (s, 3H), 3.48–3.43 (m, 2H), 3.27 (d, J=3.6, 10.1 Hz, 1H), 3.21 (d, J=3.4, 10.1 Hz, 1H), 2.91 (d, J=4.0 Hz, 1H), 2.68 (t, J=6.7 Hz, 2H), 2.56–2.45 (m, 2H), 2.14 (s, 6H), 2.12–2.05 (m, 8H), 1.69–1.62 (m, 2H); $^{13}$C-NMR (125 MHz, CDCl$_3$) δ 206.2, 172.1, 171.4, 171.0, 170.0, 169.6, 168.9, 138.1, 138.0, 137.9, 137.5, 129.2, 129.0, 128.8, 128.7, 128.6, 128.4, 128.4, 128.2, 128.1, 128.0, 127.9, 127.8, 115.1, 101.2, 98.4, 98.2, 97.4, 82.5, 78.8, 78.2, 77.4, 75.7, 75.3, 75.2, 75.0, 74.5, 74.4, 73.9, 73.6, 73.4, 71.1, 70.5, 70.2, 70.0, 69.7, 69.4, 63.2, 62.8, 62.7, 61.9, 52.8, 52.2, 37.9, 30.0, 28.7, 28.0, 21.1, 20.9. O-(Methyl 2-O-acetyl-3-O-benzyl-4-O-tert-butyldimethylsilyl-β-L-idopyranosiduronate) trichloroacetimidate 73 tert-Butyldimethylsilyl trifluoromethanesulfonate (448 μL, 1.95 mmol) was added under argon to a solution of methyl 3-O-benzyl-1,2-O-isopropylidene-α-D-glucofuranosiduronate (600 mg, 1.77 mmol) and 2,6-lutidine (522 μL, 4.48 mmol) in CH$_2$Cl$_2$ (4 mL). After stirring for 1 h at room temperature, the reaction mixture was quenched with the addition of sat NaHCO$_3$. The mixture was diluted with CH$_2$Cl$_2$, the two phases were separated and the aqueous phase was extracted with CH$_2$Cl$_2$ (4×). The combined organic phases were dried over MgSO$_4$ and after filtration the solvent was removed under reduced pressure. Flash chromatography on silica gel (Hexanes:EtOAc 20:1) afforded methyl 3-O-benzyl-4-O-tert-butyldimethylsilyl-1,2-O-isopropylidene-β-L-idopyranosiduronate (786 mg, 98%) as a colorless solid. $^1$H-NMR (500 MHz, CDCl$_3$) δ 7.39–7.32 (m, 5H, arom.), 5.32 (d, J=2.4 Hz, 1H, H-1), 4.68 (d, J=11.9 Hz, 1H of PhCH$_2$), 4.62 (d, J=11.9 Hz, 1H of Ph CH$_2$), 4.38 (d, J=1.2 Hz, 1H, H-5), 4.06 (m, 1H, H-3), 3.94 (bs, 1H, H-4), 3.82 (m, 1H, H-2), 3.76 (s, 3H, COOCH$_3$), 1.59 (s, 3H, CH$_3$), 1.38 (s, 3H, CH$_3$), 0.82 (s, 9H, tert-butyl), −0.06 (s, 3H, CH$_3$), −0.07 (s, 3H, CH$_3$); $^{13}$C-NMR (125 MHz, CDCl$_3$) δ 169.8, 137.5, 128.8, 128.4, 128.1, 112.3, 96.9, 75.3, 75.1, 72.9, 72.7, 68.0, 52.3, 28.3 26.6, 25.6,18.0, −4.4, −5.3; FAB MS (C$_{23}$H$_{36}$O$_7$Si) m/z (M$^+$) calcd 452.2230, obsd 452.2211.

A solution of methyl 3-O-benzyl-4-O-tert-butyldimethylsilyl-1,2-O-isopropylidene-β-L-idopyranosiduronate (800 mg, 1.77 mmol) in dichloroacetic acid (40 mL, 60% aq) was stirred at room temperature for 3 h and diluted with water and neutralized with NaHCO$_3$ (24 g). The aqueous phase was washed three times with CH$_2$Cl$_2$ and the combined organic phases were dried over MgSO$_4$. After filtration, the solvent was removed under reduced pressure to afford methyl 3-O-benzyl-4-O-tert-butyldimethylsilyl-L-idopyranosiduronate (671 mg, 1.62 mmol, 92%) as a white solid. The compound can be further purified by silica gel column chromatography (hexane:EtOAc 70:30). FAB MS (C$_{20}$H$_{32}$O$_7$Si) m/z (M$^-$) calcd 412.1917, obsd 412.1896.

Pyridine (3.0 mL, 36 mmol), acetic anhydride (2.0 mL, 21.7 mmol) and DMAP (17 mg, 0.145 mmol) were added to a solution of 3-O-benzyl-4-O-tert-butyldimethylsilyl-L-idopyranosiduronate (600 mg, 1.45 mmol) in CH$_2$Cl$_2$ (20 mL). The solution was stirred at room temperature for 6 h, water was added and the mixture was stirred for one additional hour. The organic phase was washed with saturated solution of NaHCO$_3$, water and 10% HCl, dried over MgSO$_4$ and filtered. The solvent was removed under reduced pressure and the residue was purified by silica gel column chromatography (hexane:EtOAc 90:20) to yield methyl 1,2-di-O-acetyl-3-O-benzyl-4-O-tert-butyldimethylsilyl-α/β-L-idopyranosiduronate (708 mg, 1.42 mmol, 98%) as a colorless syrup. FAB MS (C$_{24}$H$_{36}$O$_9$Si) m/z (M)$^+$ calcd 496.2129, obsd 496.2129.

Benzylamine (600 μL, 5.4 mmol) was added to a solution of methyl 1,2-di-O-acetyl-3-O-benzyl-4-O-tert-butyldimethylsilyl-α/β-L-idopyranosiduronate (630 mg, 1.27 mmol) in Et$_2$O (40 mL) at 0° C. After 6 h, the mixture was diluted with CH$_2$Cl$_2$, filtered and washed with aqueous HCl (10%). The organic phase was dried over MgSO$_4$ and after filtration silica gel column chromatography (hexanes:EtOAc 90:10→80:20) afforded methyl 2-O-acetyl-3-O-benzyl-4-O-tert-butyldimethylsilyl-L-idopyranosiduronate (432 mg, 0.95 mmol, 75%) as a white solid. FAB MS (C$_{22}$H$_{34}$O$_8$Si) m/z (M)$^+$ calcd 454.2023, obsd 454.2016.

A solution of methyl 2-O-acetyl-3-O-benzyl-4-O-tert-butyldimethylsilyl-L-idopyranosiduronate (500 mg, 1.10 mmol) in CH$_2$Cl$_2$ (25 mL) was cooled to 0° C. Trichloroacetonitrile (1.7 mL, 17.0 mmol) and DBU (25 μL, 0.16 mmol) were added and after stirring the mixture at 0° C. for 1 h the solvents were removed under reduced pressure. Flash chromatography on silica gel (hexanes:EtOAc 85:15→70:30) afforded 73 (606 mg, 92%) as a colorless foam. $^1$H-NMR (500 MHz, CDCl$_3$) δ 8.65 (s, 1H, NH), 7.38–7.31 (m, 5H, arom.), 6.41 (s, 1H, H-1), 5.11 (m, 1H, H-2), 4.90 (d, J=1.8 Hz, 1H, H-5), 4.80 (d, J=11.9 Hz, 1H of PhCH$_2$), 4.61 (d, J=11.9 Hz, 1H of PhCH$_2$), 4.12 (m, 1H, H-3), 3.78 (s, 3H, COOCH$_3$), 3.66 (bs, 1H, H-4), 1.59 (s, 3H, CH$_3$), 1.38 (s, 3H, CH$_3$), 2.08 (s, 3H, CH$_3$), 0.83 (s, 9H, tert-butyl), −0.05 (s, 3H, CH$_3$), −0.13 (s, 3H, CH$_3$); $^{13}$C-NMR (125 MHz, CDCl$_3$) δ 170.7, 170.0, 160.8, 138.0, 129.7, 129.1, 128.9, (128.7×2), 96.1, 74.2, 72.6, 71.3, 68.8, 66.1, 53.0, (26.2), 26.1, 21.7, 18.5, −3.9, −4.9; FAB MS (C$_{24}$H$_{34}$Cl$_3$NO$_8$Si) m/z (M)$^+$ calcd 597.119, obsd 597.1143. n-Pentenyl (methyl 2-O-acetyl-3-O-benzyl-4-O-tert-butyldimethylsilyl-α-L-idopyranosiduronate)-(1→4)-(6-O-acetyl-2-azido-3-O-benzyl-2-deoxy-α-D-glucopyranosyl)-(1→4)-methyl 3-O-benzyl-2-O-levulinyl-β-D-glucopyranosid-uronate 74

Compound 73 (204 mg, 0.34 mmol) and 62 (206 mg, 0.26 mmol) were coevaporated with toluene and dried under vacuum for 1 h. The mixture was dissolved in CH$_2$Cl$_2$ (3 mL) and after cooling to −25° C., TMSOTf (340 μL, 0.1M in CH$_2$Cl$_2$) was added. The mixture was stirred for 4 h and then diluted with CH$_2$Cl$_2$ and filtered. The solvent was removed under reduced pressure and the residue was purified by silica gel column chromatography (toluene:EtOAc 90:10→80:20) to yield 74 (298 mg, 0.24 mmol, 93%) as a syrup. $^1$H-NMR (500 MHz, CDCl$_3$) δ 7.39–7.27 (m, 15H), 5.80–5.77 (m, 1H), 5.44 (d, J=3.7 Hz, 1H), 5.32 (d, J=5.8 Hz, 1H), 5.07–5.02 (m, 2H), 4.98–4.95 (m, 2H), 4.90–4.87 (m, 1H), 4.79 (d, J=10.9 Hz, 1H), 4.73–4.66 (m, 4H), 4.49 (d, J=5.2, 11H), 4.46 (d, J=7.3 Hz, 1H), 4.38 (dd, 1H), 4.21–4.12 (m, 2H), 3.99–3.91 (m, 2H), 3.89–3.81 (m, 3H), 3.75 (m, 2H), 3.71 (s, 3H), 3.68 (m, 1H), 3.58 (s, 3H), 3.47–3.42 (m, 1H), 3.29 (dd, J=3.3, 10.1 Hz, 1H), 2.68 (m, 2H), 2.56–2.43 (m, 2H), 2.14 (s, 3H), 2.12 (s, 3H), 2.07–2.04 (m, 2H), 2.00 (s, 3H), 1.17–1.57 (m, 2H), 0.83 (s, 9H), −0.01 (s, 3H), −0.06 (s, 3H); $^{13}$C-NMR (125 MHz, CDCl$_3$) δ 206.2, 171.4, 170.9, 170.4, 170.1, 168.9, 138.1, 138.2, 138.0, 137.8, 129.2, 128.6, 128.5, 128.4, 128.3, 128.0, 127.9, 127.8, 127.7, 115.1, 101.2, 98.0, 97.3, 82.5, 77.9, 77.4, 77.2, 76.2, 75.1, 74.5, 73.9, 73.5, 73.2, 71.7, 69.8, 69.4, 62.9, 61.7, 52.8, 51.8, 37.9, 30.0, 28.7, 28.0, 25.7, 21.1, 21.0, 27.9, −4.6, −5.1; FAB MS (C$_{61}$H$_{81}$N$_3$O$_{21}$Si) m/z (M)$^+$ calcd 1219.5132, obsd 1219.5107.

n-Pentenyl (methyl 2-O-acetyl-3-O-benzyl-α-L-idopyranosiduronate)-(1→4)-(6-O-acetyl-2-azido-3-O-benzyl-2-deoxy-α-D-glucopyranosyl)-(1→4)-(methyl 3-O-benzyl-2-O-levulinyl-β-D-glucopyranosiduronate 75

Compound 74 (45 mg, 0.037 mmol) was dissolved in THF (5 mL). Glacial acetic acid (1.3 mL) and HF/pyridine-complex (0.8 mL) were added and the solution was stirred at room temperature for three days. The mixture was poured into Et$_2$O and washed with brine, water, sat. NaHCO$_3$ and dried over Na$_2$SO$_4$. After filtration, the solvent was removed under reduced pressure. Flash chromatography on silica gel (hexanes/EtOAc 7:3) afforded 75 (33 mg, 0.03 mmol, 82%) as a colorless foam. $^1$H-NMR (500 MHz, CDCl$_3$) δ 7.39–7.27 (m, 15H), 5.49 (d, J=3.9 Hz, 1H), 5.07–4.95 (m, 4H), 4.90 (bs, 1H), 4.85 (bs, 1H), 4.83–4.73 (m, 4H), 4.65–4.62 (m, 4H), 4.47 (d, J=7.0 Hz, 1H), 4.35 (dd, 1H), 4.24–4.19 (m, 2H), 3.99 (d, J=9.0 Hz, 2H), 3.96 (m, 1H), 3.87–3.81 (m, 3H), 3.74–3.71 (m, 2H), 3.66 (s, 3H), 3.58 (dd, 1H), 3.48 (s, 3H), 3.48–3.43 (m, 1H), 3.28 (dd, J=3.7, 10.4 Hz, 1H), 2.68 (t, 2H), 2.60–2.45 (m, 3H), 2.14–2.07 (m, 11H), 1.68–1.60 (m, 2H); $^{13}$C-NMR (125 MHz, CDCl$_3$) δ 206.2, 171.4, 170.8, 169.7, 169.3, 168.8, 138.1, 137.8, 137.8, 137.3, 129.2, 128.8, 128.6, 128.4, 128.3, 127.9, 127.7, 127.7, 115.1, 101.2, 98.3, 97.6, 82.5, 78.4, 77.4, 75.1, 75.1, 74.8, 74.7, 74.6, 74.4, 73.6, 72.9, 69.8, 69.5, 69.0, 67.9, 67.7, 63.5, 61.9, 52.8, 52.3, 37.9, 30.0, 29.9, 28.7, 28.0, 21.6, 21.1; FAB MS (C$_{55}$H$_{67}$N$_3$O$_{21}$) m/z (M)$^+$ calcd 1105.4267, obsd 1105.4252.

tert-Butyldimethylsilyl (6-O-acetyl-2-azido-3,4-di-O-benzyl-2-deoxy-α-D-glucopyranosyl)-(1→4)-(methyl 3-O-benzyl-2-O-levulinyl-β-D-glucopyranosyl)-(1→4)-3,6-di-O-acetyl-2-azido-2-deoxy-β-D-glucopyranoside 76

Compound 55 (365 mg, 0.38 mmol) and 7 (105 mg, 0.26 mmol) were coevaporated with toluene and dried under vacuum for 1 h. The mixture was dissolved in CH$_2$Cl$_2$ (3 mL) and after cooling to −25° C., TMSOTf (20 μL, 0.1 M in CH$_2$Cl$_2$) was added. The mixture was stirred for 4 h and then diluted with CH$_2$Cl$_2$ and filtered through a pad of Celite. The solvent was removed under reduced pressure and the residue was purified by silica gel column chromatography (toluene:EtOAc 95:5→80:20) to yield 76 (195 mg, 0.16 mmol, 63%) as a syrup. $^1$H-NMR (500 MHz, CDCl$_3$) δ 7.37–7.24 (m, 15H), 5.40 (d, J=3.7 Hz, 1H), 4.99 (t, 1H), 4.92–4.87 (m, 3H), 4.84–4.70 (m, 3H), 4.67 (d, J=10.6 Hz, 1H), 4.60 (d, J=7.6 Hz, 1H), 4.57 (d, J=10.9 Hz, 1H), 4.50–4.47 (d, J=10.4 Hz, 1H), 4.42 (d, J=7.6 Hz, 1H), 4.27–4.12 (m, 4H), 3.90 (d, J=9.5 Hz, 1H), 3.85 (dd, J=8.5, 10.4 Hz, 1H), 3.78–375 (m, 1H), 3.76 (s, 1H), 3.73–3.60 (m, 2H), 3.55–3.50 (m, 2H), 3.32–3.27 (m, 2H), 2.74–2.63 (m, 2H), 2.59–2.54 (m, 2H), 2.12 (s, 3H), 2.11 (s, 3H), 2.04 (s, 3H), 2.03 (s, 3H), 0.9 (s 9H), 0.15 (s, 3H), 0.14 (s, 3H); $^{13}$C-NMR (125 MHz, CDCl$_3$) δ 206.1, 171.7, 170.8, 170.7, 169.8, 168.1, 145.7, 141.5, 137,7, 137.7, 137.6, 128.7, 128.7, 128.6, 128.6, 128.3, 128.3, 128.1, 128.0, 127.9, 127.7, 127.6, 127.5, 101.3, 97.6, 97.6, 82.5, 80.3, 76.8, 75.7, 75.2, 74.8, 74.7, 74.6, 73.1, 72.8, 71.8, 69.9, 66.5, 63.4, 62.5, 62.3, 52.9, 37.9, 37.7, 29.9, 27.8, 25.7, 21.1, 21.0, 20.9, 18.2, −4.3, −5.0; ES MS (C$_{57}$H$_{74}$N$_6$O$_{20}$Si) m/z (M)$^+$ calcd 1190.4727, obsd 1190.4735.

O-(6-O-acetyl-2-azido-3,4-di-O-benzyl-2-deoxy-α-D-glucopyranosyl)-(1→4)-methyl 3-O-benzyl-2-O-levulinyl-β-D-glucopyranosyl)-(1→4)-(3,6-di-O-acetyl-2-azido-2-deoxy-α/β-D-glucopyranosyl) trichloroacetimidate 77

A solution of 76 (80 mg, 0.07 mmol) in THF (1 mL) was cooled to 0° C. Glacial acetic acid (10 μL, 0.17 mmol) and TBAF (1M in THF, 110 μL, 0.11 mmol) were added in sequence. After 30 min the mixture was poured into Et$_2$O (100 mL) and washed with brine (3×). The organic layer was dried over Na$_2$SO$_4$, filtered and the solvent was removed under reduced pressure. The residue was dissolved in CH$_2$Cl$_2$ (20 mL) and the solution was cooled to 0° C. Trichloroacetonitrile (190 μL, 1.9 mmol) and DBU (5 μL, 0.03 mmol) were added and the mixture was stirred at 0° C. for 1 h and at room temperature for 3 h. After concentration, flash chromatography on silica gel (hexanes:EtOAc 85:15→70:30) afforded 77 (82 mg, 0.07 mmol, 87%) as a colorless foam. FAB MS (C$_{53}$H$_{60}$Cl$_3$N$_7$O$_{20}$) m/z (M)$^+$ calcd 1219.2959, obsd 1219.2963.

n-Pentenyl (6-O-acetyl-2-azido-3,4-di-O-benzyl-2-deoxy-α-D-glucopyranosyl)-(1→4)-(methyl 3-O-benzyl-2-O-levulinyl-β-D-glucopyranosyl)-(1→4)-(3,6-di-O-acetyl-2-azido-2-deoxy-α/β-D-glucopyranosyl)-(1→4)-(methyl 2-O-acetyl-3-O-benzyl-α-L-idopyranosiduronate)-(1→4)-(6-O-acetyl-2-azido-3-O-benzyl-2-deoxy-α-D-glucopyranosyl)-(1→4)-methyl 3-O-benzyl-2-O-levulinyl-β-D-glucopyranosiduronate 78

Compound 75 (50 mg, 0.04 mmol) and 77 (30 mg, 0.03 mmol) were coevaporated with toluene and dried under vacuum for 1 h. The mixture was dissolved in toluene (1 mL) and after cooling to −25° C., TBSOTf (20 μL, 0.1M in CH$_2$Cl$_2$) was added. The mixture was stirred for 2 h and then diluted with CH$_2$Cl$_2$ and filtered through a pad of Celite. The solvent was removed under reduced pressure and the residue was purified by silica gel column chromatography (toluene:EtOAc 95:5→80:20) to yield 78 (36 mg, 0.02 mmol, 62%) as a syrup. $[α]^{24}_D$: +35 (c 0.70, CH$_2$Cl$_2$); $^1$H-NMR (500 MHz, CDCl$_3$) δ 7.36–7.17 (m, 30H), 5.77–5.83 (m, 1H), 5.48–5.45 (m, 2H), 5.41 (d, J=3.7 Hz, 1H), 5.33 (t, 1H), 5.29 (d, J=3.7 Hz, 1H), 5.17–4.90 (m, 7H), 4.87–4.80 (m, 6H), 4.78–4.61 (m, 7H), 4.57–4.53 (m, 2H), 4.45 (d, J=7.9 Hz, 1H), 4.39 (d, J=7.9 Hz, 1H), 4.38–4.22 (m, 2H), 4.20–4.10 (m, 2H), 3.96 (d, J=9.4 Hz, 1H), 3.95–3.84 (m, 2H), 3.82–3.66 (m, 6H), 3.75 (s, 3H), 3.71 (s, 3H), 3.67 (s, 3H), 3.54–3.49 (m, 3H), 3.48–3.43 (m, 1H), 3.30 (dd, J=3.9, 10.4, Hz, 1H), 3.16 (dd, J=3.3, 10.1, Hz, 1H), 3.11 (dd, J=3.0, 10.4, Hz, 1H), 2.69–2.63 (m, 4H), 2.58–2.48 (m, 4H), 2.16 (s, 3H), 2.14 (s, 3H), 2.12 (s, 3H), 2.04 (s, 3H), 2.09–2.02 (m, 2H), 2.02 (s, 3H), 1.87 (s, 3H), 1.66–1.60 (m, 2H); $^{13}$C-NMR (125 MHz, CDCl$_3$) δ 207.2, 206.2, 171.4, 171.2, 171.0, 170.8, 170.7, 170.6, 170.1, 170.0, 169.0, 168.1, 138.2, 137.8, 137.7, 137.6, 129.2, 128.8, 128.7, 128.6, 128.5, 128.4, 128.3, 128.1, 127.9, 127.8, 127.5, 127.3, 125.5, 115.2, 101.5, 101.2, 99.6, 98.1, 97.7, 97.4, 82.9, 82.6, 80.4, 78.0, 77.4, 76.9, 75.8, 75.6, 75.2, 74.9, 74.8, 74.6, 74.4, 74.3, 73.6, 73.1, 71.5, 71.0, 70.0, 69.5, 69.3, 63.5, 63.3, 62.3, 61.9, 61.7, 61.0, 52.9, 52.8, 52.5, 37.9, 37.5, 31.2, 30.1, 30.0, 29.2, 28.7, 28.1, 27.7, 21.7, 21.2, 21.0, 20.9, 20.8; ES MS ($C_{106}H_{125}N_9O_{40}$) m/z (M+Na)$^+$ calcd 2186.7916, obsd 2186.7984.

n-Pentenyl (3,6-di-O-acetyl-2-azido-2-deoxy-α-D-glucopyranosyl)-(1→4)-(methyl 2-O-acetyl-3-O-benzyl-α-L-idopyranosyluronate)-(1→4)-(6-O-acetyl-3-O-benzyl-2-azido-2-deoxy-α-D-glucopyranosyl)-(1→4)-methyl 2,3-di-O-benzyl-β-D-glucopyranosiduronate 79

A solution of 70 (93 mg, 0.07 mmol) and thiourea (230 mg, 3.02 mmol) in DMF/pyridine (10/1, 2 mL) was stirred for 24 h. After removal of the solvent under reduced pressure, the residue was dissolved in $CHCl_3$ and filtered. The solvent was removed under reduced pressure and flash chromatography on silica gel afforded pent-4-enyl (3,6-di-O-acetyl-2-azido-2-deoxy-α-D-glucopyranosyl)-(1→4)-(methyl 2-O-acetyl-3-O-benzyl-α-L-idopyranosyluronate)-(1→4)-(6-O-acetyl-3-O-benzyl-2-azido-2-deoxy-α-D-glucopyranosyl)-(1→4)-methyl 3-O-benzyl-β-D-glucopyranosiduronate (79 mg, 0.06 mmol, 90%). [α]$^{23}_D$: +12.5 (c 0.80, $CHCl_3$); IR (thin film on NaCl) 2914, 2364, 2108, 1743, 1371; $^1$H-NMR (500 MHz, $CDCl_3$) δ 7.38–7.28 (m, 15H arom.), 5.85–5.77 (m, 1H, CH olef.), 5.57 (d, J=3.5 Hz, 1H, H-1C), 5.29 (d, J=4.5 Hz, 1H, H-1B), 5.22 (dd, J=10.5, 9.0 Hz, 1H, H-3A), 5.07 (d, J=3.0 Hz, 1H, H-1A), 5.02–4.97 (m, 3H, $CH_2$ olef., 1H of $\underline{CH_2}$Ph), 4.93–4.90 (m, 2H, H-2B, 1H of $\underline{CH_2}$Ph), 4.82–4.80 (A part of AB system, $J_{AB}$=11.0 Hz, 1H of $\underline{CH_2}$Ph), 4.76–4.68 (m, 3H of $\underline{CH_2}$Ph), 4.63 (d, J=4.5 Hz, 1H, H-5B), 4.49 (A part of ABX system, J=12.5, 3.5 Hz, 1H, H-6$_a$), 4.31 (d, J=7.5 Hz, 1H, H-1D), 4.29–4.24 (m, 2H, H-6$_a$, H-6$_b$), 4.16 (B part of ABX system, J=12.5, 2.0 Hz, 1H, H-6$_b$), 4.09–4.05 (m, 2H, H-4B, 1H), 4.00–3.84 (m, 5H, H-5A, H-4C, 1H of $OCH_2$, 3H), 3.77–3.71 (m, 2H, H-3D, H-3C), 3.67 (s, 3H, COOMe), 3.66 (s, 3H, COOMe), 3.62 (dt, J=7.5, 2.0 Hz, 1H, H-2D), 3.54–3.50 (m, 2H, 1H of $OCH_2$, 1H), 3.44 (dt, J=9.5, 5.0 Hz, 1H, H-4A), 3.27 (dd, J=10.5, 4.0 Hz, 1H, H-2C), 3.17 (dd, J=10.5, 3.5 Hz, 1H, H-2A), 3.03 (d, J=5.0 Hz, 1H, OH-4A), 2.34 (d, J=2.0 Hz, 1H, OH-2D), 2.20–2.05 (m, 14H, 4 $CH_3$, pent-$CH_2$), 1.77–1.68 (m, 2H, pent-$CH_2$); $^{13}$C-NMR (125 MHz, $CDCl_3$) δ 172.0, 171.3, 171.1, 170.3, 169.8, 169.0, 138.4, 138.2, 138.1, 137.4, 128.7, 128.6, 128.4, 128.3, 128.2, 128.0, 127.9, 127.8, 115.3, 103.1, 98.6, 98.4, 97.5, 83.9, 78.2, 75.8, 75.0, 74.9, 74.8, 74.7, 74.0, 73.9, 72.4, 71.4, 70.1, 70.0, 69.9, 69.6, 69.0, 63.3, 62.6, 62.0, 61.1, 52.8, 52.4, 30.3, 28.8, 21.1, 21.0, 20.9; ES MS ($C_{60}H_{74}N_6O_{25}$) m/z (M+Na)$^+$ calcd 1301.4601, obsd 1301.4596.

A solution of n-pentenyl (3,6-di-O-acetyl-2-azido-2-deoxy-α-D-glucopyranosyl)-(1→4)-(methyl 2-O-acetyl-3-O-benzyl-α-L-idopyranosyluronate)-(1→4)-(6-O-acetyl-3-O-benzyl-2-azido-2-deoxy-α-D-glucopyranosyl)-(1→4)-methyl 3-O-benzyl-β-D-glucopyranosiduronate (62 mg, 0.05 mmol) in $CH_2Cl_2$ (2.0 mL) was added to freshly activated powdered 4 Å molecular sieves (60 mg). Benzyl bromide (29 μL, 0.24 mmol) was added and the mixture was stirred at room temperature. After 30 minutes, $Ag_2O$ (67 mg, 0.29 mmol) was added and the mixture was stirred overnight. The mixture was filtered and the solvent was removed under reduced pressure and flash chromatography on silica gel afforded 79 (50 mg, 0.04 mmol, 76%) as a pale yellow oil. [α]$^{24}_D$: +23.9 (c 1.80, $CHCl_3$); IR (thin film on NaCl) 2924, 2108, 1743, 1496, 1453; $^1$H-NMR (500 MHz, $CDCl_3$) δ 7.36–7.25 (m, 20H arom.), 5.84–5.76 (m, 1H, CH olef.), 5.54 (d, J=4.0 Hz, 1H, H-1C), 5.28 (d, J=4.0 Hz, 1H, H-1B), 5.21 (t, J=9.5 Hz, 1H, H-3A), 5.07 (d, J=3.5 Hz, 1H, H-1A), 5.03–4.90 (m, 6H, $CH_2$ olef., H-2B, 3H of $\underline{CH_2}$Ph), 4.82–4.67 (m, 5H of $\underline{CH_2}$Ph), 4.62 (d, J=4.0 Hz, 1H, H-5B), 4.50–4.45 (m, 2H, H-6$_a$A, H-1D), 4.31–4.29 (A part of ABX system, J=12.0, 1.0 Hz, H-6$_a$C), 4.26–4.23 (B part of ABX system, J=12.0, 3.5 Hz, H-6$_b$C), 4.17–4.14 (B part of ABX system, J=12.5, 2.5 Hz, H-6$_b$A), 4.09–4.05 (m, 2H, H-4B, H-4D), 3.96–3.89 (m, 4H, H-5A, H-3B, H-5D, 1H of $OCH_2$), 3.86 (t, J=9.5 Hz, 1H, H-4C), 3.76–3.73 (m, 2H, H-3C, H-3D), 3.67 (s, 3H, COOCH$_3$), 3.65 (s, 3H, COOCH$_3$), 3.57–3.49 (m, 3H, H-5C, H-2D, 1H of $OCH_2$), 3.44 (td, J=10.5, 3.5 Hz, 1H, H-2A), 3.24 (dd, J=4.0, 10.0 Hz, 1H, H-2C), 3.17 (dd, J=3.5, 10.5 Hz, 1H, H-2A), 3.02 (d, J=5.0 Hz, 1H, OH), 2.16–2.04 (m, 14H, 3 $CH_3$, pent-$CH_2$), 1.77–1.70 (m, 2H, pent-$CH_2$); $^{13}$C-NMR (125 MHz, $CDCl_3$) δ 172.0, 171.3, 171.1, 170.3, 169.7, 169.1, 138.3, 138.2, 138.1, 137.4, 128.7, 128.6, 128.5, 128.4, 128.3, 128.2, 128.0, 127.8, 127.7, 115.3, 103.9, 98.6, 98.4, 97.4, 84.1, 81.9, 78.1, 75.75, 75.74, 75.4, 75.0, 74.9, 74.8, 74.4, 74.0, 73.8, 72.4, 71.4, 70.1, 70.0, 69.9, 69.5, 68.9, 63.2, 62.6, 62.0, 61.1, 52.8, 52.4, 30.3, 29.0, 21.0, 21.1, 20.9; ES MS ($C_{67}H_{80}N_6O_{25}$) m/z (M+Na)$^+$ calcd 1391.5070, obsd 1391.5107.

n-Pentenyl (3,4,6-tri-O-acetyl-2-azido-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-methyl 3-O-benzyl-β-D-glucopyranosiduronate 80

A solution of pent-4-enyl (3,6-di-O-acetyl-2-azido-2-deoxy-α-D-glucopyranosyl)-(1→4)-(methyl 2-O-acetyl-3-O-benzyl-α-L-idopyranosyluronate)-(1→4)-(6-O-acetyl-3-O-benzyl-2-azido-2-deoxy-α-D-glucopyranosyl)-(1→4)-methyl 3-O-benzyl-β-D-glucopyranosiduronate (50 mg, 0.04 mmol), pyridine (6.3 μL, 0.08 mmol), acetic anhydride (8 μL, 0.08 mmol) and catalytic DMAP was stirred at room temperature for 6 h. After removal of the solvent under reduced pressure, flash chromatography on silica gel (hexanes:EtOAc 1.5:1) afforded n-pentenyl (3,4,6-tri-O-acetyl-2-azido-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-methyl 3-O-benzyl-2-O-levulinyl-β-D-glucopyranosiduronate (57 mg, 0.08 mmol, quantitative) as a yellow oil. [α]$^{23}_D$: +165 (c 0.10, $CHCl_3$); $^1$H-NMR (500 MHz, $CDCl_3$) δ 7.38–7.24 (m, 15H arom.), 5.82–5.74 (m, 1H, CH olef.), 5.48 (d, J=4.0 Hz, 1H, H-1A), 5.34 (t, J=9.5 Hz, 1H, H-3A), 5.27 (d, J=4.0 Hz, 1H, H-1B), 5.08 (d, J=4.0 Hz, 1H, H-1C), 5.06–4.88 (m, 6H, H-2D, H-4A, $CH_2$ olef, H-2B, 1H of $\underline{CH_2}$Ph), 4.79–4.66 (m, 6H, 5H of $\underline{CH_2}$Ph, H-5B), 4.47 (d, J=7.5 Hz, 1H, H-1D), 4.32–4.23 (m, 2H, H-6$_a$C, H-6$_b$C), 4.22–4.18 (m, 2H, H-4D, 1H), 4.14–4.04 (m, 3H, H-4B, 2H), 3.99 (d, J=9.5 Hz, 1H, H-5D), 3.94 (t, J=5.0 Hz, 1H, H-3B), 3.87–3.82 (m, 3H, H-4C, 2H), 3.74 (t, J=10.0 Hz, 1H, H-3C), 3.67 (s, 3H, COOCH$_3$), 3.64 (s, 3H, COOCH$_3$), 3.57–3.55 (m, 1H, H-5C), 3.47–3.43 (m, 1H), 3.29–3.26 (m, 2H, H-2A, H-2C), 2.68 (t, J=6.5 Hz, 2H, lev-$CH_2$), 2.57–2.44 (m, 2H, lev-$CH_2$), 2.14–2.01 (m, 20H, 6 $CH_3$, pent-$CH_2$), 1.72–1.59 (m, 2H, pent-$CH_2$); $^{13}$C-NMR (125 MHz, $CDCl_3$) δ 206.2, 171.4, 171.0, 170.7, 170.2, 170.1, 169.7, 169.6, 168.8, 138.1, 138.0, 137.8, 137.3, 128.7, 128.6, 128.4, 128.3, 128.2, 127.9, 127.8, 115.1, 101.2, 98.4, 98.3, 97.4, 82.5, 78.2, 75.6, 75.4, 75.0, 74.5, 74.4, 73.9, 73.6, 70.3, 69.8, 69.6, 69.4, 68.6, 68.2, 63.3, 61.9, 61.5, 61.1, 52.8, 52.4, 37.9, 30.0, 28.7, 28.0, 21.0, 20.9, 20.87, 20.83, 20.7; ES MS ($C_{67}H_{82}N_6O_{28}$) m/z (M+Na)$^+$ calcd 1441.5069, obsd 1441.5098.

A solution of n-pentenyl (3,4,6-tri-O-acetyl-2-azido-2-deoxy-α-D-glucopyranosyl)-(1→4)-(methyl 2-O-acetyl-3-O-benzyl-α-L-idopyranosyluronate)-(1→4)-(6-O-acetyl-2-azido-3-O-benzyl-2-deoxy-α-D-glucopyranosyl)-(1→4)-methyl 3-O-benzyl-2-O-levulinyl-β-D- glucopyranosiduronate (42 mg, 0.03 mmol) in pyridine/ AcOH (3/2 0.3 mL) was cooled to 0° C. and hydrazine hydrate (7.4 mg, 0.15 mmol) was added. After 20 minutes acetone 82 mL) was added and the ice bath was removed. After stirring the mixture at room temperature for 30 minutes, the solvent was removed under reduced pressure and the residue was purified by silica gel column chromatography (hexanes:EtOAc 1:1) to afford 80 (35 mg, 0.03 mmol, 90%) as a pale yellow oil. $[\alpha]^{23}_D$: +138 (c 3.6, CHCl$_3$); $^1$H-NMR (500 MHz, CDCl$_3$) δ 7.38–7.26 (m, 15H, arom.), 5.84–5.76 (m, 1H, CH olef.), 5.58 (d, J=3.5 Hz, 1H, H-1A), 5.34 (dd, J=10.5, 9.5 Hz, 1H, H-3A), 5.27 (d, J=4.0 Hz, 1H, H-1B), 5.08 (d, J=3.5 Hz, 1H, H-1C), 5.05–4.97 (m, 4H, CH$_2$ olef., H-4A, 1H), 4.92 (t, J=4.5 Hz, 1H, H-2B), 4.89–4.87 (A part of AB system, $J_{AB}$=10.5 Hz, 1H of CH$_2$Ph), 4.82–4.79 (B part of AB system, $J_{AB}$=10.5 Hz, 1H of CH$_2$Ph), 4.76–4.67 (m, 4H), 4.32–4.19 (m, 4H), 4.11–4.04 (m, 4H), 3.97–3.90 (m, 3H), 3.85 (t, J=9.5 Hz, 1H), 3.77–3.71 (m, 2H), 3.67–3.60 (m, 7H, 2 COOMe, 1H), 3.55–3.49 (m, 2H), 3.29–3.25 (m, 2H, H-2C, H-2A), 2.40 (bs, 1H, OH), 2.14–2.02 (m, 17H, 5 CH$_3$, Pent-CH$_2$), 1.76–1.69 (m, 2H, pent-CH$_2$); $^{13}$C-NMR (500 MHz, CDCl$_3$) δ 171.0, 170.7, 170.3, 170.1, 169.8, 169.6, 168.9, 138.3, 138.1, 138.0, 137.3, 128.7, 128.6, 128.4, 128.3, 128.2, 127.9, 127.8, 115.3, 103.1, 98.4, 97.5, 83.9, 78.2, 75.6, 75.3, 74.9, 74.8, 74.7, 73.9, 70.3, 70.0, 69.5, 69.3, 68.6, 68.2, 63.3, 61.9, 61.4, 61.0, 52.8, 52.4, 30.3, 28.7, 21.1, 20.90, 20.88, 20.86, 20.79. ES MS (C$_{62}$H$_{76}$N$_6$O$_{26}$) m/z (M+Na)$^+$ calcd 1338.5152, obsd 1338.4932.

n-Pentenyl (2-deoxy-2-sodium sulfonatamido-3,4,6-tri-O-sodium sulfonato-α-D glucopyranosyl)-(1→4)-(sodium 2-O-sodium sulfonato-α-D-idopyranosyluronate)-(1→4)-(2-deoxy-2-sodium sulfonatamido-6-O-sodium sulfonato-α-D-glucopyranosyl)-(1→4)-sodium 2-O-sodium sulfonato-β-D-glucopyranosiduronate 81

A solution of 80 (44 mg, 0.03 mmol) in THF (3.0 mL) was cooled to −13° C. and 50% H$_2$O$_2$ (1.0 mL) and 0.7 M aq LiOH (0.8 mL) were added dropwise. The mixture was warmed to 0° C. over one hour and at room temperature overnight. Sodium hydroxide solution (4 M, 0.8 mL) was added and the mixture was stirred overnight. After acidification to pH 6.0 with 3 M HCl in MeOH, the solvent was partially removed under vacuum. The solution was diluted with EtOAc and the two phases were separated. The organic phase was washed twice with acidified aqueous sulfite (pH 3.5) and dried over Na$_2$SO$_4$. After filtration, the solvent was removed under reduced pressure and the residue was purified on Sephadex LH20 (CH$_2$Cl$_2$:EtOH 1:1) affording n-pentenyl (2-azido-2-deoxy-α-D-glucopyranosyl)-(1→4)-3-O-benzyl-α-L-idopyranosyluronic acid)-(1→4)-(2-azido-3-O-benzyl-2-deoxy-α-D-glucopyranosyl)-(1→4)-3-O-benzyl-β-D-glucopyranosiluronic acid (27 mg, mmol, 82%) as a colorless oil. ES MS (C$_{50}$H$_{62}$N$_6$O$_{21}$) m/z (M+Na)$^+$ calcd 1105.3865, obsd 1105.3806.

A solution of n-pentenyl (2-azido-2-deoxy-α-D-glucopyranosyl)-(1→4)-3-O-benzyl-α-L-idopyranosyluronic acid)-(1→4)-(2-azido-3-O-benzyl-2-deoxy-α-D-glucopyranosyl)-(1→4)-3-O-benzyl-β-D-glucopyranosiluronic acid (35 mg, 0.03 mmol) and sulfur trioxide triethylamine complex (88 mg, 0.48 mmol) in DMF (1.5 mmol) was stirred under nitrogen at 50° C. for 20 h. Aqueous NaHCO$_3$ (10%, 3 mL) was added at room temperature and the mixture was stirred for 3.5 h. The reaction mixture was concentrated, dissolved in MeOH and filtered through a pad of Celite. After removal of the solvent under reduced pressure, the residue was purified through a Sephadex G-25 column eluted with 0.2 N NaCl. After concentration and desalting through a Sephadex G-25 column eluted with water, n-pentenyl (2-azido-2-deoxy-3,4,6-tri-O-sodium sulfonato-α-D glucopyranosyl)-(1→4)-(sodium 3-O-benzyl-2-O-sodium sulfonato-α-D-idopyranosyluronate)-(1→4)-(2-azido-3-O-benzyl-2-deoxy-6-O-sodium sulfonato-α-D-glucopyranosyl)-(1→4)-sodium 3-O-benzyl-2-O-sodium sulfonato-β-D-glucopyranosiduronate (25 mg, 0.015 mmol, 50%) was obtained as a colorless solid. $^1$H-NMR (500 MHz, D$_2$O) δ 7.39–7.15 (m, 15H arom.), 5.82–5.74 (m, 1H, CH olef.), 5.25 (d, J=4.0 Hz, 1H, H-1C), 5.17 (bs, 1H, H-1B), 5.07 (d, J=3.5 Hz, 1H, H-1A), 4.99–4.87 (m, 2H, CH$_2$ olef.), 4.72–4.66 (m, 7H, 3 CH$_2$Ph, H-1D), 4.42–4.38 (m, 2H), 4.32–4.28 (m, 2H), 4.20–4.10 (m, 7H), 3.96–3.69 (m, 8H), 3.55–3.50 (m, 1H), 3.43 (dd, J=10.5, 3.5 Hz, 1H, H-2A), 3.34 (dd, J=10.0, 4.0 Hz, 1H, H-2C), 2.06–2.02 (m, 2H, pent-CH$_2$), 1.61–1.55 (m, 2H, pent-CH$_2$); $^{13}$C-NMR (125 MHz, D$_2$O) δ 139.7, 137.9, 137.4, 137.3, 129.9, 129.4, 129.2, 129.2, 128.9, 128.8, 115.4, 101.4, 98.0, 93.6, 82.8, 80.6, 78.6, 77.3, 76.5, 76.0, 75.3, 75.6, 75.3, 74.6, 73.0, 72.7, 71.4, 70.7, 70.4, 69.3, 68.6, 68.4, 67.4, 66.9, 63.6, 62.2, 29.9, 28.6; ES MS (C$_{50}$H$_{62}$N$_6$O$_{39}$S$_6$) m/z (M-2H)$^{2-}$ calcd. 780.0605, obsd. 780.0564.

A solution of n-pentenyl (2-azido-2-deoxy-3,4,6-tri-O-sodium sulfonato-α-D glucopyranosyl)-(1→4)-(sodium 3-O-benzyl-2-O-sodium sulfonato-α-D-idopyranosyluronate)-(1→4)-(2-azido-3-O-benzyl-2-deoxy-6-O-sodium sulfonato-α-D-glucopyranosyl)-(1→4)-sodium 3-O-benzyl-2-O-sodium sulfonato-β-D-glucopyranosiduronate (25 mg, 0.02 mmol) in EtOH/water (2/1, 6.0 mL) was treated by a stream of hydrogen in the presence of Pd/C catalyst (10%, 40 mg) for three days. After filtration on a pad of Celite, the solvent was removed under reduced pressure. $^1$H-NMR (500 MHz, D$_2$O) δ 5.41 (bs, 1H), 5.29 (bs, 1H), 5.10 (bs, 1H), 4.78 (bs, 1H), 4.60–4.28 (m, 2H), 4.24–3.57 (m, 17H), 3.55–3.41 (m, 2H), 3.13 (bs, 1H), 1.46–1.41 (m, 2H), 1.18–1.12 (m, 4H), 0.70 (t, J=7.0 Hz, 3H); ES MS (C$_{29}$H$_{50}$N$_2$O$_{39}$S$_6$) m/z (M−2H)$^{2-}$ calcd. 620.0085, obsd 620.0040.

The residue (20 mg, 0.02 mmol) was dissolved in water (4 mL). Sulfur trioxide pyridine complex (101 mg, 0.6 mmol) was added in five portions every 30 minutes with the pH being maintained at 9.5 by addition of 4N NaOH. After 3.5 h, the reaction mixture was concentrated and purified through a Sephadex G-25 column eluted with 0.2 N NaCl. After concentration and desalting through a Sephadex G-25 eluted with water, 81 (13 mg, 0.01 mmol, 60%) was obtained as a solid. $[\alpha]^{23}_D$: +57 (c 1.2, CHCl$_3$); $^1$H-NMR (500 MHz, D$_2$O) δ 5.47 (d, J=3.0 Hz, 1H), 5.42 (d, J=3.0 Hz, 1H), 5.03 (bs, 1H), 4.48 (d, J=8.0 Hz, 1H), 4.37–4.00 (m, 9H), 3.97 (t, J=8.0 Hz, 1H), 3.86–3.81 (m, 2H), 3.76–3.68 (m, 4H), 3.54–3.51 (m, 2H), 3.46 (dd, J=10.5, 3.0 Hz, 1H), 3.14 (dd, J=10.0, 3.5 Hz, 1H), 1.50–1.45 (m, 2H), 1.22–1.16 (m, 6H), 0.74 (at, J=7.0 Hz, 3H); HSQC anomeric cross peaks (D$_{2O}$) δ (4.48×100.8), (5.03×99.8), (5.42×98.2), (5.47×95.4). ES MS (C$_{29}$H$_{44}$N$_2$O$_{45}$S$_8$Na$_6$) m/z (M)$^+$ calcd. 1533.8, obsd. 1534.1.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A disaccharide selected from the group consisting of:

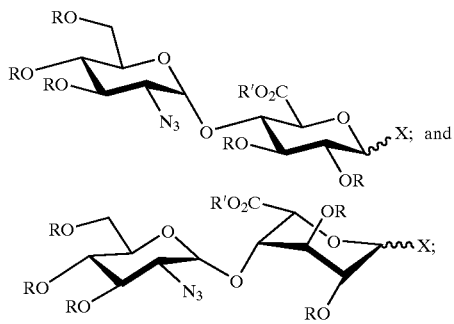

wherein

X represents independently for each occurrence hydroxyl, acyloxy, silyloxy, halide, alkylthio, arylthio, 4-alkenyloxy, aryloxy, or —OC(NH)CCl₃;

R represents independently for each occurrence H, alkyl, aryl, arylalkyl, heteroarylalkyl, silyl, acyl, alkenyloxycarbonyl, or aralkyloxycarbonyl; and R' represents independently for each occurrence H, alkyl, aryl, arylalkyl, or heteroarylalkyl.

2. The disaccharide of claim 1, wherein X represents fluoro, bromo, 4-pentenyloxy or —OC(NH)CCl₃.

3. The disaccharide of claim 1, wherein R' represents independently for each occurrence alkyl.

4. The disaccharide of claim 1, wherein X represents fluoro, bromo, 4-pentenyloxy or —OC(NH)CCl₃; and R' represents independently for each occurrence alkyl.

5. The disaccharide of claim 1, wherein said disaccharide is selected from the group consisting of:

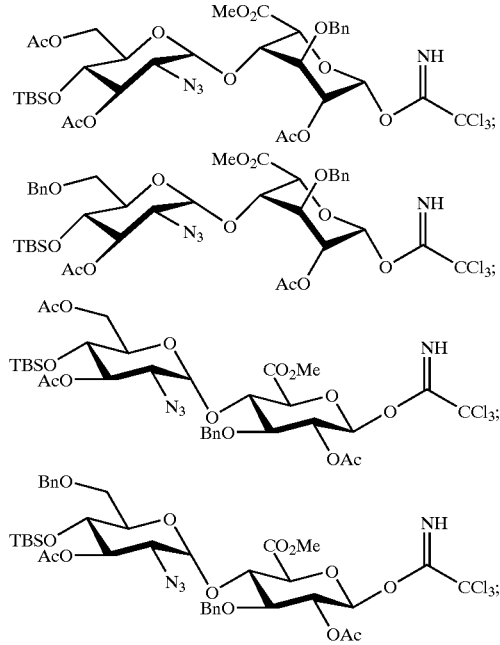

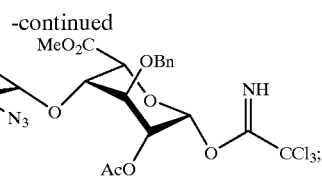

6. A trisaccharide represented by:

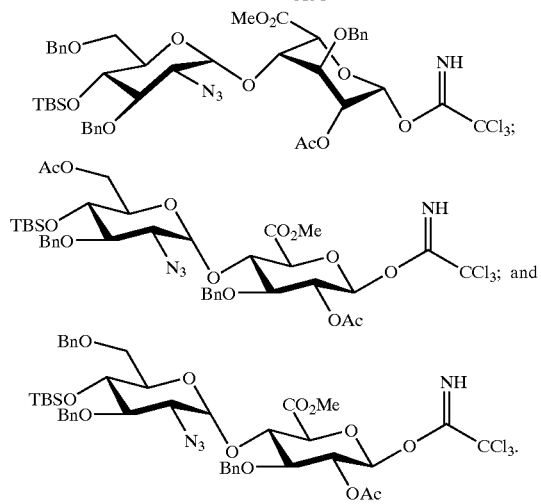

wherein

X represents independently for each occurrence hydroxyl, acyloxy, silyloxy, halide, alkylthio, arylthio, 4-alkenyloxy, aryloxy, or —OC(NH)CCl₃;

R represents independently for each occurrence H, alkyl, aryl, arylalkyl, heteroarylalkyl, silyl, acyl, alkenyloxycarbonyl, or aralkyloxycarbonyl; and R' represents independently for each occurrence H, alkyl, aryl, arylalkyl, or heteroarylalkyl.

7. The trisaccharide of claim 6, wherein X represents fluoro, bromo, 4-pentenyloxy or —OC(NH)CCl₃.

8. The trisaccharide of claim 6, wherein R' represents independently for each occurrence alkyl.

9. The trisaccharide of claim 6, wherein X represents fluoro, bromo, 4-pentenyloxy or —OC(NH)CCl₃; and R' represents independently for each occurrence alkyl.

10. The trisaccharide of claim 6, wherein said trisaccharide is selected from the group consisting of:

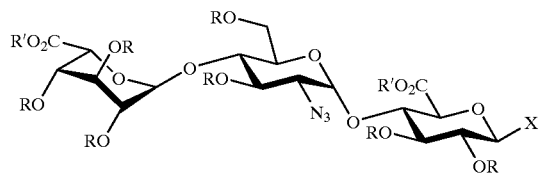

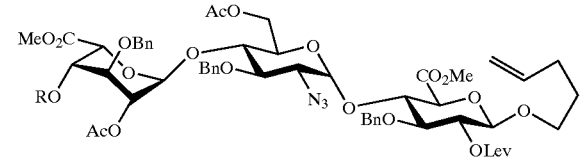

wherein
R is H or silyl.

11. A method of preparing a glycosaminoglycan, comprising the step of:

reacting a first mono-, di- or tri-saccharide, comprising an activated anomeric carbon, with a second mono-, di- or tri-saccharide, comprising a hydroxyl or amino group, to form an oligosaccharide linked to a solid support, comprising a glycosidic linkage between said anomeric carbon of said first mono-, di- or tri-saccharide and said hydroxyl or amino group of said second mono-, di- or tri-saccharide; wherein the second mono-, di- or tri-saccharide is covalently linked to a solid support at an anomeric position; and said activated anomeric carbon is activated by a hydroxyl, acyloxy, silyloxy, halide, alkylthio, arylthio, 4-alkenyloxy, aryloxy, or —OC(NH)CCl$_3$ group.

12. The method of claim 11, wherein the first mono-, di- or tri-saccharide is not identical to the second mono-, di- or tri-saccharide.

13. The method of claim 11 or 12, further comprising the step of:
    cleaving said covalent linkage between said oligosaccharide linked to a solid support and said solid support with an alkene metathesis catalyst and an alkene.

14. The method of claim 11 or 12, further comprising the step of:
    sulfating a hydroxyl or amino moiety of said oligosaccharide linked to a solid support.

15. The method of claim 11 or 12, further comprising the step of:
    removing a hydroxyl or amino protecting group from said oligosaccharide linked to a solid support by hydrogenolysis.

16. A method of preparing an oligosaccharide comprising an α-glucosamine glycosidic linkage, comprising the step of:
    reacting a uronic acid glycopyranosyl acceptor, comprising a hydroxyl group at C4 and a cyclic acetal comprising C1 and C2, with a glycosyl donor, comprising an activated anomeric carbon and an azide functional group at C2, to form an oligosaccharide comprising an α-glycosidic linkage between said hydroxyl group of said uronic acid glycopyranosyl acceptor and said anomeric carbon of said glycosyl donor.

17. The method of claim 16, wherein said uronic acid glycopyranosyl acceptor is an iduronic acid glycopyranosyl acceptor.

18. The method of claim 16, wherein said uronic acid glycopyranosyl acceptor is a glucuronic acid glycopyranosyl acceptor.

19. The method of claim 16, 17, or 18, wherein said glycosyl donor is a glycosyl fluoride or glycosyl trichloroacetimidate.

20. The method of claim 19, wherein said cyclic acetal comprising C1 and C2 of said uronic acid glycopyranosyl acceptor is an isopropylidene acetal or a cyclopentylidene acetal.

21. A trisaccharide represented by:

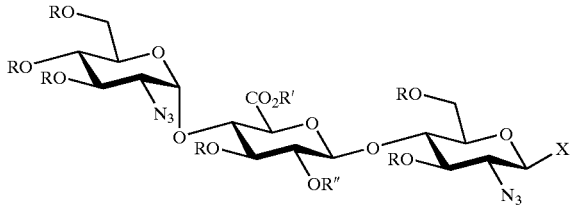

wherein
X represents independently for each occurrence hydroxyl, silyloxy, halide, alkylthio, arylthio, alkoxy, aryloxy, or —OC(NH)CCl$_3$;
R represents independently for each occurrence H, alkyl, aryl, arylalkyl, heteroarylalkyl, silyl, acyl, alkenyloxycarbonyl, or aralkyloxycarbonyl;
R' represents independently for each occurrence H, alkyl, aryl, arylalkyl, or heteroarylalkyl; and
R" represents independently for each occurrence H, alkyl, aryl, heteroarylalkyl, silyl, acyl, alkenyloxycarbonyl, or aralkyloxycarbonyl.

22. The trisaccharide of claim 21, wherein X represents fluoro, bromo, 4-pentenyloxy or —OC(NH)CCl$_3$.

23. The trisaccharide of claim 21, wherein R' represents independently for each occurrence alkyl.

24. The trisaccharide of claim 21, wherein X represents fluoro, bromo, 4-pentenyloxy or —OC(NH)CCl$_3$; and R' represents independently for each occurrence alkyl.

25. The trisaccharide of claim 21, wherein said trisaccharide is:

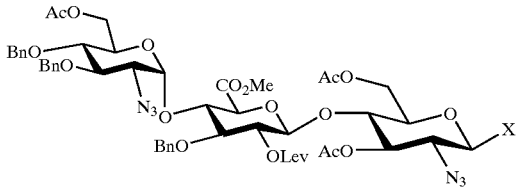

wherein
R is silyloxy or —OC(NH)CCl$_3$.

* * * * *

UNITED STATES PATENT AND TRADEMARK OFFICE
CERTIFICATE OF CORRECTION

PATENT NO. : 6,846,917 B2
DATED : January 25, 2005
INVENTOR(S) : Seeberger, P.H. et al.

It is certified that error appears in the above-identified patent and that said Letters Patent is hereby corrected as shown below:

Column 80,
Line 49, replace "R" with -- X --.

Signed and Sealed this

Third Day of May, 2005

JON W. DUDAS
*Director of the United States Patent and Trademark Office*